(12) United States Patent
Ochiai et al.

(10) Patent No.: US 8,110,388 B2
(45) Date of Patent: Feb. 7, 2012

(54) LYSOPHOSPHATIDIC ACID ACYLTRANSFERASE GENES

(75) Inventors: Misa Ochiai, Osaka (JP); Hisanori Tokuda, Osaka (JP)

(73) Assignee: Suntory Holdings Limited, Osaka (JP)

( * ) Notice: Subject to any disclaimer, the term of this patent is extended or adjusted under 35 U.S.C. 154(b) by 407 days.

(21) Appl. No.: 12/303,320

(22) PCT Filed: May 23, 2008

(86) PCT No.: PCT/JP2008/059564
§ 371 (c)(1),
(2), (4) Date: Dec. 3, 2008

(87) PCT Pub. No.: WO2008/146745
PCT Pub. Date: Dec. 4, 2008

(65) Prior Publication Data
US 2010/0203218 A1    Aug. 12, 2010

(30) Foreign Application Priority Data

May 25, 2007  (JP) .................................. 2007-139046
Dec. 14, 2007  (JP) .................................. 2007-323965

(51) Int. Cl.
| C12N 9/10 | (2006.01) |
| C12N 15/00 | (2006.01) |
| C12N 1/20 | (2006.01) |
| C12P 7/64 | (2006.01) |
| C12P 21/04 | (2006.01) |
| C12Q 1/00 | (2006.01) |
| C07H 21/04 | (2006.01) |

(52) U.S. Cl. ...... 435/193; 435/4; 435/252.3; 435/320.1; 435/440; 435/69.1; 435/134; 435/71.1; 536/23.2

(58) Field of Classification Search ........................ None
See application file for complete search history.

(56) References Cited

U.S. PATENT DOCUMENTS

| 7,157,254 | B1 | 1/2007 | Akimoto et al. |
| 2006/0094090 | A1 | 5/2006 | Damude et al. |
| 2006/0094092 | A1* | 5/2006 | Damude et al. ............... 435/134 |
| 2006/0110806 | A1* | 5/2006 | Damude et al. ............... 435/134 |
| 2006/0174376 | A1 | 8/2006 | Renz et al. |
| 2007/0072275 | A1 | 3/2007 | Ochiai et al. |

FOREIGN PATENT DOCUMENTS

| WO | 2001/012780 | 2/2001 |
| WO | 2004/076617 | 9/2004 |
| WO | 2005/019437 | 3/2005 |
| WO | 2008/146745 | 12/2008 |

OTHER PUBLICATIONS

Meinkoth et al. Anal. Biochem. 138, 26 (1984).*
Branden et al. Iintroduction to Protein Structure, Garland Publishing Inc., New York, p. 247, 1991.*
Jack Coleman, "Characterization of the *Escherichia coli* gene for 1-acyl-*sn*-glycerol-3-phosphate acyltransferase (*plsC*)" *Mol. Gen. Genet.* (1992) vol. 232, pp. 295-303.
M. Marek Nagiec et al., "A Suppressor Gene That Enables *Saccharomyces cerevisiae* to Grow without Making Sphingolipids Encodes a Protein That Resembles an *Escherichia coli* Fatty Acyltransferase" *The Journal of Biological Chemistry* (1993) vol. 268, No. 29, pp. 22156-22163.
S. Chatrattanakunchai et al., "Oil Biosynthesis in Microsomal Membrane Preparations from *Mortierella alpina*" *Biochemical Society Transactions* (2000) vol. 28, pp. 707-709.
Phillip Calder, "n-3 Fatty Acids, Inflammation, and Immunity—Relevance to Postsurgical and Critically III patients" *Lipids* (2004) vol. 39, pp. 1147-1161.
Richard Heath et al., "A Conserved Histidine is Essential for Glycerolipid Acyltransferase Catalysis" *The Journal of Bacteriology* (1998), vol. 180, pp. 1425-1430.
Erwin Zinser et al., "Phospholipid Synthesis and Lipid Composition of Subcellular Membranes in the Unicellular Eukaryote *Saccharomyces cerevisiae*" *The Journal of Bacteriology* (1991), vol. 173, pp. 2026-2034.
Search report from E.P.O. that issued with respect to patent family member European Patent Application No. 08764610.5, mailing date is May 20, 2011.

* cited by examiner

*Primary Examiner* — Yong Pak
(74) *Attorney, Agent, or Firm* — Greenblum & Bernstein, PLC

(57) ABSTRACT

The present invention provides novel lysophosphatidic acid acyltransferase genes.
A nucleic acid comprising the nucleotide sequence shown in SEQ ID NO: 1, 3, 36 or 37 or a fragment thereof.

5 Claims, 6 Drawing Sheets

Figure 2

```
   1  CCCCGTCTTTACTCCTGCACACAGACACACACCCACACTCTCTCTTTCCTGGTTTGAACAGATCCCAATTGCCGACTCCATCTTTCTCCATACTCTTCAC
 101  CCCTCCCATCGCCCTCCTTTCACTTCCTCTGTTTCTCATCTGACGCCAATCGTAAGGATGTCATCAATGTCATCAATAGAGCCCGCACTGTCCTCGTTTC
                                                              M  S  S  M  S  S  I  E  P  A  L  S  S  F  P ·

201  CAGGCAACCTGGCGGTCATCCTTGTTTTCTACCTGGCACTTCCACGACTTCTTGCCGTCCTGCCACAAAAGATTCAGTTCATCGCCAAATGTCTCATTGT
      · G  N  L  A  V  I  L  V  F  Y  L  A  L  P  R  L  L  A  V  L  P  Q  K  I  Q  F  I  A  K  C  L  I  V ·

301  CCTTACAGCCACCTTCCTCATGTCTGTGGCAGGATGCTTTGTCGCCATTGTCTGTGCTCTCCTCCAAAAGCGCTATGCCATAAATTACGTGGTTGCGAGG
      · L  T  A  T  F  L  M  S  V  A  G  C  F  V  A  I  V  C  A  L  L  Q  K  R  Y  A  I  N  Y  V  V  A  R

401  ATCTTTTCTTATATCGCATGCAGGCCTTGTGGAGTCACGTTCAATATCGTGGGCGAAGAACACCTCGAGAACACTCCAGCAATCGTTGTCTGCAACCACC
        I  F  S  Y  I  A  C  R  P  C  G  V  T  F  N  I  V  G  E  E  H  L  E  N  T  P  A  I  V  V  C  N  H  Q ·

501  AGAGCTCCATGGATATGATGGTCTTGGGACGAGTGTTCCCAATGCGCTGCGTGGTTATGGCCAAGAAGGAACTTCAGTACTTTCCATTTCTCGGCATCTT
      · S  S  M  D  M  M  V  L  G  R  V  F  P  M  R  C  V  V  M  A  K  K  E  L  Q  Y  F  P  F  L  G  I  F ·

601  TATGACGCTGAGCAATGCCATTTTTATTGACCGCAAGAATCATAAGAAGGCCATTGAGTCTACAACCCAGGCCGTTGCTGACATGAAGAAGCACAACTCT
      · M  T  L  S  N  A  I  F  I  D  R  K  N  H  K  K  A  I  E  S  T  T  Q  A  V  A  D  M  K  K  H  N  S

701  GGGATCTGGATCTTCCCCGAGGGAACTCGCTCCCGGCTTGACACGGCCGACCTGCTGCCATTCAAGAAGGGAGCCTTTCATCTTGCAATCCAGTCAGGAC
        G  I  W  I  F  P  E  G  T  R  S  R  L  D  T  A  D  L  L  P  F  K  K  G  A  F  H  L  A  I  Q  S  G  L ·

801  TTCCCATCCTACCCATTGTCAGCGCTGGATACAACCATATCTACGATTCTGCCAAGCGATCTTTCCCTGGCGGTGAGCTCGAGATCAGGGTTTTGGAGCC
      · P  I  L  P  I  V  S  A  G  Y  N  H  I  Y  D  S  A  K  R  S  F  P  G  G  E  L  E  I  R  V  L  E  P ·

901  CATACCTACCACAGGCATGACGGCCGATGATGTGAACGATCTGATGGAGCGGACACGGGCAGTGATGTTGAAGAACCTAAAGGAGATGGATGTCAACTCC
      · I  P  T  T  G  M  T  A  D  D  V  N  D  L  M  E  R  T  R  A  V  M  L  K  N  L  K  E  M  D  V  N  S

1001  TTGGCAGTATCTTCAAAACCCTCGCTCTCAGTGGACGAGCTCAAGTCAGCGCCCGCACTGAAGCAGGAGGCGAAGTCGACTGCCGGTGGTGGAGGAAGAGG
        L  A  V  S  S  K  P  S  L  S  V  D  E  L  K  S  A  P  A  L  K  Q  E  A  K  S  T  A  V  V  E  E  E  G ·

1101  GGGTTAGCTACGACAGCGTGAAGAAGAGGAAGACGGTCAAGGCTTAGATCGTGGGTAATGGTGATATATGTATTTAGTTCACGCACTATTAAAATCCTGA
      · V  S  Y  D  S  V  K  K  R  K  T  V  K  A

1201  TGTCCTT
```

Figure 3

```
   1  CTCTTCCATTCAACGATCGTTTTCTTCCCTAGCACACGTTTCTGTTCGTCCGACATGTCCATAGGCTCTTCTAATCCTGTCCTACTGGCAGCGATCCCCT
                                                                     M  S  I  G  S  S  N  P  V  L  L  A  A  I  P  F  ·

101  TCGTCTACCTTTTTGTCCTCCCTCGCATCCTCGCCTTCCTCCCTCAAAAGGCCCAGTTCCTCGCAAAATGTATCGTGGTCTTGATCGCCACCCTCATCAT
      ·V  Y  L  F  V  L  P  R  I  L  A  F  L  P  Q  K  A  Q  F  L  A  K  C  I  V  V  L  I  A  T  L  I  M  ·

201  GTCCGTCGCAGGCTGCCTCATCTCTATTGTCTGTGCGCTCCTCGACAAACGCTATGTGATCAACTACGTTGTCTCAAGACTCTTCTCATTCCTTGCAGCA
      ·S  V  A  G  C  L  I  S  I  V  C  A  L  L  D  K  R  Y  V  I  N  Y  V  V  S  R  L  F  S  F  L  A  A

301  AGACCCTGCGGCGTCACTTACAAGATTGTGGGCGAGGAGCATTTGGATAAGTACCCCGCCATTGTCGTTTGCAACCACCAGAGCTCAATGGACATGATGG
         R  P  C  G  V  T  Y  K  I  V  G  E  E  H  L  D  K  Y  P  A  I  V  V  C  N  H  Q  S  S  M  D  M  M  V  ·

401  TTCTGGGACGCGTCTTCCCTAAGCACTGTGTCGTCATGGCAAAGAAGGAGCTTCTTTACTTTCCGTTCCTGGGCATGTTCATGAAACTGAGCAATGCCAT
      ·L  G  R  V  F  P  K  H  C  V  V  M  A  K  K  E  L  L  Y  F  P  F  L  G  M  F  M  K  L  S  N  A  I  ·

501  TTTCATCGACCGCAAGAACCATAAGAAGGCGATCGAGTCTACCACCCAAGCTGTCGCCGACATGAAGAAGCACAACTCTGGAATCTGGATTTTCCCCGAA
      ·F  I  D  R  K  N  H  K  K  A  I  E  S  T  T  Q  A  V  A  D  M  K  K  H  N  S  G  I  W  I  F  P  E

601  GGAACACGTTCCCGCTTGGACAAGGCCGATCTCTTGCCCTTCAAGAAGGGAGCCTTCCACCTCGGCATTCAAGCTCAACTTCCCATCCTCCCCATCGTCT
         G  T  R  S  R  L  D  K  A  D  L  L  P  F  K  K  G  A  F  H  L  A  I  Q  A  Q  L  P  I  L  P  I  V  S  ·

701  CGCAAGGATACTCACACATCTATGATTCATCAAAACGCTACTTCCCCGGTGGAGAGCTCGAGATCAGAGTCCTGGAACCCATCCCTACCAAGGGATTGAC
      ·Q  G  Y  S  H  I  Y  D  S  S  K  R  Y  F  P  G  G  E  L  E  I  R  V  L  E  P  I  P  T  K  G  L  T  ·

801  CACAGACGATGTCAACGACCTGATGGACAAGACACGCAACTTGATGCTCAAGCACCTCAAGGACATGGATTCTCATTGCTCCTCCGCCGTCGGAAACGGA
      ·T  D  D  V  N  D  L  M  D  K  T  R  N  L  M  L  K  H  L  K  D  M  D  S  H  C  S  S  A  V  G  N  G

901  TCTCTGCCTCTCGACGCCGACATTGCAAAGTCAACGGCTACATCGATCGGAAACACAGACGATGCTGTCACAAAGAGGAGGACACTGAAAGAGTAAAACA
         S  L  P  L  D  A  D  I  A  K  S  T  A  T  S  I  G  N  T  D  D  A  V  T  K  R  R  T  L  K  E

1001  GCAACAACCACAAACACAACCATAACCACAACCACAACCACCCTGCAGGATACTCCGATCCAGCATATCGCATCCAAATGCCTGTAATGTACTTTTTTTT
1101  CTTTAAAAACATGATTAAATCGATAGAGCTGTACCCATTNGACAAGAA
```

Figure 4

```
         1                                                                                                  100
LPAAT3   ATGTCATCAATGTCATCAATAGA_____GTT____G_AAC_____TC___TTG_TT_____----_____AC_____
LPAAT4   ----------------------AT___AT_GGC__T___TAA__GT_T_CTA__GGA_CGAT__CCT_CG____TTT_T_TC__C_T_CA__T_C_

101                                                                                                200
LPAAT3   
LPAAT4

201                                                                                                300
LPAAT3   
LPAAT4

301                                                                                                400
LPAAT3   
LPAAT4

401                                                                                                500
LPAAT3   
LPAAT4

501                                                                                                600
LPAAT3   
LPAAT4

601                                                                                                700
LPAAT3   
LPAAT4

701                                                                                                800
LPAAT3   
LPAAT4

801                                                                                                900
LPAAT3   
LPAAT4

901                                                                                                999
LPAAT3   G__C_CG__CT__AGCA__GG_GA__T___CT__G__GGTGG__G___AC___G__TT_GCT_CGACAGCGTGAAGAAGAGGAAGACGGTCAAGGCTTAG
LPAAT4   A__G_TA__TC__TC--__GAAA_AC_____--__GT__C----__CA__AG__GA__AC__CTG_--------------------------------
```

Figure 5

```
        1                                                                                                    100
LPAAT3  MSMSSIEPASSFEGNLAVILFYLAPRLZAVEPQKIBFIAKGLIVITATFLMSVAGFVALVCAGHQKRALNYVAKIESYIACRPDGVTFNEVGE
LPAAT4  MSIGSSNPVLHAAIE------FRYLFVPERIVAFLRQKASELAKGIVVLIATLIMSVAGGLISEVCAMDKRYVENTVNSRLESFLAAPCGVTYKLVGE 101                                                                                                  200
LPAAT3  EHGENTPAPAVGNHQSSMDMVLCGRVEEMREVVMAKKELQYFPELGIEVTRSNATEFLDRKNILKKATESTFQAVADMKKHTNSGITLEPEGTRSRLDTADHL
LPAAT4  EHLDKYPAPVGNHQSSMDMMVLGRVEPKHGVVMAKKEDLMPPRLGMEMKESNATEFLDRGNIERKATESTLQAVADMKKHINSGLVAEPEGTRSRLDKADLL 201                                                                                                  300
LPAAT3  PFKKGAPHLAFSGGPFPAVAAAVNFLYDSAKISFLGGELEPRVLEPIPYTQMEADDVNDLMERTPAVILKNEKELDVNSLAVSSKPSLSVDELKNAPA
LPAAT4  PFKKQAFHLSLKQAQFPLEVASQGYSRLYDSSKHYFPGELEPAVLEPIPVKQLLTQDVNDIENDKIRNLMLKHFADMISHCSSAVGNG--------SLFL 301           330
LPAAT3  LKQEFKSTAVVEEEDVSYISPKSNKFVRA-
LPAAT4  DADIAKSARTS--IRNTDQAKTKRRLNE-
```

Figure 6

```
              1                                                                                                    100
    LPAAT3    MSSMSSIEPALSSFPGNLAVILVFYLALPRLLAVLPQKIQFIAKCLIVLTATFLMSVAGCFVAIVCALLQ-KRYAINYVVARIFSYIACRPCGVTFNIVG
    LPAAT4    MSIGSSNPVLLAAIP------FVYLFVLPRILAFLPQKAQFLAKCIVVLIATLIMSVAGCLISIVCALLD-KRYVINYVVSRLFSFLAARPCGVTYKIVG
gi_46101966   MAVLSKSFSTLTAGA------LLLLA----LISPRSQKLRFYLNSIIYIAGLGICSVWGIFVSILLSLVPGQRLNINKVVARSFWRLTSPLVGIRFIVEG
 gi_5002178   ---MSLLYYIASGAS-----TYIAFTASLFLVGQKVPRASFVARCLASYGSLLVCAMYGVVASIVLRVVG-YGRISQWATARSFKWVMRFTTGVRFDIVE
 gi_6320151   -------------------------------MSVIGRFLYYLRSVLVVLALAGCGFYGVIASILCTLIG-KQHLAQWITARCFYVMKLMLGLDVKVVG
gi_19115517   ---MGFIKSTLLATVT-----VFVGLCGINRFFTLPKCIRYHFRYFACHTFLAISSAYGVIASVVARLCG-YPVMGQYLTAKAYYGLASTILDFRFKIEN
gi_17564032   --------------MENFWSIVVFFLLSILFILYNISTVCHYYMRISFYYFTILLHGMEVCVTMIPSWLNG---KGADYVFHSFFYWCK--WTGVHTTVYG 101                                                                                                200
    LPAAT3    EEHLENT-PAIVVC  SSM MMVLGRVFPMRCVVMA KE QYF FLGIFMTL NAI ID KNHKKAIESTTQAVADNKKHNSGIWI P   SRLDTAD
    LPAAT4    EEHLDKY-PAIVVC  SSM MMVLGRVFPKHCVVMA KE LYF FLGMFMKL NAI ID KNHKKAIESTTQAVADNKKHNSGIWI P   SRLDKAD
gi_46101966   EEHFQAARPAVVVC  TAM ILYLGRIFPCNASIMA KE QFA LLGQFMSL GAVF IN KNLKDSIKAFQQVGETNNNKKLSLWI P   SGLATPD
 gi_5002178   GKEYLSTRPAVIIG  SEL VLMLGEIFPPYCSVTA KS RYV FLGWFMAL RTVB ID ANRQTAVKAFDSAAEEMRSHRQSVFI A   SYSEKPE
 gi_6320151   EENLAKK-PYIMIA  STL IFMLGRIFPPGCTVTA KS KYV FLGWFMAL GTY LD SKRQEAIDTLNKGLENVKKNKRALWV P   SYTSELT
gi_19115517   EEILRKHKSAVLVV  SEL ILAIGRTEGPNYSVIA KS RYV ILGWFMIL DVV ID SRRSDAIQLFAKAARRMRKENISIN V   SYSLKPC
gi_17564032   YEKTQVEGPAVVIC  SSL ILSMASIWPKNCVVMM RI AYV FFNLGAYF NTI ID YNRERAMASVDYCASEMKNRNLKLWV P   NR- EGG
                                *   *

201                                                                                                300
    LPAAT3    ELLF     HLI GSGL IL IYSAGYNH IYDSA-KRSFPG ELEIRV EP P TGM ADDVNDLMERTRAV LKNLKEMDVNSLAVSSKPSLSVDELKS
    LPAAT4    LL       IL IQAQL IL IVSQGYSH IYDSS-KRYFPG ELEIRV EP   KGL TDDVNDLMDKTRNL LKHLKDMDSHCSSAVGNG--------S
gi_46101966   LL       L  IQAGV VV VVCENYNRLFDS--RSRFES TIRIKV AP P KHL AADANELTEKVRQL LDELRNMDAERQRTDTAASVNNDEASM
 gi_5002178   LL       L  VKAGV IV VVVENYSH ILAPK-KFREEA SIKVKV PPI S DGL AADVDGLTTSTRES LNTLLELSNAGPADLPSS---------
 gi_6320151   ML       L  QQGKI IV YVSNTSTLVSPK-YGVFNR CMIVRI KP S ENL KDK IGEFAEKVRDQ VDTLKEIGYSPAINDTTLPPQAIEYAA
gi_19115517   LL       HL VQAQV II IAIQTY CHLFHPP-TKVFNK EALIKV DP P EGK AEDVNDLLHETETA NNALVEIDDYGKVKKQ-----------
gi_17564032   FI       NI VRAQI II VVFSDY RDFYSKPGRYFKND EVVIRV DA P KGL LDDVSELSDMCRDV AAYKEVTLEAQQRNATR---------

301                  355
    LPAAT3    APALKQEAKSTAVVEEEGVSYDSVKKR-KTVKA---------------------
    LPAAT4    LPLDADIAKSTATS--IGNTDDAVTKR-RTLKE---------------------
gi_46101966   AGVAGFFSKFVGTANSWQSVNSNVDKQEKRLRQNGTTGENPEDYHLVSEAQKKSN
 gi_5002178   ------S-KGQSTAVDL-------------------------------------
 gi_6320151   LQHDKKVNKKIKNEPVPSVSISNDVNTHNEGSSVKKMH----------------
gi_19115517   ------------------------------------------------------
gi_17564032   ----RGETKDGKKSE---------------------------------------
```

LYSOPHOSPHATIDIC ACID ACYLTRANSFERASE GENES

TECHNICAL FIELD

The present application claims priority to Japanese Patent Application Nos. 2007-139046 (filed on May 25, 2007) and 2007-323965 (filed on Dec. 14, 2007).

The present invention relates to novel genes for lysophosphatidic acid acyltransferase.

BACKGROUND ART

Fatty acids are important components of lipids such as phospholipids and triacylglycerols. Fatty acids containing two or more unsaturated bonds are collectively referred to as polyunsaturated fatty acids (PUFA) and are known to include arachidonic acid, dihomo-γ-linolenic acid, eicosapentaenoic acid and docosahexaenoic acid. Various physiological activities have been reported for these fatty acids (Non-patent Document 1).

Among them, arachidonic acid receives attention as an intermediate metabolite convertible into prostaglandin, leukotriene and so on, and many attempts have been made to apply arachidonic acid as a material for functional foods and pharmaceuticals. Moreover, arachidonic acid is found in mother's milk and is important for infant growth, particularly for height and brain development in fetuses. For this reason, arachidonic acid also receives attention as an ingredient necessary for infant growth from the nutritional point of view, as in the case of DHA (docosahexaenoic acid).

These polyunsaturated fatty acids are expected to have applications in various fields, but some of them cannot be synthesized in the animal body. Thus, microbial techniques have been developed for obtaining polyunsaturated fatty acids by culturing various microorganisms. Other attempts have also been made to produce polyunsaturated fatty acids in plants. In these cases, polyunsaturated fatty acids are known to be accumulated, for example, as components of storage lipids such as triacylglycerols within microorganism cells or plant seeds.

More specifically, triacylglycerols are produced in vivo as follows. Namely, glycerol-3-phosphate is acylated by glycerol-3-phosphate acyltransferase to form lysophosphatidic acid, which is then acylated further by lysophosphatidic acid acyltransferase to form phosphatidic acid. This phosphatidic acid is, in turn, dephosphorylated by phosphatidic acid phosphatase to form diacylglycerol, which is then acylated by diacylglycerol acyltransferase to form triacylglycerol. Other enzymes such as acylCoA:cholesterol acyltransferase and lysophosphatidylcholine acyltransferase are also known to be indirectly involved in biosynthesis of triacylglycerols.

As described above, the reaction in which lysophosphatidic acid (hereinafter also referred to as "LPA" or "1-acylglycerol-3-phosphate") is acylated to generate phosphatidic acid (hereinafter also referred to as "PA" or "1,2-diacyl-sn-glycerol-3-phosphate") is known to be mediated by lysophosphatidic acid acyltransferase (hereinafter also referred to as "LPAAT").

This LPAAT is also known as 1-acylglycerol-3-phosphate acyltransferase (E.C. 2.3.1.51). LPAAT genes have been reported so far in several organisms. As an LPAAT gene from *Escherichia coli*, the plsC gene has been cloned (Non-patent Document 2). In fungi, the SLC1 gene from *Saccharomyces cerevisiae* has been cloned (Non-patent Document 3). Likewise, LPAAT genes have also been cloned from animals and plants (Patent Document 1).

With respect to LPAAT in a lipid-producing fungus, *Mortierella alpina* (hereinafter also referred to as "*M. alpina*"), there is a report showing that the microsomal fraction of this fungus has the activity of lysophosphatidic acid acyltransferase (Non-patent Document 4). Moreover, two homologs have been reported for the LPAAT gene from *M. alpina* (Patent Documents 2 and 3).

Patent Document 1: International Patent Publication No. WO2004/076617
Patent Document 2: US Patent Publication No. 2006/174376
Patent Document 3: US Patent Publication No. 2006/0094090
Non-patent Document 1: Lipids, 39, 1147 (2004)
Non-patent Document 2: Mol. Gen. Genet., 232, 295-303, 1992
Non-patent Document 3: J.B.C., 268, 22156-22163, 1993
Non-patent Document 4: Biochemical Society Transactions, 28, 707-709, 2000
Non-patent Document 5: J. Bacteriology, 180, 1425-1430, 1998
Non-patent Document 6: J. Bacteriology, 173, 2026-2034, 1991

DISCLOSURE OF THE INVENTION

Problems to be Solved by the Invention

However, even if LPAAT genes previously reported are introduced into and expressed in host cells, fatty acid compositions produced by the hosts are limited due to the substrate specificity of the expressed enzymes. For this reason, there is a need to identify a novel gene which allows production of a fatty acid composition whose fatty acid rate differs from that previously reported. In particular, there is a need to identify a gene for a protein which allows production of a fatty acid composition rich in valuable fatty acids.

Means for Solving the Problems

The object of the present invention is to provide a protein or nucleic acid which allows production of fats and oils with a desired fatty acid rate and/or enrichment of desired fatty acids by being expressed in or introduced into host cells.

To achieve the above object, the inventors of the present invention have made extensive and intensive efforts. First, EST analysis was performed on a lipid-producing fungus, *Mortierella alpina*, to extract sequences sharing high identity with known LPAAT genes. To obtain the entire open reading frame (ORF) encoding LPAAT, genes were further cloned by cDNA library screening or PCR. As a result of attempting to introduce these genes into highly proliferative host cells (e.g., yeast cells) to thereby produce a desired fatty acid composition, the inventors succeeded in cloning a gene related to a novel LPAAT with different substrate specificity, which allows production of a fatty acid composition different from those produced by hosts expressing conventional LPAATs and which ensures a higher arachidonic acid content in host cells when compared to host cells which are not transformed with the gene. This led to the completion of the present invention. Namely, the present invention is as follows.

(1) A nucleic acid comprising a nucleotide sequence shown in any one of (a) to (e) below:
(a) a nucleotide sequence which encodes a protein consisting of an amino acid sequence with deletion, substitution or addition of one or more amino acids in the amino acid sequence shown in SEQ ID NO: 2 or 4 and having lysophosphatidic acid acyltransferase activity;

(b) a nucleotide sequence which is hybridizable under stringent conditions with a nucleic acid consisting of a nucleotide sequence complementary to a nucleotide sequence consisting of SEQ ID NO: 36 or 37 and which encodes a protein having lysophosphatidic acid acyltransferase activity;
(c) a nucleotide sequence which consists of a nucleotide sequence sharing an identity of 67% or more with a nucleotide sequence consisting of SEQ ID NO: 36 or 37 and which encodes a protein having lysophatidic acid acyltransferase activity;
(d) a nucleotide sequence which encodes an amino acid sequence sharing an identity of 69% or more with an amino acid sequence consisting of SEQ ID NO: 2 or 4 and which encodes a protein having lysophosphatidic acid acyltransferase activity; or
(e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes a protein having lysophosphatidic acid acyltransferase activity.

(2) The nucleic acid according to (1) above, which comprises a nucleotide sequence shown in any one of (a) to (c) below:
(a) a nucleotide sequence which encodes a protein consisting of an amino acid sequence with deletion, substitution or addition of 1 to 10 amino acids in the amino acid sequence shown in SEQ ID NO: 2 or 4 and having lysophosphatidic acid acyltransferase activity;
(b) a nucleotide sequence which is hybridizable under conditions of 2×SSC at 50° C. with a nucleic acid consisting of a nucleotide sequence complementary to a nucleotide sequence consisting of SEQ ID NO: 36 or 37 and which encodes a protein having lysophosphatidic acid acyltransferase activity; or
(c) a nucleotide sequence which encodes an amino acid sequence sharing an identity of 90% or more with an amino acid sequence consisting of SEQ ID NO: 2 or 4 and which encodes a protein having lysophosphatidic acid acyltransferase activity.

(3) A nucleic acid comprising a nucleotide sequence shown in any one of (a) to (c) below or a fragment thereof:
(a) the nucleotide sequence shown in SEQ ID NO: 36 or 37;
(b) a nucleotide sequence encoding a protein consisting of the amino acid sequence shown in SEQ ID NO: 2 or 4; or
(c) the nucleotide sequence shown in SEQ ID NO: 1 or 3.

(4) A nucleic acid comprising a nucleotide sequence shown in any one of (a) to (e) below:
(a) a nucleotide sequence which encodes the following protein:
a protein which consists of an amino acid sequence with deletion, substitution or addition of one or more amino acids in the amino acid sequence shown in SEQ ID NO: 2 or 4 and which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content;
(b) a nucleotide sequence which is hybridizable under stringent conditions with a nucleic acid consisting of a nucleotide sequence complementary to a nucleotide sequence consisting of SEQ ID NO: 36 or 37 and which encodes the following protein:
a protein which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content;
(c) a nucleotide sequence which consists of a nucleotide sequence sharing an identity of 67% or more with a nucleotide sequence consisting of SEQ ID NO: 36 or 37 and which encodes the following protein:
a protein which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content;
(d) a nucleotide sequence which encodes the following protein:
a protein which consists of an amino acid sequence sharing an identity of 69% or more with an amino acid sequence consisting of SEQ ID NO: 2 or 4 and which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content; or
(e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes the following protein:
a protein which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content.

(5) The nucleic acid according to (4) above, which comprises a nucleotide sequence shown in any one of (a) to (c) below:
(a) a nucleotide sequence which encodes the following protein:
a protein which consists of an amino acid sequence with deletion, substitution or addition of 1 to 10 amino acids in the amino acid sequence shown in SEQ ID NO: 2 or 4 and which has the ability to yield a fatty acid rate ensuring a higher ratio of at least one or more of i) to iv) shown below in the fatty acid rate of a host expressing the protein than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content;
(b) a nucleotide sequence which is hybridizable under conditions of 2×SSC at 50° C. with a nucleic acid consisting of a nucleotide sequence complementary to a nucleotide sequence consisting of SEQ ID NO: 36 or 37 and which encodes the following protein:
  a protein which has the ability to yield a fatty acid rate ensuring a higher ratio of at least one or more of i) to iv) shown below in the fatty acid rate of a host expressing the protein than in the fatty acid rate of a host not expressing the protein:
    i) the oleic acid content;
    ii) the ratio of the palmitoleic acid content to the palmitic acid content;
    iii) the ratio of the oleic acid content to the palmitic acid content; and
    iv) the ratio of the total content of stearic acid and oleic acid to the palmitic acid content; or
(c) a nucleotide sequence which encodes the following protein:
  a protein which consists of an amino acid sequence sharing an identity of 90% or more with an amino acid sequence consisting of SEQ ID NO: 2 or 4 and which has the ability to yield a fatty acid rate ensuring a higher ratio of at least one or more of i) to iv) shown below in the fatty acid rate of a host expressing the protein than in the fatty acid rate of a host not expressing the protein:
    i) the oleic acid content;
    ii) the ratio of the palmitoleic acid content to the palmitic acid content;
    iii) the ratio of the oleic acid content to the palmitic acid content; and
    iv) the ratio of the total content of stearic acid and oleic acid to the palmitic acid content.

(6) A nucleic acid comprising a nucleotide sequence shown in any one of (a) to (e) below:
(a) a nucleotide sequence which encodes the following protein:
  a protein which consists of an amino acid sequence with deletion, substitution or addition of one or more amino acids in the amino acid sequence shown in SEQ ID NO: 2 or 4 and which has the ability to ensure a higher arachidonic acid content in host cells expressing a protein comprising the amino acid sequence than in host cells not expressing the protein;
(b) a nucleotide sequence which is hybridizable under stringent conditions with a nucleic acid consisting of a nucleotide sequence complementary to a nucleotide sequence consisting of SEQ ID NO: 36 or 37 and which encodes a protein having the ability to ensure a higher arachidonic acid content in host cells expressing a protein encoded by the nucleotide sequence than in host cells not expressing the protein;
(c) a nucleotide sequence which consists of a nucleotide sequence sharing an identity of 67% or more with a nucleotide sequence consisting of SEQ ID NO: 36 or 37 and which encodes a protein having the ability to ensure a higher arachidonic acid content in host cells expressing a protein encoded by the nucleotide sequence than in host cells not expressing the protein;
(d) a nucleotide sequence which encodes the following protein:
  a protein which consists of an amino acid sequence sharing an identity of 69% or more with an amino acid sequence consisting of SEQ ID NO: 2 or 4 and which has the ability to ensure a higher arachidonic acid content in host cells expressing a protein comprising the amino acid sequence than in host cells not expressing the protein; or
(e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes a protein having the ability to ensure a higher arachidonic acid content in host cells expressing the protein than in host cells not expressing the protein.

(7) The nucleic acid according to (6) above, which comprises a nucleotide sequence shown in any one of (a) to (c) below:
(a) a nucleotide sequence which encodes a protein consisting of an amino acid sequence with deletion, substitution or addition of 1 to 10 amino acids in the amino acid sequence shown in SEQ ID NO: 2 or 4 and having the ability to ensure a higher arachidonic acid content in host cells expressing a protein comprising the amino acid sequence than in host cells not expressing the protein;
(b) a nucleotide sequence which is hybridizable under conditions of 2×SSC at 50° C. with a nucleic acid consisting of a nucleotide sequence complementary to a nucleotide sequence consisting of SEQ ID NO: 36 or 37 and which encodes a protein having the ability to ensure a higher arachidonic acid content in host cells expressing a protein encoded by the nucleotide sequence than in host cells not expressing the protein; or
(c) a nucleotide sequence which encodes an amino acid sequence sharing an identity of 90% or more with an amino acid sequence consisting of SEQ ID NO: 2 or 4 and which encodes a protein having the ability to ensure a higher arachidonic acid content in host cells expressing a protein comprising the amino acid sequence than in host cells not expressing the protein.

(8) A protein shown in (a) or (b) below:
(a) a protein which consists of an amino acid sequence with deletion, substitution or addition of one or more amino acids in SEQ ID NO: 2 or 4 and which has lysophosphatidic acid acyltransferase activity; or
(b) a protein which consists of an amino acid sequence sharing an identity of 69% or more with an amino acid sequence consisting of SEQ ID NO: 2 or 4 and which has lysophosphatidic acid acyltransferase activity.

(9) A protein shown in (a) or (b) below:
(a) a protein which consists of an amino acid sequence with deletion, substitution or addition of one or more amino acids in SEQ ID NO: 2 or 4 and which has the ability to yield a fatty acid rate ensuring a higher ratio of at least one or more of i) to iv) shown below in the fatty acid rate of a host expressing a protein consisting of the amino acid sequence than in the fatty acid rate of a host not expressing the protein:
  i) the oleic acid content;
  ii) the ratio of the palmitoleic acid content to the palmitic acid content;
  iii) the ratio of the oleic acid content to the palmitic acid content; and
  iv) the ratio of the total content of stearic acid and oleic acid to the palmitic acid content; or
(b) a protein which consists of an amino acid sequence sharing an identity of 69% or more with an amino acid sequence consisting of SEQ ID NO: 2 or 4 and which has the ability to yield a fatty acid rate ensuring a higher ratio of at least one or more of i) to iv) shown below in the fatty acid rate of a host expressing a protein consisting of the amino acid sequence than in the fatty acid rate of a host not expressing the protein:
 i) the oleic acid content;
 ii) the ratio of the palmitoleic acid content to the palmitic acid content;
 iii) the ratio of the oleic acid content to the palmitic acid content; and
 iv) the ratio of the total content of stearic acid and oleic acid to the palmitic acid content.
 (10) A protein shown in (a) or (b) below:
 (a) a protein which consists of an amino acid sequence with deletion, substitution or addition of one or more amino acids in SEQ ID NO: 2 or 4 and which has the ability to ensure a higher arachidonic acid content in host cells expressing a protein consisting of the amino acid sequence than in host cells not expressing the protein; or
 (b) a protein which consists of an amino acid sequence sharing an identity of 69% or more with an amino acid sequence consisting of SEQ ID NO: 2 or 4 and which has the ability to ensure a higher arachidonic acid content in host cells expressing a protein consisting of the amino acid sequence than in host cells not expressing the protein.
 (11) A protein consisting of the amino acid sequence shown in SEQ ID NO: 2 or 4.
 (12) A recombinant vector comprising the nucleic acid according to any one of (1) to (7) above.
 (13) A transformant transformed with the recombinant vector according to (12) above.
 (14) A fatty acid composition obtained by culturing the transformant according to (13) above, wherein at least one or more of i) to iv) shown below is higher in the fatty acid rate of the fatty acid composition than in a cultured product obtained by culturing a host which is not transformed with the recombinant vector according to (12) above:
 i) the oleic acid content;
 ii) the ratio of the palmitoleic acid content to the palmitic acid content;
 iii) the ratio of the oleic acid content to the palmitic acid content; and
 iv) the ratio of the total content of stearic acid and oleic acid to the palmitic acid content.
 (15) A fatty acid composition obtained by culturing the transformant according to (13) above, wherein the arachidonic acid content in the fatty acid composition is higher than that of a cultured product obtained by culturing a host which is not transformed with the recombinant vector according to (12) above.
 (16) A method for preparing a fatty acid composition, which comprises collecting the fatty acid composition according to (14) or (15) above from a cultured product obtained by culturing the transformant according to (13) above.
 (17) A food product comprising the fatty acid composition according to (14) or (15) above.

Advantages of the Invention

The LPAAT of the present invention has substrate specificity different from that of conventional LPAATs, and allows a host to produce a fatty acid composition whose fatty acid rate differs from that of fatty acid compositions produced by hosts expressing conventional LPAATs. As a result, the LPAAT of the present invention enables the provision of lipids having desired properties and effects, and is useful as being applicable to foods, cosmetics, pharmaceuticals, soaps, etc.

The arachidonic acid content in host cells expressing the LPAAT of the present invention is higher than that of host cells not expressing the LPAAT of the present invention. A fatty acid composition obtained from a cultured product of these LPAAT-expressing cells is expected to provide a nutritionally higher effect and hence is preferred.

Moreover, the LPAAT of the present invention allows improvement in the ability to produce fatty acids and storage lipids, and hence is preferred as a means for improving the productivity of polyunsaturated fatty acids in microorganisms and plants.

BRIEF DESCRIPTION OF THE DRAWINGS

FIG. 2 shows the cDNA sequence of LPAAT3 (SEQ ID NO: 1) according to the present invention, along with its deduced amino acid sequence (SEQ ID NO: 2).

FIG. 3 shows the cDNA sequence of LPAAT4 (SEQ ID NO: 3), along with its deduced amino acid sequence (SEQ ID NO: 4).

FIG. 4 shows a comparison of DNA sequences between CDS regions of LPAAT3 (SEQ ID NO: 8) and LPAAT4 (Nucleotides 1-934 of SEQ ID NO: 37).

FIG. 5 shows a comparison of deduced amino acid sequences between LPAAT3 (SEQ ID NO: 2) and LPAAT4 (SEQ ID NO: 4).

FIG. 6 shows the deduced amino acid sequences of LPAAT3p (SEQ ID NO: 2) and LPAAT4p (SEQ ID NO: 4) in comparison with known amino acid sequences (SEQ ID NOS 40-44, respectively, in order of appearance).

BEST MODE FOR CARRYING OUT THE INVENTION

Figure 1:
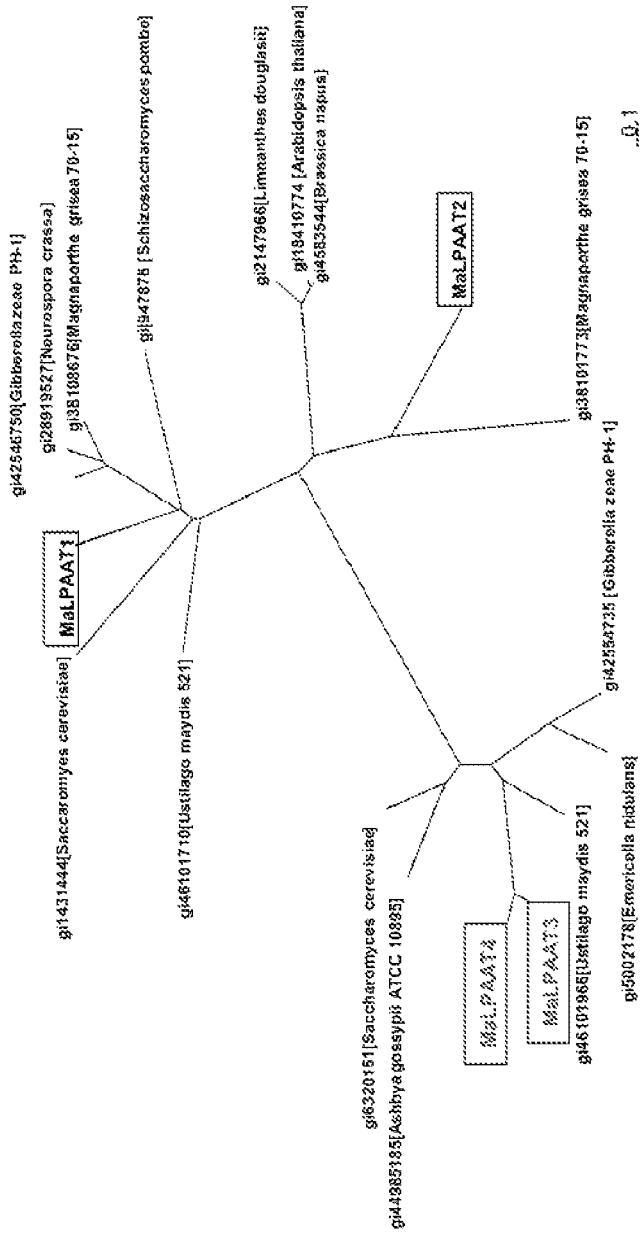
FIG. 1 is a dendrogram showing the relationship between two homologs LPAAT3 and LPAAT4 according to the present invention and known homologs LPAAT1 and LPAAT2.

The present invention relates to novel genes for lysophosphatidic acid acyltransferase derived from the genus *Mortierella*, characterized by acylating lysophosphatidic acid to generate phosphatidic acid.

Lysophosphatidic acid acyltransferase (LPAAT) in the present invention is an enzyme that catalyzes a reaction in which lysophosphatidic acid is acylated to generate phosphatidic acid. An acyl donor is generally acylCoA, but is not limited thereto. An acyl acceptor in the acyl transfer reaction catalyzed by the protein of the present invention is not limited to LPA, and various lysophospholipids may serve as acyl acceptors.

LPA (hereinafter also referred to as "1-acyl-sn-glycerol-3-phosphate") according to the present invention is a kind of glycerophospholipid. LPA is a lysophospholipid having only one fatty acid, which is produced by acylation of the hydroxyl group at the 1-position (α-position) of glycerol-3-phosphate (hereinafter also referred to as "sn-glycerol-3-phosphate"). LPA is not only an intermediate for lipid biosynthesis, but also serves as an intracellular and intercellular lipid mediator having a very wide range of biological and pharmacological effects including cell proliferation, platelet aggregation, contraction of smooth muscle, and promotion of cancer invasion.

Nucleic Acids of the Present Invention Encoding Lysophosphatidic Acid Acyltransferase Lysophosphatidic acid acyltransferase (LPAAT) in the present invention encompasses LPAAT3 and LPAAT4. The correspondence between nucleic acids encoding LPAAT3 and LPAAT4 are summarized according to their cDNA, CDS, ORF and amino acid sequences in Table 1 below.

TABLE 1

| | LPAAT3 | | LPAAT4 | |
|---|---|---|---|---|
| | SEQ ID NO | Corresponding region in SEQ ID NO: 1 | SEQ ID NO | Corresponding region In SEQ ID NO: 3 |
| cDNA | SEQ ID NO: 1 | ***** | SEQ ID NO: 3 | ***** |
| CDS | SEQ ID NO: 8 | Positions 158-1147 | SEQ ID NO: 23 | Positions 55-996 |
| ORF | SEQ ID NO: 36 | Positions 158-1144 | SEQ ID NO: 37 | Positions 55-993 |
| Amino acid sequence | SEQ ID NO: 2 | ***** | SEQ ID NO: 4 | ***** |

Namely, sequences related to LPAAT3 of the present invention include SEQ ID NO: 2 (amino acid sequence of LPAAT3), SEQ ID NO: 36 (sequence representing the ORF region of LPAAT3), SEQ ID NO: 8 (sequence representing the CDS region of LPAAT3) and SEQ ID NO: 1 (nucleotide sequence of cDNA for LPAAT3). Among them, SEQ ID NO: 8 corresponds to nucleotides 158-1147 of SEQ ID NO: 1, while SEQ ID NO: 36 corresponds to nucleotides 158-1144 of SEQ ID NO: 1 or nucleotides 1-987 of SEQ ID NO: 8.

Likewise, sequences related to LPAAT4 include SEQ ID NO: 4 (amino acid sequence of LPAAT4), SEQ ID NO: 37 (sequence representing the ORF region of LPAAT4), SEQ ID NO: 23 (sequence representing the CDS region of LPAAT4) and SEQ ID NO: 3 (nucleotide sequence of cDNA for LPAAT4). Among them, SEQ ID NO: 23 corresponds to nucleotides 55-996 of SEQ ID NO: 3, while SEQ ID NO: 37 corresponds to nucleotides 55-993 of SEQ ID NO: 3 or nucleotides 1-939 of SEQ ID NO: 23.

The nucleic acids of the present invention encompass single-stranded and double-stranded DNAs as well as complementary RNAs thereof, which may be either naturally occurring or artificially prepared. DNAs include, but are not limited to, genomic DNAs, cDNAs corresponding to the genomic DNAs, chemically synthesized DNAs, PCR-amplified DNAs, as well as combinations thereof and DNA/RNA hybrids.

Preferred embodiments for the nucleic acids of the present invention include (a) the nucleotide sequence shown in SEQ ID NO: 36 or 37, (b) a nucleotide sequence encoding a protein consisting of the amino acid sequence shown in SEQ ID NO: 2 or 4, and (c) the nucleotide sequence shown in SEQ ID NO: 1 or 3.

The above nucleotide sequence shown in SEQ ID NO: 36 or 37, nucleotide sequence encoding a protein consisting of the amino acid sequence shown in SEQ ID NO: 2 or 4, and nucleotide sequence shown in SEQ ID NO: 1 or 3 are as shown in Table 1.

To obtain these nucleotide sequences, nucleotide sequence data of ESTs or genomic DNAs from organisms having LPAAT activity may be used to search a nucleotide sequence encoding a protein sharing high identity with known proteins having LPAAT activity. Preferred organisms having LPAAT activity are lipid-producing fungi including, but not limited to, M. alpina.

For EST analysis, a cDNA library is first prepared. As to techniques for cDNA library preparation, reference may be made to "Molecular Cloning, A Laboratory Manual 3rd ed." (Cold Spring Harbor Press (2001)). Alternatively, a commercially available cDNA library preparation kit may be used. Techniques for cDNA library preparation suitable for the present invention are as follows, by way of example. Namely, an appropriate strain of M. alpina, a lipid-producing fungus, is inoculated into an appropriate medium and pre-cultured for an appropriate period. Culture conditions suitable for this pre-culture include, for example, medium composition of 1.8% glucose, 1% yeast extract and pH 6.0, a culture period of 3 days, and a culture temperature of 28° C. The pre-cultured product is then subjected to main culture under appropriate conditions. Medium composition suitable for main culture may be, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$ and pH 6.0. Culture conditions suitable for main culture may be, for example, aerobic spinner culture at 300 rpm, 1 vvm, 26° C. for 8 days. An appropriate amount of glucose may be added during culture. The cultured product is sampled at appropriate time points during main culture, from which the cells are then collected to prepare total RNA. For preparation of total RNA, it is possible to use any known technique, such as guanidine hydrochloride/CsCl method. The resulting total RNA may be treated with a commercially available kit to purify poly(A)$^+$ RNA. Further, a cDNA library may be prepared with a commercially available kit. Then, any clone from the cDNA library thus prepared is determined for its nucleotide sequence by using primers which are designed on a vector to allow determination of the nucleotide sequence of an insert. As a result, ESTs can be obtained. For example, when a ZAP-cDNA GigapackIII Gold Cloning Kit (STRATAGENE) is used for cDNA library preparation, directional cloning can be performed.

The nucleotide sequence identity between ORFs of LPAAT3 and LPAAT4 is 66.6%. On the other hand, there are two known homologs LPAAT1 and LPAAT2 for M. alpina-derived LPAAT. The relationship between these two homologs and the two homologs of the present invention is shown in the dendrogram of FIG. 1. The ORF of LPAAT3 according to the present invention shares a nucleotide sequence identity of 34.3% and 47.0% with those of known LPAAT1 and LPAAT2, respectively, while the ORF of LPAAT4 shares a nucleotide sequence identity of 34.6% and 47.3% with those of known LPAAT1 and LPAAT2, respectively. As is apparent from FIG. 1, LPAAT3 and LPAAT4 of the present invention are considerably apart from known LPAATs in terms of evolutionary classification, and their functions are also different from those known. Namely, as will be explained later, LPAAT3 and LPAAT4 of the present invention have functions completely different from those of known LPAATs because they allow a host to produce a fatty acid composition whose fatty acid rate differs from that of fatty acid compositions produced by hosts expressing known LPAATs, and because the arachidonic acid content in host cells expressing these LPAATs of the present invention is higher than that of host cells not expressing the LPAATs of the present invention.

It should be noted that when analyzed by BLASTX, nucleotide sequences encoding LPAAT3 and LPAAT4 of the present invention share an identity of 49.2% and 51.3%, respectively, with a nucleotide sequence (GB accession No.

XM_757480) encoding a *Ustilago maydis* 521-derived putative protein (FIG. 1) (UM06426.1, GB accession No. EAK87199) having the lowest E-value.

Likewise, the amino acid sequence identity between LPAAT3 and LPAAT4 is 69.1%. LPAAT3 shares an amino acid sequence identity of 12.3% and 17.3% with known LPAAT1 and LPAAT2, respectively, while LPAAT4 shares an amino acid sequence identity of 12.5% and 15.5% with known LPAAT1 and LPAAT2, respectively. It should be noted that when analyzed by BLASTP, amino acid sequences of LPAAT3 and LPAAT4 of the present invention share an identity of 36.2% and 36.7%, respectively, with a *Ustilago maydis* 521-derived putative protein (FIG. 1) (UM06426.1, GB accession No. EAK87199) having the lowest E-value.

The present invention also encompasses nucleic acids functionally equivalent to a nucleic acid comprising the above nucleotide sequence shown in SEQ ID NO: 36 or 37 (hereinafter also referred to as "the nucleotide sequence of the present invention") or nucleotide sequence encoding a protein consisting of the amino acid sequence shown in SEQ ID NO: 2 or 4 (hereinafter also referred to as "the amino acid sequence of the present invention"). The phrase "functionally equivalent" is intended to mean that a protein encoded by the nucleotide sequence of the present invention or a protein consisting of the amino acid sequence of the present invention has LPAAT activity. LPAAT activity can be measured in a known manner, as exemplified below. Namely, a microsomal fraction is prepared from yeast cells transformed to express the LPAAT of the present invention, as described in, e.g., J. Bacteriology, 173, 2026-2034 (1991). To a reaction solution containing 0.44 mM LPA, 0.36 mM acyl-CoA, 0.5 mM DTT, 1 mg/ml BSA and 2 mM $MgCl_2$ in Tris-HCl (pH 7.5), the above microsomal fraction is then added and reacted at 28° C. for an appropriate period. Chloroform:methanol is added to stop the reaction, followed by lipid extraction. The resulting lipids are fractionated by thin-layer chromatography or other techniques, whereby the amount of PA generated by the above reaction can be quantified. As a result, a higher amount of generated PA can be indicative of a higher activity as LPAAT. For example, strains transformed to express LPAAT3 or LPAAT4 by this method have been found to increase the amount of linolic acid (18:2) incorporated into the PA fraction when linoleoyl-CoA is used as acyl-CoA in the above reaction. Thus, LPAAT3 and LPAAT4 can be regarded as having LPAAT activity.

In addition to this LPAAT activity, a protein encoded by the nucleotide sequence of the present invention or a protein consisting of the amino acid sequence of the present invention may have the ability to yield a fatty acid rate ensuring a higher ratio of at least one or more of:

i) the oleic acid content;
ii) the ratio of the palmitoleic acid content to the palmitic acid content;
iii) the ratio of the oleic acid content to the palmitic acid content; and
iv) the ratio of the total content of stearic acid and oleic acid to the palmitic acid content
in the fatty acid rate of a host expressing the protein than in the fatty acid rate of a host not expressing the protein (such a protein is hereinafter also referred to as a "protein having the ability to yield the fatty acid rate of LPAAT in the present invention").

A specific example is a nucleic acid comprising a nucleotide sequence encoding a protein having the ability to yield a fatty acid rate ensuring the following:

i) the oleic acid content is 52% or more;
ii) the ratio of the palmitoleic acid content to the palmitic acid content is 7.25 or more;
iii) the ratio of the oleic acid content to the palmitic acid content is 9.94 or more; and
iv) the ratio of the total content of stearic acid and oleic acid to the palmitic acid content is 10.72 or more, when the above nucleotide sequence of the present invention is inserted into expression vector pYE22m (Biosci. Biotech. Biochem., 59, 1221-1228, 1995) and transformed into a yeast host, *Saccharomyces cerevisiae* strain EH13-15 (Appl. Microbiol. Biotechnol., 30, 515-520, 1989), and the resulting transformant is cultured to collect the cells, which are then analyzed for fatty acids by the procedures described in Example 7 below. More preferred is a nucleic acid comprising a nucleotide sequence encoding a protein having both LPAAT activity and the above ability to yield the fatty acid rate of LPAAT in the present invention. It should be noted that these fatty acid rates may vary slightly when transformants are cultured under culture conditions different from those used in the above procedures of Example 7. Such culture conditions include, for example, temperature and culture period.

Within the scope of "functionally equivalent," in addition to LPAAT activity and the ability to yield the fatty acid rate of LPAAT in the present invention, a protein encoded by the nucleotide sequence of the present invention or a protein consisting of the amino acid sequence of the present invention may have the ability to ensure a higher arachidonic acid content in host cells expressing a protein encoded by the nucleotide sequence of the present invention or a protein consisting of the amino acid sequence of the present invention than in host cells not expressing the protein (such a protein is hereinafter also referred to as a "protein having the ability to increase the intracellular arachidonic acid content in the present invention").

Arachidonic acid will be explained in the section "Fatty acid compositions of the present invention" described later. As in the case above, such a nucleic acid is more specifically a nucleic acid comprising a nucleotide sequence encoding a protein having the ability to yield a fatty acid rate ensuring a higher intracellular arachidonic acid content than in a host not expressing the protein, when the nucleotide sequence of the present invention is inserted into expression vector pYE22m and transformed into an arachidonic acid-producing yeast host, strain ARA3-1, which is derived from yeast *Saccharomyces cerevisiae* strain YPH499 by introduction and expression of Δ12 fatty acid desaturase, Δ6 fatty acid desaturase, Δ6 fatty acid elongase and Δ5 fatty acid elongase, and the resulting transformant is cultured to collect the cells, which are then analyzed for fatty acids by the procedures described in Example 7 below. More preferred is a nucleic acid comprising a nucleotide sequence encoding a protein having both LPAAT activity and the ability to increase the intracellular arachidonic acid content in the present invention.

Such nucleic acids that are functionally equivalent to the nucleic acids of the present invention include a nucleic acid comprising a nucleotide sequence shown in any one of (a) to (e) below. It should be noted that when used to describe the nucleotide sequences listed below, the phrase "the above activity of the present invention" is intended to mean "LPAAT activity and/or the ability to yield the fatty acid rate of LPAAT in the present invention and/or the ability to increase the intracellular arachidonic acid content in the present invention" defined above.

(a) A nucleotide sequence which encodes a protein consisting of an amino acid sequence with deletion, substitution or addition of one or more amino acids in the amino acid sequence shown in SEQ ID NO: 2 or 4 and having the above activity of the present invention.

Nucleotide sequences contained in the nucleic acids of the present invention include a nucleotide sequence which encodes a protein consisting of an amino acid sequence with deletion, substitution or addition of one or more amino acids in the amino acid sequence shown in SEQ ID NO: 2 or 4 and having the above activity of the present invention.

More specifically, it is a nucleotide sequence which encodes a protein consisting of:

(i) an amino acid sequence with deletion of one or more (preferably one or several (e.g., 1-100, 1-50, 1-30, 1-25, 1-20, 1-15, 1-10, more preferably 1-5)) amino acids in the amino acid sequence shown in SEQ ID NO: 2 or 4;

(ii) an amino acid sequence with substitution of other amino acids for one or more (preferably one or several (e.g., 1-100, 1-50, 1-30, 1-25, 1-20, 1-15, 1-10, more preferably 1-5)) amino acids in the amino acid sequence shown in SEQ ID NO: 2 or 4;

(iii) an amino acid sequence with addition of other one or more (preferably one or several (e.g., 1-100, 1-50, 1-30, 1-25, 1-20, 1-15, 1-10, more preferably 1-5)) amino acids in the amino acid sequence shown in SEQ ID NO: 2 or 4; or (iv) an amino acid sequence with any combination of (i) to (iii) above, and having the above activity of the present invention.

Among the above modifications, substitution is preferably conservative, which means the replacement of a certain amino acid residue by another residue having similar physical and chemical characteristics. It may be any substitution as long as it does not substantially alter the structural characteristics of the original sequence. For example, any substitution is possible as long as the substituted amino acids do not disrupt a helix present in the original sequence or do not disrupt any other type of secondary structure characterizing the original sequence.

Conservative substitution is generally introduced by synthesis in biological systems or chemical peptide synthesis, preferably by chemical peptide synthesis. In this case, substituents may include unnatural amino acid residues, as well as peptidomimetics, and reversed or inverted forms of amino acid sequences in which unsubstituted regions are reversed or inverted.

Amino acid residues are classified and listed below in groups of mutually substitutable members, but are not limited to the following:

Group A: leucine, isoleucine, norleucine, valine, norvaline, alanine, 2-aminobutanoic acid, methionine, O-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and

Group G: phenylalanine and tyrosine.

Non-conservative substitution may involve the exchange of a member of one of the above classes for a member from another class. In this case, for the purpose of maintaining biological functions of the proteins of the present invention, it is preferable to consider the hydropathic index of amino acids (hydropathic amino acid index) (Kyte et al., J. Mol. Biol., 157:105-131 (1982)).

In the case of non-conservative substitution, amino acid substitutions may also be accomplished on the basis of hydrophilicity.

In the specification and drawings of the present application, nucleotides, amino acids and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomer, unless otherwise specified.

Stereoisomers (e.g., D-amino acids) of the above amino acids, unnatural amino acids such as α,α-disubstituted amino acids, N-alkylamino acids, lactic acid, and other unconventional amino acids may also be members constituting the proteins of the present invention.

It should be noted that in the protein notation used herein, the lefthand direction is the amino terminal direction and the righthand direction is the carboxy terminal direction, in accordance with standard usage and convention.

Similarly, unless otherwise specified, the lefthand end of single-stranded polynucleotide sequences is the 5'-end and the lefthand direction of double-stranded polynucleotide sequences is referred to as the 5' direction.

Those skilled in the art would be able to design and prepare appropriate mutants of the proteins described herein by using techniques known in the art. For example, when targeting a region which appears to be less important for the biological activity of the protein of the present invention, it is possible to identify a suitable region in the protein molecule whose structure can be changed without impairing the biological activity of the protein of the present invention. It is also possible to identify residues or regions in the molecule, which are conserved between similar proteins. Moreover, it is also possible to introduce conservative amino acid substitutions into a region which appears to be important for the biological activity or structure of the protein of the present invention, without impairing the biological activity and without adversely affecting the polypeptide structure of the protein. Particularly in the present invention, as double underlined in FIG. 6, the two LPAAT amino acid sequences of the present invention contain a consensus motif, "HXXXXD (HX$_4$D)" (conserved amino acid residues are indicated with *). This motif is essential for glycerolipid acyltransferase (J. Bacteriology, 180, 1425-1430, 1998) and is also important for the LPAATs of the present invention. Thus, mutants according to the present invention are not limited in any way as long as the above consensus motif is conserved and the above activity of the present invention is not impaired. In the above consensus motif, X represents any amino acid residue.

Those skilled in the art would be able to conduct a so-called structure-function study which identifies residues, in the protein of the present invention and in a similar peptide thereof, that are important for biological activity or structure, and compares amino acid residues between these two peptides, thereby predicting which residues in the protein similar to the protein of the present invention are amino acid residues corresponding to those important for biological activity or structure. Moreover, chemically similar amino acid substitutions may be chosen for the amino acid residues thus predicted to thereby select a mutant which retains the biological activity of the protein of the present invention. Likewise, those skilled in the art would also be able to analyze the three-dimensional structure and amino acid sequence of this protein mutant. The analysis results thus obtained can further be used to predict the alignment of amino acid residues with respect to the three-dimensional structure of the protein. Since amino acid residues predicted to be on the protein surface may be involved in important interactions with other molecules, those skilled in the art would be able to prepare a mutant which causes no change in these amino acid residues predicted to be on the protein surface, on the basis of analysis results as mentioned above. Moreover, those skilled in the art would also be able to prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention when a comparison is made with the following case where a mutant having substitution of a specific amino acid residue shows lower biological activity than that of the protein of the present invention, where such a mutant shows no biological activity, or where such a mutant produces unsuitable activity to inhibit the biological activity of the protein of the present invention. Moreover, based on information collected from such routine experiments, those skilled in the art may readily analyze amino acid substitutions undesirable for mutants of the protein of the present invention either alone or in combination with other mutations.

As described above, a protein consisting of an amino acid sequence with deletion, substitution or addition of one or more amino acids in the amino acid sequence shown in SEQ ID NO: 2 or 4 can be prepared according to techniques such as site-directed mutagenesis as described in "Molecular Cloning, A Laboratory Manual 3rd ed." (Cold Spring Harbor Press (2001)), "Current Protocols in Molecular Biology" (John Wiley & Sons (1987-1997), Kunkel (1985) Proc. Natl. Acad. Sci. USA 82: 488-92, and Kunkel (1988) Method. Enzymol. 85: 2763-6. Preparation of a Mutant with Such a Mutation Including Amino acid deletion, substitution or addition may be accomplished, for example, by known procedures such as Kunkel method or Gapped duplex method using a mutation-introducing kit based on site-directed mutagenesis such as a QuikChange™ Site-Directed Mutagenesis Kit (Stratagene), a GeneTailor™ Site-Directed Mutagenesis System (Invitrogen) or a TaKaRa Site-Directed Mutagenesis System (e.g., Mutan-K, Mutan-Super Express Km; Takara Bio Inc., Japan).

Techniques for allowing deletion, substitution or addition of one or more amino acids in the amino acid sequences of proteins while retaining their activity include site-directed mutagenesis mentioned above, as well as other techniques such as those for treating a gene with a mutagen, and those in which a gene is selectively cleaved to remove, substitute or add a selected nucleotide or nucleotides, and then ligated.

A preferred nucleotide sequence contained in the nucleic acids of the present invention is a nucleotide sequence which encodes a protein consisting of an amino acid sequence with deletion, substitution or addition of 1 to 10 amino acids in the amino acid sequence shown in SEQ ID NO: 2 or 4 and having LPAAT activity.

Moreover, nucleotide sequences contained in the nucleic acids of the present invention also include a nucleotide sequence which encodes a protein consisting of an amino acid sequence with deletion, substitution or addition of 1 to 10 amino acids in SEQ ID NO: 2 or 4 and having the above activity of the present invention.

There is no limitation on the number or sites of amino acid mutations or modifications in the protein of the present invention, as long as the resulting mutant retains LPAAT activity or the ability to yield the fatty acid rate of LPAAT in the present invention or the ability to increase the intracellular arachidonic acid content in the present invention.

LPAAT activity in the present invention or the ability to yield the fatty acid rate of LPAAT in the present invention or the ability to increase the intracellular arachidonic acid content in the present invention can be measured in a known manner. For example, reference may be made to the following document: J.B.C., 265, 17215-17221, 1990.

"LPAAT activity" in the present invention may be measured as follows, by way of example. A microsomal fraction is prepared from yeast cells transformed to express the LPAAT of the present invention, as described in, e.g., J. Bacteriology, 173, 2026-2034 (1991). To a reaction solution containing 0.44 mM LPA, 0.36 mM acyl-CoA, 0.5 mM DTT, 1 mg/ml BSA and 2 mM $MgCl_2$ in 50 mM Tris-HCl (pH 7.5), the above microsomal fraction is then added and reacted at 28° C. for an appropriate period. Chloroform:methanol is added to stop the reaction, followed by lipid extraction. The resulting lipids are fractionated by thin-layer chromatography or other techniques, whereby the amount of PA generated can be quantified.

Likewise, "the ability to yield the fatty acid rate of LPAAT" in the present invention may be measured as follows, by way of example. To lyophilized cells obtained by the method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography. Moreover, "the ability to increase the intracellular arachidonic acid content" in the present invention can also be measured by analyzing the content of arachidonic acid in the above manner.

(b) A nucleotide sequence which is hybridizable under stringent conditions with a nucleic acid consisting of a nucleotide sequence complementary to a nucleotide sequence consisting of SEQ ID NO: 36 or 37 and which encodes a protein having the above activity of the present invention.

Nucleotide sequences contained in the nucleic acids of the present invention include a nucleotide sequence which is hybridizable under stringent conditions with a nucleic acid consisting of a nucleotide sequence complementary to a nucleotide sequence consisting of SEQ ID NO: 36 or 37 and which encodes a protein having the above activity of the present invention. SEQ ID NO: 36 or 37 and LPAAT activity are as described above.

To obtain the above nucleotide sequence, a probe may be prepared from an appropriate fragment in a manner known to those skilled in the art, and this probe may be used in known hybridization techniques such as colony hybridization, plaque hybridization or Southern blotting to obtain the nucleotide sequence from a cDNA library, a genomic library or the like.

As to detailed procedures for hybridization techniques, reference may be made to "Molecular Cloning, A Laboratory Manual 3rd ed." (Cold Spring Harbor Press (2001); particularly Sections 6-7), "Current Protocols in Molecular Biology" (John Wiley & Sons (1987-1997); particularly Sections 6.3-6.4), "DNA Cloning 1: Core Techniques, A Practical Approach 2nd ed." (Oxford University (1995); particularly Section 2.10 for hybridization conditions).

The strength of hybridization is determined primarily by hybridization conditions, more preferably by hybridization conditions and washing conditions. The term "stringent conditions" as used herein is intended to include moderately or highly stringent conditions.

More specifically, moderately stringent conditions include, for example, hybridization conditions of 1×SSC to 6×SSC at 42° C. to 55° C., more preferably 1×SSC to 3×SSC at 45° C. to 50° C., and most preferably 2×SSC at 50° C. In certain cases such as where a hybridization solution contains about 50% formamide, a temperature which is 5° C. to 15° C. lower than the above temperature is used. Washing conditions may be 0.5×SSC to 6×SSC at 40° C. to 60° C. During hybridization and washing, 0.05% to 0.2% SDS, preferably about 0.1% SDS may usually be added.

Highly stringent (high stringent) conditions include hybridization and/or washing at higher temperature and/or lower salt concentration, compared to the moderately stringent conditions. For example, hybridization conditions may be 0.1×SSC to 2×SSC at 55° C. to 65° C., more preferably 0.1×SSC to 1×SSC at 60° C. to 65° C., and most preferably 0.2×SSC at 63° C. Washing conditions may be 0.2×SSC to 2×SSC at 50° C. to 68° C., and more preferably 0.2×SSC at 60° C. to 65° C.

Hybridization conditions particularly used in the present invention include, but are not limited to, prehybridization in 5×SSC, 1% SDS, 50 mM Tris-HCl (pH 7.5) and 50% formamide at 42° C., overnight incubation at 42° C. in the presence of a probe to form hybrids, and the subsequent three washings in 0.2×SSC, 0.1% SDS at 65° C. for 20 minutes.

It is also possible to use a commercially available hybridization kit which uses no radioactive substance as a probe. Specific examples include hybridization with a DIG nucleic acid detection kit (Roche Diagnostics) or with an ECL direct labeling & detection system (Amersham).

A preferred nucleotide sequence falling within the present invention is a nucleotide sequence which is hybridizable under conditions of 2×SSC at 50° C. with a nucleic acid consisting of a nucleotide sequence complementary to a nucleotide sequence consisting of SEQ ID NO: 36 or 37 and which encodes a protein having LPAAT activity.

(c) A nucleotide sequence which consists of a nucleotide sequence sharing an identity of 67% or more with a nucleotide sequence consisting of SEQ ID NO: 36 or 37 and which encodes a protein having the above activity of the present invention.

Nucleotide sequences contained in the nucleic acids of the present invention include a nucleotide sequence which consists of a nucleotide sequence being at least 67% or more of the nucleic acid sequence shown in SEQ ID NO: 36 or 37 and which encodes a protein having the above activity of the present invention.

Preferred examples include nucleic acids comprising a nucleotide sequence which shares an identity of at least 70%, more preferably 75%, even more preferably 80% (e.g., 85% or more, even more preferably 90% or more, more particularly 95%, 98% or 99%) with the nucleic acid sequence shown in SEQ ID NO: 36 or 37 and which encodes a protein having the above activity of the present invention. As described above, the identity between LPAAT3 (SEQ ID NO: 36) and LPAAT4 (SEQ ID NO: 37) is 66.6%. The nucleic acids of the present invention include those being at least 67% or more of the nucleic acid sequence shown in SEQ ID NO: 36 or 37 and being similar to these two sequences.

The percent identity between two nucleic acid sequences can be determined by visual inspection and mathematical calculation, or more preferably by using a computer program to compare sequence information between two nucleic acids. Computer programs for sequence comparison include, for example, the BLASTN program (Altschul et al. (1990) J. Mol. Biol. 215: 403-10) version 2.2.7, available for use via the National Library of Medicine website: http://www.ncbi.nlm.nih.gov/blast/bl2seq/bls.html, or the WU-BLAST 2.0 algorithm. Standard default parameter settings for WU-BLAST 2.0 are described at the following Internet site: http://blast.wustl.edu.

(d) A nucleotide sequence which encodes an amino acid sequence sharing an identity of 69% or more with an amino acid sequence consisting of SEQ ID NO: 2 or 4 and which encodes a protein having the above activity of the present invention.

Nucleotide sequences contained in the nucleic acids of the present invention include a nucleotide sequence which encodes an amino acid sequence sharing an identity of 69% or more with an amino acid sequence consisting of SEQ ID NO: 2 or 4 and which encodes a protein having the above activity of the present invention. Proteins encoded by the nucleic acids of the present invention may also be those sharing identity with the amino acid sequence of LPAAT3 or LPAAT4, as long as they are functionally equivalent to proteins having the above activity of the present invention.

Specific examples include amino acid sequences sharing an identity of 70% or more, preferably 75% or more, more preferably 80%, more preferably 85% or more, even more preferably 90% (e.g., 95%, more particularly 98%) with the amino acid sequence shown in SEQ ID NO: 2 or 4. As described above, the amino acid sequence identity between LPAAT3 (SEQ ID NO: 2) and LPAAT4 (SEQ ID NO: 4) is 69.1%. Proteins encoded by the nucleic acids of the present invention include those being at least 69% or more of the amino acid sequence shown in SEQ ID NO: 2 or 4 and being similar to these two sequences.

A preferred nucleotide sequence contained in the nucleic acids of the present invention is a nucleotide sequence which encodes an amino acid sequence sharing an identity of 90% or more with an amino acid sequence consisting of SEQ ID NO: 2 or 4 and which encodes a protein having the above activity of the present invention. More preferred is a nucleotide sequence which encodes an amino acid sequence sharing an identity of 95% or more with an amino acid sequence consisting of SEQ ID NO: 2 or 4 and which encodes a protein having the above activity of the present invention.

The percent identity between two amino acid sequences may be determined by visual inspection and mathematical calculation. Alternatively, the percent identity may be determined by using a computer program. Examples of such a computer program include BLAST, FASTA (Altschul et al., J. Mol. Biol., 215: 403-410 (1990)) and ClustalW. In particular, various conditions (parameters) for an identity search with the BLAST program are described by Altschul et al. (Nucl. Acids. Res., 25, p. 3389-3402, 1997) and publicly available via the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver.7 (Genetyx Corporation, Japan), DINASIS Pro (Hitachisoft, Japan) or Vector NTI (Infomax) for determination of the percent identity.

Certain alignment schemes for aligning amino acid sequences may also result in matching of a specific short region of the sequences, and it is also possible to detect a region with very high sequence identity in such a small aligned region even when there is no significant relationship between the full-length sequences used. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported).

(e) A nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes a protein having the above activity of the present invention.

Nucleotide sequences contained in the nucleic acids of the present invention include a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes a protein having the above activity of the present invention.

Such a protein consisting of the amino acid sequence shown in SEQ ID NO: 2 or 4 and hybridization conditions are as described above. Nucleotide sequences contained in the nucleic acids of the present invention include a nucleotide sequence which is hybridizable under stringent conditions with a nucleic acid consisting of a nucleotide sequence complementary to a nucleotide sequence encoding a protein consisting of the amino acid sequence shown in SEQ ID NO: 2 or 4 and which encodes a protein having the above activity of the present invention.

The nucleic acids of the present invention also include a nucleic acid which comprises a nucleotide sequence with deletion, substitution or addition of one or more nucleotides in a nucleotide sequence consisting of SEQ ID NO: 36 or 37 and encoding a protein having the above activity of the present invention. More specifically, it is also possible to use a nucleic acid which comprises a nucleotide sequence selected from:

(i) a nucleotide sequence with deletion of one or more (preferably one or several (e.g., 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 36 or 37;

(ii) a nucleotide sequence with substitution of other nucleotides for one or more (preferably one or several (e.g., 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 36 or 37;

(iii) a nucleotide sequence with addition of other one or more (preferably one or several (e.g., 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 36 or 37; or (iv) a nucleotide sequence with any combination of (i) to (iii) above,
and encoding a protein having the above activity of the present invention.

Preferred embodiments for the nucleic acids of the present invention also include a nucleic acid comprising a nucleotide sequence shown in any one of (a) to (c) below or a fragment thereof:
(a) the nucleotide sequence shown in SEQ ID NO: 36 or 37;
(b) a nucleotide sequence encoding a protein consisting of the amino acid sequence shown in SEQ ID NO: 2 or 4; or
(c) the nucleotide sequence shown in SEQ ID NO: 1 or 3. The above (a) nucleotide sequence shown in SEQ ID NO: 36 or 37, (b) nucleotide sequence encoding a protein consisting of the amino acid sequence shown in SEQ ID NO: 2 or 4, and (c) nucleotide sequence shown in SEQ ID NO: 1 or 3 are as shown in Table 1. Fragments of these sequences may be either naturally occurring or artificially prepared, including regions contained in the above nucleotide sequences, i.e., ORF, CDS, biologically active region, a region used as a primer as described later, and a region which may serve as a probe.

Lysophosphatidic Acid Acyltransferase Proteins of the Present Invention

The proteins of the present invention, which may be either naturally occurring or artificially prepared, include a protein consisting of the amino acid sequence shown in SEQ ID NO: 2 or 4 and proteins functionally equivalent to this protein. Such a protein consisting of the amino acid sequence shown in SEQ ID NO: 2 or 4 is as described above. "Proteins functionally equivalent" are intended to mean proteins having "the above activity of the present invention," as explained in the section "Nucleic acids of the present invention encoding lysophosphatidic acid acyltransferase" described above.

In the present invention, proteins functionally equivalent to a protein consisting of the amino acid sequence shown in SEQ ID NO: 2 or 4 include a protein shown in (a) or (b) below:
(a) a protein which consists of an amino acid sequence with deletion, substitution or addition of one or more amino acids in SEQ ID NO: 2 or 4 and which has the above activity of the present invention; or
(b) a protein which consists of an amino acid sequence sharing an identity of 69% or more with an amino acid sequence consisting of SEQ ID NO: 2 or 4 and which has the above activity of the present invention.

Among the above, the amino acid sequence with deletion, substitution or addition of one or more amino acids in SEQ ID NO: 2 or 4 or the amino acid sequence sharing an identity of 69% or more with an amino acid sequence consisting of SEQ ID NO: 2 or 4 is as explained in the section "Nucleic acids of the present invention encoding lysophosphatidic acid acyltransferase" described above. The phrase "protein which has the above activity of the present invention" is intended to also include mutants of a protein encoded by a nucleic acid comprising the nucleotide sequence of SEQ ID NO: 36 or 37, or mutated proteins with various modifications such as substitution, deletion or addition of one or more amino acids in the amino acid sequence shown in SEQ ID NO: 2 or 4, as well as their modified proteins whose amino acid side chains or the like are modified, and their fusion proteins with other proteins, as long as these proteins have LPAAT activity and/or the ability to yield the fatty acid rate of LPAAT in the present invention and/or the ability to increase the intracellular arachidonic acid content in the present invention.

The proteins of the present invention may also be artificially prepared by chemical synthesis techniques such as Fmoc method (fluorenylmethyloxycarbonyl method) and tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation (Japan) or other manufacturers may be used for chemical synthesis.

Cloning of LPAAT Nucleic Acids

The LPAAT nucleic acids of the present invention can be cloned, for example, by screening from a cDNA library using an appropriate probe. They can also be cloned by PCR amplification with appropriate primers and the subsequent ligation to an appropriate vector. The clones thus obtained may further be subcloned into another vector.

For example, it is possible to use commercially available plasmid vectors including pBlue-Script™ SK(+) (Stratagene), pGEM-T (Promega), pAmp (TM: Gibco-BRL), p-Direct (Clontech) and pCR2.1-TOPO (Invitrogen). In the case of using PCR amplification, primers may be any regions of the nucleotide sequence shown in, e.g., SEQ ID NO: 1 or 3. By way of example, it is possible to use the following primers from SEQ ID NO: 1:

I-1: 5'-GGATGTCATCAATGTCATCAATAGAG-3' (SEQ ID NO: 9) as an upstream primer; and

I-2: 5'-CTAACCCCCTCTTCCTCCACCAC-3' (SEQ ID NO: 10) as a downstream primer, or the following primers from SEQ ID NO: 3:

B-1: 5'-CCTCGCAAAATGTATCGTGG-3' (SEQ ID NO: 15) as an upstream primer; and

B-2: 5'-GATGGGAAGTTGAGCTTGAATG-3' (SEQ ID NO: 16) as a downstream primer. Then, PCR is performed on cDNA prepared from *M. alpina* cells with the above primers and thermophilic DNA polymerase or the like. Although this procedure can be readily accomplished by those skilled in the art according to, e.g., "Molecular Cloning, A Laboratory Manual 3rd ed." (Cold Spring Harbor Press (2001))," PCR conditions in the present invention may be set as follows, by way of example:

Denaturation temperature: 90-95° C.
Annealing temperature: 40-60° C.
Elongation temperature: 60-75° C.
Number of cycles: 10 or more cycles.

The resulting PCR products may be purified in a known manner, for example, by using a kit (e.g., GENECLEAN (Funakoshi Co., Ltd., Japan), QIAquick PCR purification Kits (QIAGEN), ExoSAP-IT (GE Healthcare Bio-Sciences)), a DEAE-cellulose filter or a dialysis tube. In the case of using an agarose gel, the PCR products are subjected to agarose gel electrophoresis and nucleotide sequence fragments are excised from the agarose gel, followed by purification with GENECLEAN (Funakoshi Co., Ltd., Japan) or QIAquick Gel extraction Kits (QIAGEN) or by the freeze-squeeze method, etc.

The cloned nucleic acids can be determined for their nucleotide sequences with a nucleotide sequencer.

Vector Construction for LPAAT Expression and Transformant Preparation

The present invention also provides a recombinant vector comprising a nucleic acid encoding LPAAT3 or LPAAT4 of the present invention. The present invention further provides a transformant transformed with the above recombinant vector.

Such a recombinant vector and transformant can be obtained as follows. Namely, a plasmid carrying a nucleic acid encoding the LPAAT of the present invention is digested with restriction enzymes. Examples of restriction enzymes available for use include, but are not limited to, EcoRI, KpnI, BamHI and SalI. This digestion may be followed by blunt ending with T4 polymerase. The digested nucleotide sequence fragment is purified by agarose gel electrophoresis. This nucleotide sequence fragment may be integrated into an expression vector in a known manner to obtain a vector for LPAAT expression. This expression vector is introduced into a host to prepare a transformant, which is then provided for expression of a desired protein.

In this case, the types of expression vector and host are not limited in any way as long as they allow expression of a desired protein. Examples of a host include fungi, bacteria, plants, animals or cells thereof. Fungi include filamentous fungi such as lipid-producing *M. alpina*, and yeast strains such as *Saccharomyces cerevisiae*. Bacteria include *Escherichia coli* (*E. coli*) and *Bacillus subtilis*. Likewise, plants include oil plants such as rapeseed, soybean, cotton, safflower and flax.

As lipid-producing strains, those such as found in MYCOTAXON, Vol. XLIV, NO. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, as well as microorganisms belonging to the subgenus *Micromucor* such as *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, IFO8185, IFO8287, *Mortierella vinacea* CBS236.82. Particularly preferred is *Mortierella alpina*.

When a fungus is used as a host, it is desirable that the nucleic acid of the present invention is self-replicable in the host or has a structure insertable onto the fungal chromosome. At the same time, it is preferable to further comprise a promoter and a terminator. When *M. alpina* is used as a host, examples of an expression vector include pD4, pDuraSC and pDura5. Any promoter may be used as long as it allows expression in the host, and examples include promoters derived from *M. alpina*, such as histonH4.1 gene promoter, GAPDH (glyceraldehyde-3-phosphate dehydrogenase) gene promoter and TEF (translation elongation factor) gene promoter.

Techniques for introducing a recombinant vector into filamentous fungi (e.g., *M. alpina*) include electroporation, spheroplast and particle delivery methods, as well as direct microinjection of DNA into nuclei. In the case of using an auxotrophic host strain, strains growing on a selective medium lacking nutrients required for the host strain may be selected to thereby obtain transformed strains. Alternatively, in a case where a drug resistance marker gene is used for transformation, culture may be carried out with a selective medium containing the drug to thereby obtain cell colonies resistant to the drug.

When yeast is used as a host, examples of an expression vector include pYE22m. Alternatively, commercially available yeast expression vectors such as pYES (Invitrogen) and pESC (STRATAGENE) may also be used. Yeast hosts suitable for the present invention include, but are not limited to, *Saccharomyces cerevisiae* strain EH13-15 (trp1, MATα). Examples of a promoter available for use include those derived from yeast or the like, such as GAPDH promoter, gal1 promoter and gal10 promoter.

Techniques for introducing a recombinant vector into yeast cells include lithium acetate, electroporation and spheroplast methods, as well as dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, examples of an expression vector include pGEX and pUC18 available from Pharmacia. Examples of a promoter available for use include those derived from *E. coli*, phage or the like, such as trp promoter, lac promoter, PL promoter and PR promoter. Techniques for introducing a recombinant vector into bacteria include electroporation and calcium chloride methods.

Method of the Present Invention for Preparing a Fatty Acid Composition

The present invention provides a method for preparing a fatty acid composition from the above transformant, i.e., a method for preparing a fatty acid composition from a cultured product obtained by culturing the above transformant, more specifically as described below. However, the method of the present invention is not limited to the following, and may be accomplished in any other manner generally known.

For culture of organisms transformed to express LPAAT, any medium may be used as long as it is a culture solution (medium) having appropriate pH and osmotic pressure as well as containing nutrients required for growth of each host, trace elements, and biomaterials such as serum or antibiotics. For example, in the case of yeast cells transformed to express LPAAT, SC-Trp medium, YPD medium, YPD5 medium or the like may be used without being limited thereto. Detailed medium composition is illustrated for SC-Trp medium: 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil) per liter of medium.

Any culture conditions may be used as long as they are suitable for host growth and are adequate for maintenance of the generated enzyme in a stable state. More specifically, individual conditions may be adjusted, including anaerobic degree, culture period, temperature, humidity, static culture or shaking culture. Culture may be accomplished under the same conditions (one-step culture) or by so-called two-step or three-step culture using two or more different culture conditions. For large-scale culture, two-step or more step culture is preferred because of its high culture efficiency.

To explain detailed procedures for the method of the present invention for preparing a fatty acid composition, two-step culture in which yeast is used as a host will be illustrated below as an example. Namely, in the pre-culture step, the colonies obtained above are inoculated into any medium described above (e.g., SC-Trp medium) and cultured with shaking at 30° C. for 2 days. Then, in the main culture step, the pre-cultured solution (500 μl) is added to 10 ml YPD5 (2% yeast extract, 1% polypeptone, 5% glucose) medium and cultured with shaking at 30° C. for 2 days.

Fatty Acid Compositions of the Present Invention

The present invention also provides a fatty acid composition which is a collection of one or more fatty acids in cells expressing LPAAT3 or LPAAT4 of the present invention. Such a fatty acid composition is preferably obtained by culturing a transformant expressing LPAAT3 or LPAAT4 of the present invention. Fatty acids may be free fatty acids or may be triglycerides, phospholipids or the like. In particular, the fatty acid composition of the present invention is characterized by having a fatty acid rate ensuring a higher ratio of at least one or more of:

i) the oleic acid content;
ii) the ratio of the palmitoleic acid content to the palmitic acid content;
iii) the ratio of the oleic acid content to the palmitic acid content; and
iv) the ratio of the total content of stearic acid and oleic acid to the palmitic acid content when compared to a cultured product obtained by culturing a host which is not transformed with the recombinant vector of the present invention, or is characterized by having a higher arachidonic acid content when compared to a cultured product obtained by culturing a host which is not transformed with the recombinant vector. The phrase "host which is not transformed with the recombinant vector of the present invention" as used herein is intended to mean, for example, a host transformed with an empty vector carrying none of the nucleic acids described in the section "Nucleic acids of the present invention encoding lysophosphatidic acid acyltransferase." It should be noted that when the above fatty acid composition is obtained under varying culture conditions, its fatty acid rate may vary slightly, as explained in the section "Nucleic acids of the present invention encoding lysophosphatidic acid acyltransferase" described above.

Fatty acids contained in the fatty acid composition of the present invention refer to linear or branched monocarboxylic acids of long-chain carbohydrates, including but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetradocosanoic acid) (24:0), nervonic acid (cis-15-tetradocosanoic acid) (24:1) and cerotic acid (hexadocosanoic acid) (26:0). It should be noted that the above substance names are common names defined by the IUPAC Biochemical Nomenclature, and their systematic names are given in parentheses along with numerics denoting the number of carbons and the positions of double bonds.

One of the characteristic features in the fatty acid composition of the present invention is high arachidonic acid content. Arachidonic acid, a substance represented by the chemical formula $C_{20}H_{32}O_2$ and having a molecular weight of 304.47, is a carboxylic acid containing 20 carbon atoms and 4 double bonds ([20:4(n−6)]) and classified as a member of the (n−6) series. Arachidonic acid is present as an important phospholipid (particularly phosphatidylethanolamine, phosphatidylcholine, phosphatidylinositol) in animal cell membranes and is contained in abundance in the brain. Moreover, arachidonic acid serves as a starting material for a series of eicosanoids (e.g., prostaglandin, thromboxane, leukotriene) generated by the arachidonic acid cascade, and is also important as a second messenger in intercellular signaling. On the other hand, arachidonic acid is synthesized from linolic acid in the animal body. However, depending on their species or age, some animals do not exert this function sufficiently to produce the required amount of arachidonic acid or have no function to produce arachidonic acid. Thus, arachidonic acid should be taken from food sources and can be regarded as an essential fatty acid.

The arachidonic acid content in the fatty acid composition of the present invention may be measured as follows, by way of example. Namely, a plasmid for LPAAT3 or LPAAT4 of the present invention is inserted into a vector such as pDuraSC or pDura5MCS, as described in Example 9, and transformed into a M. alpina strain. The resulting transformant is allowed to express and cultured according to the procedures described in Example 9. The cultured cells thus obtained are used to measure the fatty acid content in the cells and/or the arachidonic acid content per medium, etc. To analyze the arachidonic acid content, etc., for example, fatty acids in the resulting cultured cells are derived into corresponding fatty acid methyl esters by the hydrochloric acid/methanol method, and then extracted with hexane. After distilling off hexane, the fatty acids are analyzed by gas chromatography. According to this analysis, M. alpina transformed with LPAAT3 or LPAAT4 of the present invention has been found to show not only high fatty acid content in the cells, but also high arachidonic acid production per medium. Thus, the fatty acid composition of the present invention having high arachidonic acid content is preferred because it enables the efficient intake of arachidonic acid.

The fatty acid composition of the present invention may be composed of any number and any type of fatty acids, as long as it is a combination of one or more fatty acids selected from those listed above.

Whether such a fatty acid composition of the present invention is obtained, i.e., whether LPAAT3 or LPAAT4 of the present invention is expressed may be confirmed in a manner generally known, for example, as a change in fatty acid rate when LPAAT is expressed in yeast cells. Namely, to lyophilized cells obtained by the above method of the present invention for preparing a fatty acid composition, chloroform:methanol adjusted to an appropriate ratio is added and stirred, followed by heat treatment for an appropriate period. Centrifugation is further performed to separate the cells and collect the solvent. This procedure is repeated several times. Then, lipids are dried up in an appropriate manner, and a solvent such as chloroform is added to dissolve the lipids. An appropriate aliquot of this sample is treated by the hydrochloric acid/methanol method to derive fatty acids in the cells into corresponding methyl esters, followed by extraction with hexane. After distilling off hexane, the fatty acids are analyzed by gas chromatography.

As a result, if a fatty acid composition having the above fatty acid rate and/or a fatty acid composition having high arachidonic acid content is obtained, it can be determined that the fatty acid composition of the present invention was obtained. It should be noted that the LPAAT of the present invention yields a fatty acid rate different from that of known LPAAT fatty acid compositions, indicating that the LPAAT of the present invention has substrate specificity different from that of known LPAATs.

Food or Other Products Comprising Fatty Acid Compositions of the Present Invention The present invention also provides a food product comprising the above fatty acid composition. The fatty acid composition of the present invention can be used in a routine manner for purposes such as production of food products containing fats and oils as well as production of industrial source materials (those for cosmetics, pharmaceuticals (e.g., external preparations for skin), soaps, etc.). Cosmetics (cosmetic compositions) or pharmaceuticals (pharmaceutical compositions) may be formulated into any dosage form including, but not limited to, solutions, pastes, gels, solids or powders. Likewise, possible forms of food products include pharmaceutical formulations such as capsules, as well as processed foods such as ordinary fluid diets, semi-digested nourishing diets, elemental diets, drinkable preparations or enteral nutrient preparations, which comprise the fatty acid composition of the present invention in admixture with proteins, sugars, fats, trace elements, vitamins, emulsifiers, flavorings, etc.

Moreover, examples of the food product of the present invention include, but are not limited to, nutritional supplementary foods, health foods, functional foods, children's foods, infant modified milk, premature infant modified milk, and geriatric foods. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods. The term "infant modified milk" refers to modified milk given to children up to about one year old. The term "premature infant modified milk" refers to modified milk given to premature infants until about 6 months after birth.

These food products include natural foods (treated with fats and oils) such as meat, fish and nuts; foods supplemented with fats and oils during preparation (e.g., Chinese foods, Chinese noodles, soups); foods prepared using fats and oils as heating media (e.g., tempura (deep-fried fish and vegetables), deep-fried foods, fried bean curd, Chinese fried rice, doughnuts, Japanese fried dough cookies (karinto)); fat- and oil-based foods or processed foods supplemented with fats and oils during processing (e.g., butter, margarine, mayonnaise, dressing, chocolate, instant noodles, caramel, biscuits, cookies, cake, ice cream); and foods sprayed or coated with fats and oils upon finishing (e.g., rice crackers, hard biscuits, sweet bean paste bread). However, the food product of the present invention is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine (sake), medicinal liquor, sweet cooking sherry (mirin), vinegar, soy sauce and miso (bean paste); livestock food products such as yogurt, ham, bacon and sausage; seafood products such as fish cake (kamaboko), deep-fried fish cake (ageten) and puffy fish cake (hanpen); as well as fruit drinks, soft drinks, sports drinks, alcoholic beverages, and tea.

Method for Strain Evaluation or Selection Using LPAAT-Encoding Nucleic Acid or LPAAT Protein of the Present Invention The present invention also provides a method for evaluating or selecting a lipid-producing strain using the LPAAT-encoding nucleic acid or LPAAT protein of the present invention. Details are given below.

(1) Evaluation Method

One embodiment of the present invention is a method for evaluating a lipid-producing strain using the LPAAT-encoding nucleic acid or LPAAT protein of the present invention. As a first example for the above evaluation method of the present invention, lipid-producing test strains are evaluated for the above activity of the present invention by using primers or probes designed based on the nucleotide sequence of the present invention. General procedures for such evaluation are known and can be found in, e.g., International Patent Publication No. WO01/040514 or JP 8-205900 A. A brief explanation will be given below of this evaluation.

First, the genome of a test strain is prepared. For genome preparation, it is possible to use any known technique such as Hereford method or potassium acetate method (see, e.g., Methods in Yeast Genetics, Cold Spring Harbor Laboratory Press, p 130 (1990)).

Primers or probes are designed based on the nucleotide sequence of the present invention, preferably SEQ ID NO: 36 or 37. These primers or probes may be any regions of the nucleotide sequence of the present invention, and known procedures may be used for their design. The number of nucleotides in a polynucleotide used as a primer is generally 10 nucleotides or more, preferably 15 to 25 nucleotides. Likewise, the number of nucleotides appropriate for a region to be flanked by primers is generally 300 to 2000 nucleotides.

The primers or probes prepared above are used to examine whether the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence located upstream or downstream of this sequence or a polynucleotide comprising a nucleotide sequence complementary to the above nucleotide sequence is used as the other primer to amplify nucleic acids from the test strain by PCR or other techniques, followed by determining the presence or absence of amplification products, the molecular weight of amplification products, etc.

PCR conditions suitable for the method of the present invention are not limited in any way, and may be set as follows, by way of example:

Denaturation temperature: 90-95° C.
Annealing temperature: 40-60° C.
Elongation temperature: 60-75° C.
Number of cycles: 10 or more cycles.

The resulting amplification products, which are the reaction products, may be separated by electrophoresis on an agarose gel or the like to determine the molecular weight of the amplification products. Each amplification product is then confirmed as to whether its molecular weight is a size enough to cover a nucleic acid molecule corresponding to a region specific to the nucleotide sequence of the present invention, whereby the test strain can be predicted or evaluated for the above activity of the present invention. Moreover, if the above amplification products are analyzed for their nucleotide sequences, as described above, the above activity of the present invention can be predicted or evaluated with more accuracy. It should be noted that procedures for evaluating the above activity of the present invention are as described above.

As another example for the above evaluation method of the present invention, a test strain is cultured and measured for the expression level of LPAAT encoded by the nucleotide sequence of the present invention (e.g., SEQ ID NO: 36 or 37), whereby the test strain can be evaluated for the above activity of the present invention. It should be noted that the expression level of LPAAT can be measured by culturing a test strain under appropriate conditions and quantifying mRNA or protein for LPAAT. Quantification of mRNA or protein may be accomplished by using known procedures, for example, Northern hybridization or quantitative RT-PCR for mRNA quantification and Western blotting for protein quantification (Current Protocols in Molecular Biology, John Wiley & Sons 1994-2003). For evaluation of the above activity, it is also possible to measure the fatty acid rate and/or arachidonic acid content of a fatty acid composition produced by the LPAAT of the present invention. Procedures for measuring the fatty acid rate and/or arachidonic acid content of a fatty acid composition are as described above.

(2) Selection Method

Another embodiment of the present invention is a method for selecting a lipid-producing strain using the LPAAT-encoding nucleic acid or LPAAT protein of the present invention. As an example for the above selection method of the present invention, test strains are cultured and measured for the expression level of LPAAT encoded by the nucleotide sequence of the present invention (e.g., SEQ ID NO: 36 or 37) to select a strain with a desired expression level, whereby a strain having a desired activity can be selected. Alternatively, a type strain is predetermined, and this type strain and test strains are each cultured and measured for the above expression level, followed by comparison of the expression level between the type strain and each test strain, whereby a desired strain can be selected. More specifically, for example, a type strain and test strains are cultured under appropriate conditions and measured for their expression levels to select a test strain showing higher or lower expression than the type strain, whereby a strain having a desired activity can be selected. Examples of a desired activity include the expression level of LPAAT, and/or the fatty acid rate and/or arachidonic acid content of a fatty acid composition produced by LPAAT, which may be measured as described above.

As another example for the above selection method of the present invention, test strains are cultured to select a strain in which the above activity of the present invention is high or low, whereby a strain having a desired activity can be selected. Examples of a desired activity include the expression level of LPAAT, and/or the fatty acid rate and/or arachidonic acid content of a fatty acid composition produced by LPAAT, which may be measured as described above.

Examples of a test strain or type strain available for use include, but are not limited to, a strain transformed with the above vector of the present invention, a strain modified to suppress expression of the above nucleic acid of the present invention, a strain modified by mutagenesis, and a strain having natural mutation(s). It should be noted that LPAAT activity in the present invention, the ability to yield the fatty acid rate of LPAAT in the present invention and the ability to increase the intracellular arachidonic acid content in the present invention can be measured, for example, by the procedures described in the sections "Nucleic acids of the present invention encoding lysophosphatidic acid acyltransferase" and "Fatty acid compositions of the present invention." Mutagenesis may be accomplished by, but not limited to, physical techniques including ultraviolet or radioactive irradiation, or chemical techniques including treatment with an agent such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Strains used in the present invention as type and test strains include, but are not limited to, the above lipid-producing strains or yeast strains. More specifically, the type strain or test strain may be a combination of any strains belonging to different genera or species, and one or more test strains may be used simultaneously.

The present invention will now be described in more detail by way of the following examples, which are not intended to limit the scope of the invention.

Example 1

(1) EST Analysis

*M. alpina* strain 1S-4 was inoculated into 100 ml medium (1.8% glucose, 1% yeast extract, pH 6.0) and pre-cultured for 3 days at 28° C. A 10 L culture vessel (Able Co., Tokyo) was charged with 5 L medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 win and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using an Oligotex-dT30<Super>mRNA ('dT30' disclosed as SEQ ID NO: 53) Purification Kit (Takara Bio Inc., Japan), poly(A)⁺RNA was purified from the total RNA. A cDNA library was prepared for each stage with a ZAP-cDNA GigapackIII Gold Cloning Kit (STRATAGENE), followed by one-pass sequence analysis from the 5'-end of cDNA (8000 clones×5 stages). The resulting sequences were clustered. As a result, about 5000 sequences were obtained.

(2) Search for LPAAT Gene Homologs

The nucleotide sequences obtained from EST analysis were searched against amino acid sequences registered in GENEBANK with a homology search program, BLASTX, to extract homologs of the LPAAT gene. As a result, four LPAAT homolog sequences (SEQ ID NOs: 1, 5, 6 and 7) were found.

Proteins with which these sequences were found to share the highest identity during the above search are as follows:

SEQ ID NO: 5 was found to share the highest identity with a *Neurospora crassa*-derived 1-acyl-sn-glycerol-3-phosphate acyltransferase-like putative protein (GB accession No. EAA28956);

SEQ ID NO: 6 was found to share the highest identity with a *Brassica napus*-derived 1-acyl-sn-glycerol-3-phosphate acyltransferase-like putative protein (GB accession No. T07936);

SEQ ID NO: 1 was found to share the highest identity with an *Emericella nidulans*-derived 1-acyl-sn-glycerol-3-phosphate acyltransferase-like protein, AtaAp (GB accession No. AAD37345); and SEQ ID NO: 7 was found to share the highest identity with a *S. cerevisiae*-derived 1-acyl-sn-glycerol-3-phosphate acyltransferase protein, Slc1p (GB accession No. CAA98614).

*M. alpina* LPAAT homolog sequences appearing in International Patent Publication No. WO2004/087902 and US Patent Publication No. US2006/0094090 were compared with the sequences obtained above, indicating that SEQ ID NO: 5 was a partial sequence of LPAAT1 homolog, and SEQ ID NO: 6 was a partial sequence of LPAAT2 homolog.

Thus, the gene of SEQ ID NO: 5 was identified as LPAAT1 gene, the gene of SEQ ID NO: 6 was identified as LPAAT2 gene, the gene of SEQ ID NO: 1 was identified as LPAAT3 gene, and the gene of SEQ ID NO: 7 was identified as LPAAT4 gene.

With respect to the above sequences, their source libraries and ESTs are as shown in Table 2. It should be noted that in Table 2, clones are classified by the day of culture on which their source cDNA libraries were obtained.

TABLE 2

| Gene | SEQ ID NO | Source library |||||
|---|---|---|---|---|---|---|
| | | Day 1 | Day 2 | Day 3 | Day 6 | Day 8 |
| LPAAT1 | SEQ ID NO: 5 | | 1 | | 1 | 3 |
| LPAAT2 | SEQ ID NO: 6 | | | 1 | | |
| LPAAT3 | SEQ ID NO: 1 | | 1 | 3 | 1 | |
| LPAAT4 | SEQ ID NO: 7 | | | 7 | | |

Example 2

(1) Cloning of LPAAT Homologs

SEQ ID NO: 1 contains a CDS of 990 bp (SEQ ID NO: 8) and would be a sequence encoding the full-length LPAAT3 gene. The deduced amino acid sequence of a protein (LPAAT3p) encoded by this gene is shown in SEQ ID NO: 2. For PCR amplification of DNA containing this ORF sequence, the following primers were prepared:

```
Primer I-1:
GGATGTCATCAATGTCATCAATAGAG;    (SEQ ID NO: 9)
and

Primer I-2:
CTAACCCCCTCTTCCTCCACCAC.       (SEQ ID NO: 10)
```

The cDNA library on day 3 was used as a template to perform PCR with primers I-1 and I-2 using ExTaq (Takara Bio Inc., Japan). PCR conditions were set as follows: 94° C. for 2 minutes, and 30 cycles of 94° C. for 1 minute, 54° C. for 1 minute and 72° C. for 2 minutes.

The amplified fragments were TA-cloned with a TOPO-TA cloning Kit (INVITROGEN CORPORATION). Several clones were confirmed for their nucleotide sequences, and a clone appearing to contain the correct nucleotide sequence of this gene was designated as pCR-LPAAT3.

SEQ ID NOs: 5, 6 and 7 contain no CDS appearing to encode a LPAAT homolog. Thus, for cloning of cDNAs encoding the full lengths of these genes, primers were prepared based on each sequence as follows.

Primers Designed Based on SEQ ID NO: 5:

```
Primer 955-1: GGACGTGTCAAGGAAAAGGA  (SEQ ID NO: 11)

Primer 955-2: TCCTTCAGATGAGCCTCCTG  (SEQ ID NO: 12)
```

Primers Designed Based on SEQ ID NO: 6:

```
Primer A-1: ggcgtccttctccacgtacttc  (SEQ ID NO: 13)

Primer A-2: gtgaaatacattccattctacg  (SEQ ID NO: 14)
```

Primers Designed Based on SEQ ID NO: 7:

```
Primer B-1: CCTCGCAAAATGTATCGTGG  (SEQ ID NO: 15)

Primer B-2: GATGGGAAGTTGAGCTTGAATG  (SEQ ID NO: 16)
```

Using these primers, PCR was performed with ExTaq (Takara Bio Inc., Japan) by using a cDNA library containing ESTs constituting SEQ ID NO: 5, 6 or 7 as a template. The resulting DNA fragments were TA-cloned with a TOPO-TA cloning Kit (INVITROGEN CORPORATION) to determine the nucleotide sequence for each insert.

The results confirmed that DNA fragments comprising nucleotide sequences covering nucleotides 20-518 of SEQ ID NO: 5, nucleotides 116-616 of SEQ ID NO: 6 and nucleotides 159-687 of SEQ ID NO: 7 were each cloned. These plasmids were designated as pCR-955-P, pCR-A-P and pCR-B-P, respectively. Then, these plasmids were each used as a template to perform PCR with the above primers. In PCR, ExTaq (Takara Bio Inc., Japan) was used, but the attached dNTP mix was replaced by a PCR labeling mix (Roche Diagnostics) for digoxigenin (DIG) labeling of DNAs to be amplified, thereby preparing probes for use in cDNA library screening. These probes were used to screen the cDNA libraries from which the ESTs constituting the individual sequences had been obtained by EST analysis.

Hybridization conditions were set as follows.

Buffer: 5×SSC, 1% SDS, 50 mM Tris-HCl (pH 7.5), 50% formamide

Temperature: 42° C. (overnight)

Washing conditions: in 0.2×SSC, 0.1% SDS at 65° C. for 20 minutes (repeated three times)

Detection was accomplished by using a DIG nucleic acid detection kit (Roche Diagnostics). From phage clones obtained by screening, the plasmids were excised by in vivo excision to obtain each plasmid DNA.

The nucleotide sequence of an insert from a clone obtained by screening of cDNA containing SEQ ID NO: 5 is shown in SEQ ID NO: 17. SEQ ID NO: 17 contains a CDS of 1254 bp between positions 36 and 1289, thus suggesting that a sequence encoding the full length of LPAAT1 homolog was obtained. The deduced amino acid sequence of a protein encoded by this gene is shown in SEQ ID NO: 18. The plasmid containing SEQ ID NO: 17 was designated as pB-LPAAT1.

The nucleotide sequence of the longest insert among clones obtained by screening of cDNA containing SEQ ID NO: 6 is shown in SEQ ID NO: 19. SEQ ID NO: 19 contains a CDS of 924 bp between positions 26 and 949, thus suggesting that a sequence encoding the full length of LPAAT2 homolog was obtained. The deduced amino acid sequence of a protein encoded by this gene is shown in SEQ ID NO: 20. The plasmid containing SEQ ID NO: 19 was designated as pB-LPAAT2.

Among clones obtained by screening of cDNA containing SEQ ID NO: 7, a clone with the longest insert was determined for its nucleotide sequence, indicating that this clone contained a nucleotide sequence covering nucleotides 103-1148 of SEQ ID NO: 1. This sequence was found to contain a sequence overlapping with SEQ ID NO: 7 obtained previously; when these sequences were assembled, the sequence shown in SEQ ID NO: 3 was obtained. SEQ ID NO: 3 contains a CDS of 942 bp shown in SEQ ID NO: 23, thus suggesting that a sequence encoding the full length of LPAAT homolog was obtained. The deduced amino acid sequence of a protein (LPAAT4p) encoded by this gene is shown in SEQ ID NO: 4. For PCR amplification of DNA containing this region, the following primers were prepared:

B-3: CATGTCCATAGGCTCTTCTAATCC; (SEQ ID NO: 21)
and

B-4: GTTTTACTCTTTCAGTGTCCTCC. (SEQ ID NO: 22)

cDNA prepared from the cells on day 3 was used as a template to perform PCR with primers B-3 and B-4 using ExTaq (Takara Bio Inc., Japan). The amplified fragments were TA-cloned into pCR2.1-TOPO and confirmed for their nucleotide sequences. A clone appearing to contain the correct nucleotide sequence of this gene was designated as pCR-LPAAT4.

(2) Sequence Analysis

The thus obtained cDNA sequences of *M. alpina*-derived LPAAT homologs were subjected to BLASTX homology analysis against amino acid sequences registered in GENEBANK. As a result, amino acid sequences having the lowest E-value, i.e., sharing the highest identity with each sequence are as shown below. The sequences sharing the highest identity were analyzed by clustalW to determine their identity with ORF of each sequence at the nucleotide and amino acid sequence levels, which are also shown below.

SEQ ID NO: 17 was found to have an identity of 51% at the nucleotide sequence level and 32.1% at the amino acid sequence level, in comparison with a corresponding region of an *Aspergillus nidulans*-derived 1-acyl-sn-glycerol-3-phosphate acyltransferase-like putative protein (GB accession No. EAA60126).

SEQ ID NO: 19 was found to have an identity of 53% at the nucleotide sequence level and 31% at the amino acid sequence level, in comparison with a corresponding region of a *Magnaporthe grisea*-derived 1-acyl-sn-glycerol-3-phosphate acyltransferase-like putative protein (GB accession No. EAA48685).

SEQ ID NOs: 1 and 3 were found to have an identity of 49% and 51% at the nucleotide sequence level and 37% and 36% at the amino acid sequence level, respectively, in comparison with a corresponding region of a *Ustilago maydis*-derived 1-acyl-sn-glycerol-3-phosphate acyltransferase-like putative protein (GB accession No. EAK87199).

SEQ ID NOs: 17 and 19 were also each compared with *M. alpina*-derived known LPAAT homologs, i.e., LPAAT1 gene (WO2004/087902) and LPAAT2 gene (US2006/0094090), as well as with deduced amino acid sequences encoded by these genes. The sequences disclosed in the above documents and the sequences obtained from *M. alpina* strain 1S-4 were compared with each other in their corresponding regions, confirming that there was an identity of 89% at the nucleotide sequence level and 91% at the amino acid sequence level for LPAAT1, while there was an identity of 92% at the nucleotide sequence level and 98% at the amino acid sequence level for LPAAT2.

In contrast, none of SEQ ID NOs: 1 to 4 shared significantly high identity with known nucleotide sequences and amino acid sequences, thus suggesting that they would be novel LPAAT genes derived from *M. alpina*. Their cDNA sequences and deduced amino acid sequences are shown in FIGS. 2 and 3. A comparison of DNA sequences between ORF regions of LPAAT3 and LPAAT4 indicated an identity of 67% (FIG. 4). Likewise, a comparison of deduced amino acid sequences between proteins LPAAT3p and LPAAT4p encoded by these genes indicated an identity of 69% (FIG. 5).

The deduced amino acid sequences of LPAAT3p and LPAAT4p were compared with known amino acid sequences (FIG. 6). As underlined in the figure, the consensus sequence $HX_4D$ of glycerolipid acyltransferase (J. Bacteriology, 180, 1425-1430, 1998) was conserved in LPAAT3p and LPAAT4p, as in the case of these known LPAAT proteins or homologs thereof.

Among the amino acids in FIG. 6, the amino acid sequence indicated as gi__46101966 (SEQ ID NO: 40) is derived from *Ustilago maydis* 521 (GB accession No. EAK87199), the amino acid sequence indicated as gi__5002178 (SEQ ID NO: 41) is derived from *Emericella nidulans* (GB accession No. AAD37345), the amino acid sequence indicated as gi_6320151 (SEQ ID NO: 42) is derived from *Saccharomyces cerevisiae* (GB accession No. NP_010231), the amino acid sequence indicated as gi_19115517 (SEQ ID NO: 43) is derived from *Schizosaccharomyces pombe* 972h—(GB accession No. NP_594605), and the amino acid sequence indicated as gi_17564032 (SEQ ID NO: 44) is derived from *Caenorhabditis elegans* (GB accession No. NP_505578).

Example 3

Measurement of LPAAT Activity (1) Breeding of Strain Δslc1:URA3

To obtain the CDS of SLC1 known as a gene responsible for LPAAT activity in yeast, the following primers were prepared:

```
Primer SLC1-1
ggtgaaggggaattcttc;        (SEQ ID NO: 45)
and

Primer SLC1-2
atgtcgacgtggcttaatgcatc.   (SEQ ID NO: 46)
```

To obtain genomic DNA from *Saccharomyces cerevisiae* strain S288C, this strain was inoculated into YPD medium (10 ml) and cultured with shaking at 30° C. for 1 day. From 1.5 ml of the culture solution, DNA was extracted with a Dr. GenTLE (for Yeast) kit (Takara Bio Inc., Japan). This was used as a template to amplify the CDS of SLC1 by PCR with primers SLC-1 and SLC-2. The resulting PCR product was digested with restriction enzymes EcoRI and SalI, inserted into the EcoRI-SalI site of vector pUC18, and then confirmed for its nucleotide sequence to obtain plasmid pUC-SLC1. Subsequently, the plasmid pUC-SLC1 was digested with a restriction enzyme SalI, followed by blunt ending and self-ligation to obtain plasmid pUC-SLC1-2.

A strain lacking the SLC1 gene was prepared as follows. Plasmid pURA34 (JP 2001-120276 A) was digested with a restriction enzyme HindIII and blunt-ended to obtain a DNA fragment of approximately 1.2 kb, while the plasmid pUC-SLC1-2 was digested with restriction enzymes EcoRV and HincII to obtain a DNA fragment of approximately 3.1 kb. These DNA fragments were ligated to construct plasmid pUCΔslc1:URA3. *Saccharomyces cerevisiae* strain YPH499 (STRATAGENE) was transformed with an EcoRI- and HindIII-digested DNA fragment from the plasmid pUCΔslc1: URA3. The transformed strains were screened by the ability to grow on SC-Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 1.2 g tryptophan). Among the resulting transformed strains, any one strain was designated as strain Δslc1:URA3-1.

(2) Introduction of LPAAT Gene into Strain Δslc1:URA3

To construct a vector for ScSLC1 expression, pUC-SLC1 was digested with restriction enzymes EcoRI and SalI, and the resulting DNA fragment of 0.9 kb was inserted into the EcoRI-SalI site of vector pYE22m to construct plasmid pYE-ScSLC1.

The strain Δslc1:URA3-1 was transformed respectively with plasmids pYE22m, pYELPAAT3, pYELPAAT4 and pYESLC1. The transformed strains were screened by the ability to grow on SC-Trp,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine and 6 g threonine).

Any strains of the transformed strains obtained with the respective plasmids were designated as strain C-3, strain LPAAT2-3, strain LPAAT3-3 and strain SLC1-3.

(3) Preparation of Microsomal Fraction

The strains C-3, LPAAT3-3, LPAAT4-3 and SLC1-3 were each cultured with shaking in SC-Trp,Ura liquid medium (10 ml) at 30° C. for 1 day. A 1 ml aliquot of each culture solution was inoculated into SC-Trp,Ura liquid medium (100 ml) and cultured at 28° C. for 1 day. The cells were collected by centrifugation, and half of them were washed with sterilized water and then suspended in 5 ml buffer B (0.6 M sorbitol, 5 mM 2-(N-Morpholino)ethanesulfonic Acid (MES), 1 mM KCl, 0.5 mM ethylenediaminetetraacetic acid (EDTA), 1 mM phenylmethylsulfonyl (PMSF), pH 6.0). The cells were homogenized at 16 kPa with a French press and centrifuged at 20000×g for 1 hour at 4° C. The resulting supernatant was further centrifuged at 100000×g for 1 hour at 4° C., and the resulting precipitate was dissolved in buffer B to prepare a microsomal fraction. The protein concentration contained in each sample was quantified with protein assay CBB solution (Nacalai Tesque, Inc., Japan).

(4) Measurement of LPAAT Activity

LPAAT activity was measured as follows. A reaction solution was prepared in a total volume of 500 μl containing 100 μg 1-oleoyl-2-hydroxy-sn-glycero-3-phosphate (LPA-18:1), 50 μg linoleoyl-coenzyme A (18:2-CoA), 0.5 mM dithiothreitol (DTT), 0.5 mg bovine serum albumin (BSA), 2 mM $MgCl_2$, 50 mM Tris-HCl buffer (pH 7.5) and 100 microsomal fraction. After reaction at 28° C. for 10 minutes, chloroform:methanol (1:2, 1875 μl) was added to stop the reaction. As an internal standard, 1,2-diheptadecanoyl-sn-glycero-phosphate (20 μg) was added. Lipids were extracted according to the method of Bligh & Dyer et al., and the whole of them were fractionated by thin-layer chromatography (TLC). For TLC, silica gel 60 plates (Merck & Co., Inc.) were used and the developing solvent was chloroform:methanol:acetic acid:water=170:25:25:4. A PA fraction was collected by scrapping, and dichloromethane (1 ml) and 10% hydrochloric acid/methanol (2 ml) were added thereto to derive fatty acids into corresponding methyl esters by the hydrochloric acid/methanol method, followed by extraction with hexane. After distilling off hexane, the fatty acids were analyzed by gas chromatography to quantify the amount of linolic acid contained in this fraction. The level of linolic acid in the PA fraction during the above reaction is shown in the table below, expressed per protein in each enzyme solution.

TABLE 3

| Linolic acid level in PA fraction per protein in enzyme solution (LPAAT activity) | | | | |
|---|---|---|---|---|
| Sample name | C-3 | LPAAT3-3 | LPAAT4-3 | SLC1-3 |
| 18:2 μg/mg-protein | 0.20 | 1.04 | 10.51 | 2.99 |

As shown above, the strain transformed to express LPAAT3, LPAAT4 or SLC1 showed an increase in the amount of linolic acid (18:2) incorporated into the PA fraction during the above reaction, indicating that LPAAT3 and LPAAT4 had LPAAT activity.

Example 4

Construction of Yeast Expression Vector

To express LPAAT1, LPAAT2, LPAAT3 and LPAAT4 in yeast cells, yeast expression vectors were constructed as follows.

To express LPAAT1 in yeast cells, a yeast expression vector was constructed as follows. Namely, the plasmid Pb-LPAAT1 was used as a template to perform PCR with the following primers LPAAT1-6F (SEQ ID NO: 38) and LPAAT1-R1 (SEQ ID NO: 39) using ExTaq (Takara Bio Inc., Japan).

```
LPAAT1-6F:
TCTGAGATGGATGAATCCACCACCACCAC    (SEQ ID NO: 38)

LPAAT1-R1:
GTCGACTCAACCAGACGATACTTGCTGCAGAG (SEQ ID NO: 39)
```

The resulting DNA fragments were TA-cloned with a TOPO-TA cloning Kit (INVITROGEN) to confirm the nucleotide sequence of each insert. A plasmid carrying the correct nucleotide sequence was designated as pCR-LPAAT1. This plasmid was digested with restriction enzymes EcoRI and SalI to obtain a DNA fragment of approximately 1.3 kb, which was then inserted into the EcoRI-SalI site of yeast expression vector pYE22m to construct plasmid pYE-MALPAAT1.

To express LPAAT2 in yeast cells, a yeast expression vector was constructed as follows. Namely, the plasmid pB-LPAAT2 was digested with a restriction enzyme KpnI, blunt-ended by treatment with alkaline phosphatase and then digested with a restriction enzyme BamHI. The resulting DNA fragment was inserted into yeast expression vector pYE22m which had been digested with a restriction enzyme SalI, blunt-ended and then digested with a restriction enzyme BamHI. The construct thus obtained was designated as plasmid pYE-MALPAAT2.

To express LPAAT3 and LPAAT4 in yeast cells, yeast expression vectors were constructed as follows. Namely, the plasmid pCR-LPAAT3 or pCR-LPAAT4 was digested with a restriction enzyme EcoRI to excise the insert, which was then ligated to the EcoRI site of yeast expression vector pYE22m. The orientation of the inserted DNA fragment was confirmed for each case, and constructs carrying the respective inserts in such an orientation as to cause ORF transcription from the GAPDH promoter of pYE22m were designated as pYE-MALPAAT3 and pYE-MALPAAT4, respectively.

Example 5

Yeast Transformation

The plasmid pYE22m, pYE-MALPAAT1, pYE-MALPAAT2, pYE-MALPAAT3 or pYE-MALPAAT4 was used to transform yeast *Saccharomyces cerevisiae* strain EH13-15 (trp1, MATα) (Appl. Microbiol. Biotechnol., 30, 515-520, 1989) by the lithium acetate method. The transformed strains were screened by the ability to grow on SC-Trp agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Example 6

Yeast Culture

Among the transformed strains obtained with each vector, any two strains (strains c-1 and c-2, strains LPAAT1-1 and LPAAT1-2, strains LPAAT2-1 and LPAAT2-2, strains LPAAT3-1 and LPAAT3-2, or strains LPAAT4-1 and LPAAT4-2) were selected and cultured under the following conditions.

Namely, in the pre-culture step, a loopful of each yeast strain was inoculated from the plate into SC-Trp medium (10 ml) and cultured with shaking at 30° C. for 2 days. In the main culture step, the pre-cultured solution (500 µl) was added to 10 ml YPD5 (2% yeast extract, 1% polypeptone, 5% glucose) medium and cultured with shaking at 30° C. for 2 days.

Example 7

Fatty Acid Analysis of Yeast Strains

The cultured yeast solutions were each centrifuged to collect the cells. After washing with 10 ml sterilized water, the cells were collected again by centrifugation and lyophilized. To the lyophilized cells, chloroform:methanol (2:1, 4 ml) was added and stirred vigorously, followed by incubation at 70° C. for 1 hour. The cells were separated by centrifugation to collect the solvent. To the reaming cells, chloroform:methanol (2:1, 4 ml) was added again, and the same procedure was repeated to collect the solvent. After lipids were dried up with a SpeedVac, 2 ml chloroform was added to dissolve the lipids. A 200 µl aliquot of this sample was treated by the hydrochloric acid/methanol method to derive fatty acids in the cells into corresponding methyl esters, followed by extraction with hexane. After distilling off hexane, the fatty acids were analyzed by gas chromatography.

The results obtained are shown in Table 4.

TABLE 4

| Fatty acid rate of transformed strains (host: EH13-15) | | | | | | | | | | | | |
|---|---|---|---|---|---|---|---|---|---|---|---|---|
| Sample name | C-1 | C-2 | LPAAT 2-1 | LPAAT 2-2 | LPAAT 3-1 | LPAAT 3-2 | LPAAT 4-1 | LPAAT 4-2 | C-1 | C-2 | LPAAT 1-1 | LPAAT 1-2 |
| 16:0 | 8.46 | 6.46 | 6.33 | 6.27 | 4.48 | 4.65 | 5.27 | 3.99 | 8.83 | 6.76 | 12.49 | 15.26 |
| 16:1 | 43.26 | 43.1 | 41.49 | 42.17 | 35.72 | 36.39 | 38.22 | 34.71 | 40.55 | 43.56 | 35.59 | 35.62 |
| 18:0 | 4.09 | 4.57 | 4.58 | 4.44 | 4.85 | 4.68 | 4.13 | 4.58 | 5.41 | 4.74 | 4.85 | 5.27 |
| 18:1 | 44.19 | 45.87 | 47.6 | 47.12 | 54.94 | 54.28 | 52.39 | 56.72 | 45.21 | 44.94 | 47.07 | 43.85 |
| 16:1/16:0 | 5.11 | 6.67 | 6.55 | 6.73 | 7.97 | 7.83 | 7.25 | 8.70 | 4.59 | 6.44 | 2.85 | 2.33 |
| 18:1/16:0 | 5.22 | 7.10 | 7.52 | 7.52 | 12.26 | 11.67 | 9.94 | 14.22 | 5.12 | 6.65 | 3.77 | 2.87 |
| 18:1 + 18:0/16:0 | 5.71 | 7.81 | 8.24 | 8.22 | 13.35 | 12.68 | 10.72 | 15.36 | 5.73 | 7.35 | 4.16 | 3.22 |
| 18:0 + 18:1/16:0 + 16:1 | 0.93 | 1.02 | 1.09 | 1.06 | 1.49 | 1.44 | 1.30 | 1.58 | 1.03 | 0.99 | 1.08 | 0.97 |

The yeast strains transformed with four LPAAT homologs derived from *M. alpina* and the control yeast strains were compared for their fatty acid rate. In the fatty acid rate of the LPAAT2-transformed yeast, the percentage of oleic acid increased slightly when compared to the control strains, but there was little difference. On the other hand, in the fatty acid rate of the LPAAT1-transformed yeast, the percentage of palmitic acid increased, but the palmitoleic acid content decreased when compared to the control strains. Thus, the ratio of the palmitoleic acid content to the palmitic acid content was lower than that of the control strains. Stearic acid and oleic acid were in the same percentages as in the control strains.

In contrast, in the LPAAT3- or LPAAT4-transformed yeast, the percentage of oleic acid increased by 10% or more when compared to the control strains, whereas the percentages of palmitoleic acid and palmitic acid both decreased. The ratio of palmitoleic acid to palmitic acid was higher than that of the control strains.

These results indicated that four LPAAT homologs derived from *M. alpina* had different specificity for their substrate acyl group, and hence yeast strains transformed with these genes yielded different fatty acid rates from homolog to homolog. The results also indicated that it was possible to breed organisms with a desired fatty acid rate when the above homologs were selected to suit the intended purpose.

Example 8

Expression Analysis in Arachidonic Acid-Producing Yeast Strains (1) Breeding of Arachidonic Acid-Producing Yeast Strains To breed arachidonic acid-producing yeast (*Saccharomyces cerevisiae*) strains, the following plasmids were constructed.

First, cDNA prepared from *M. alpina* strain 1S-4 was used as a template to perform PCR with ExTaq using a primer set of Δ12-f and Δ12-r, Δ6-f and Δ6-r, GLELO-f and GLELO-r, or Δ5-f and Δ5-r to thereby amplify the Δ12 fatty acid desaturase gene, the Δ6 fatty acid desaturase gene, the GLELO fatty acid elongase gene or the Δ5 fatty acid desaturase gene in the *M. alpina* strain 1S-4.

```
Δ12-f:
TCTAGAatggcacctcccaacactattg      (SEQ ID NO: 24)

Δ12-r:
AAGCTTTTACTTCTTGAAAAGACCACGTC     (SEQ ID NO: 25)

Δ6-f:
TCTAGAatggctgctgctcCcagtgtgag     (SEQ ID NO: 26)

Δ6-r:
AAGCTTTTACTGTGCCTTGCCCATCTTGG     (SEQ ID NO: 27)

GLELO-f:
TCTAGAatggagtcgattgcgcaattcc      (SEQ ID NO: 28)

GLELO-r:
GAGCTCTTACTGCAACTTCCTTGCCTTCTC    (SEQ ID NO: 29)

Δ5-f:
TCTAGAatgggtgcggacacaggaaaaacc    (SEQ ID NO: 30)

Δ5-r:
AAGCTTTTACTCTTCCTTGGGACGAAGACC    (SEQ ID NO: 31)
```

These genes were cloned with a TOPO-TA-cloning Kit. The clones were confirmed for their nucleotide sequences, and those containing the nucleotide sequences of SEQ ID NOs: 32-35 were designated as plasmids pCR-MAΔ12DS (containing the nucleotide sequence of SEQ ID NO: 32), pCR-MAΔ6DS (containing the nucleotide sequence of SEQ ID NO: 33), pCR-MAGLELO (containing the nucleotide sequence of SEQ ID NO: 34) and pCR-MAΔ5DS (containing the nucleotide sequence of SEQ ID NO: 35), respectively.

On the other hand, a HindIII-digested DNA fragment of approximately 1.2 kb obtained from plasmid pURA34 (JP 2001-120276 A) was inserted into the HindIII site of vector pUC18 which had been digested with restriction enzymes EcoRI and SphI, followed by blunt ending and self-ligation. A clone in which the EcoRI site of the vector was on the 5'-side of URA3 was designated as pUC-URA3. Likewise, a SalI- and XhoI-digested DNA fragment of approximately 2.2 kb obtained from YEp13 was inserted into the SalI site of vector pUC18, and a clone in which the EcoRI site of the vector was on the 5'-side of LUE2 was designated as pUC-LEU2.

Next, the plasmid pCR-MAΔ12DS was digested with a restriction enzyme HindIII and, after blunt ending, was further digested with a restriction enzyme XbaI to obtain a DNA fragment of approximately 1.2 kbp, while vector pESC-URA (STRATAGENE) was digested with a restriction enzyme SacI and, after blunt ending, was further digested with a restriction enzyme SpeI to obtain a DNA fragment of approximately 6.6 kbp. These DNA fragments were ligated to obtain plasmid pESC-U-Δ12. The plasmid pCR-MAΔ6DS was digested with a restriction enzyme XbaI and, after blunt ending, was further digested with a restriction enzyme HindIII to obtain a DNA fragment of approximately 1.6 kbp, while the plasmid pESC-U-Δ12 was digested with a restriction enzyme SalI and, after blunt ending, was further digested with a restriction enzyme HindIII to obtain a DNA fragment of approximately 8 kbp. These DNA fragments were ligated to obtain plasmid pESC-U-Δ12:Δ6. This plasmid was partially digested with a restriction enzyme PvuII, and the resulting fragment of approximately 4.2 kb was inserted into the SmaI site of pUC-URA3 to obtain plasmid pUC-URA-Δ12:Δ6.

Likewise, the plasmid pCR-MAGLELO was digested with restriction enzymes XbaI and SacI to obtain a DNA fragment of approximately 0.95 kbp, while vector pESC-LEU (STRATAGENE) was digested with restriction enzymes XbaI and SacI to obtain a DNA fragment of approximately 7.7 kbp. These DNA fragments were ligated to obtain plasmid pESC-L-GLELO. The plasmid pCR-MAΔ5DS was digested with a restriction enzyme XbaI and, after blunt ending, was further digested with a restriction enzyme HindIII to obtain a DNA fragment of approximately 1.3 kbp, while the plasmid pESC-L-GLELO was digested with a restriction enzyme ApaI and, after blunt ending, was further digested with a restriction enzyme HindIII to obtain a DNA fragment of approximately 8.7 kbp. These DNA fragments were ligated to obtain plasmid pESC-L-GLELO:Δ5. This plasmid was digested with a restriction enzyme PvuII, and the resulting fragment of approximately 3.2 kb was inserted into the SmaI site of pUC-LEU2 to obtain plasmid pUC-LEU-GLELO:Δ5. *Saccharomyces cerevisiae* strain YPH499 (STRATAGENE) was co-transformed with plasmid pUC-URA-Δ12:Δ6 and plasmid pUC-LEU-GLELO:Δ5. The transformed strains were screened by the ability to grow on SC-Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine, 6 g threonine and 1.2 g tryptophan). Among the strains thus obtained, any one strain was designated as strain ARA3-1.

(2) Obtaining and Analysis of Transformed Strains of Arachidonic Acid-Producing Yeast The strain ARA3-1 was transformed respectively with plasmids pYE22m, pYE-MALPAAT3 and pYE-MAL-PAAT4. The transformed strains were screened by the ability to grow on SC-Trp,Leu,Ura agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine). Any strains thus obtained were designated as ARA-C, ARA-LPAAT3 and ARA-LPAAT4, respectively.

These strains were each cultured at 30° C. for 1 day in the above SC-Trp,Leu,Ura liquid medium (10 ml), 1 ml of which was then cultured at 30° C. for 2 days in SG-Trp,Leu,Ura liquid medium (10 ml) containing, per liter, 6.7 g Yeast nitrogen base w/o amino acids (DIFCO), 20 g galactose and 1.3 g amino acid powder (a mixture of 1.25 g adenine sulfate, 0.6 g arginine, 3 g aspartic acid, 3 g glutamic acid, 0.6 g histidine, 0.9 g lysine, 0.6 g methionine, 1.5 g phenylalanine, 11.25 g serine, 0.9 g tyrosine, 4.5 g valine and 6 g threonine), followed by analysis of fatty acids in the cells. Tables 5, 6 and 7 show the fatty acid rate in the cells, the fatty acid content in the cells and the arachidonic acid content in the cells, respectively.

TABLE 5

Fatty acid rate in transformed strains

| Sample name | ARA-C | ARA-LPAAT3 | ARA-LPAAT4 |
|---|---|---|---|
| 16:0 | 29.85 | 30.07 | 27.32 |
| 16:1 | 26.88 | 26.82 | 29.81 |
| 18:0 | 10.23 | 10.39 | 9.76 |
| 18:1 | 13.26 | 13.10 | 14.24 |
| 18:1 n-7 | 0.74 | 0.72 | 0.66 |
| 18:2 | 8.06 | 8.17 | 9.22 |
| 18:3(n-6) | 0.28 | 0.25 | 0.25 |
| DGLA | 0.40 | 0.38 | 0.33 |
| AA | 0.16 | 0.16 | 0.20 |
| other | 10.14 | 9.93 | 8.20 |
| total | 100.00 | 100.00 | 100.00 |

TABLE 6

Intracellular fatty acid content in transformed strains

| Sample name | ARA-C | ARA-LPAAT3 | ARA-LPAAT4 |
|---|---|---|---|
| Intracellular fatty acid content (%) | 5.58 | 6.30 | 5.50 |

TABLE 7

Intracellular arachidonic acid content in transformed strains

| | Sample name | | |
|---|---|---|---|
| | ARA-C | ARA-LPAAT3 | ARA-LPAAT4 |
| µg/g | 89.4 | 111.4 | 101.0 |

In the strain ARA-LPAAT4, the ratios of saturated fatty acids, i.e., palmitic acid and stearic acid were decreased, whereas the ratios of linolic acid and arachidonic acid were increased. On the other hand, ARA-LPAAT3 and the control strain showed little difference in their fatty acid rate, but the intracellular fatty acid content was increased in ARA-LPAAT3. Namely, these results indicated that not only the arachidonic acid content in host cells expressing LPAAT3, but also the arachidonic acid content in host cells expressing LPAAT4 was higher than that of the control.

Further, these plasmid-transformed strains were each cultured (n=4 each) at 30° C. for 1 day in the above SC-Trp,Leu, Ura liquid medium (10 ml), 1 ml of which was then inoculated into SG-Trp,Leu,Ura liquid medium (10 ml) and cultured at 15° C. for 7 days, followed by analysis of fatty acids in the cells. Tables 8, 9 and 10 show the fatty acid rate in the cells, the fatty acid content in the cells and the arachidonic acid content in the cells, respectively.

TABLE 8

Intracellular PUFA content in transformed strains
Ratio (%) of PUFA to Intracellular total fatty acid

| Sample name | Control | LPAAT3 | LPAAT4 |
|---|---|---|---|
| 18:2 | 8.37 ± 0.26 | 8.79 ± 0.24 | 9.52 ± 0.28 |
| 18:3(n-6) | 0.54 ± 0.07 | 0.65 ± 0.11 | 0.74 ± 0.07 |
| DGLA | 0.33 ± 0.02 | 0.38 ± 0.07 | 0.25 ± 0.05 |
| ARA | 0.44 ± 0.03 | 0.61 ± 0.06 | 0.48 ± 0.02 |

Mean ± SD

TABLE 9

Intracellular fatty acid content in transformed strains
Intracellular fatty acid content

| Sample name | Control | LPAAT3 | LPAAT4 |
|---|---|---|---|
| (%) | 6.32 ± 0.59 | 7.33 ± 0.70 | 6.45 ± 0.59 |

Mean ± SD

TABLE 10

Intracellular arachidonic acid content in transformed strains
Intracellular arachidonic acid content

| Sample name | Control | LPAAT3 | LPAAT4 |
|---|---|---|---|
| (%) | 0.028 ± 0.003 | 0.045 ± 0.008 | 0.031 ± 0.003 |

Mean ± SD

In a case where *M. alpina*-derived LPAAT3 was expressed in arachidonic acid-producing yeast cells, the ratios of PUFAs including linolic acid, γ-linolenic acid, DGLA and arachidonic acid were increased when compared to the control. Likewise, the intracellular fatty acid content was also increased. On the other hand, when *M. alpina*-derived LPAAT4 was expressed, the ratios of linolic acid and γ-linolenic acid were increased, and the ratio of arachidonic acid was also increased.

Example 9

(1) Vector Construction for *M. alpina* Expression

The vectors used for *M. alpina* expression were pDuraSC which allows expression of a desired gene from the GAPDH promoter, and pDuraMCS which allows expression of a desired gene from the histone promoter.

To express LPAAT3 and LPAAT4 in *M. alpina* cells, vectors were constructed as follows. The plasmid pCR-LPAAT3 or pCR-LPAAT4 was digested with a restriction enzyme EcoRI to excise the insert, which was then inserted into the EcoRI site in the multicloning site of vector pDuraSC or pDura5MCS. The orientation of the inserted DNA was confirmed for each case, and constructs carrying the respective inserts in such an orientation as to cause ORF transcription from the promoter of each vector were designated as plasmid pDuraSC-LPAAT3, plasmid pDuraSC-LPAAT4, plasmid pDura5MCS-LPAAT3 and plasmid pDura5MCS-LPAAT4, respectively.

(2) Obtaining of Transformed *M. alpina* Strains

Uracil-auxotrophic strain Aura-3 derived from *M. alpina* as described in a patent document (WO2005/019437 entitled "Method of Breeding Lipid-Producing Fungus") was used as a host and transformed with these plasmids by the particle delivery method. For screening of the transformed strains, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

(3) Evaluation of *M. alpina* Transformants

The resulting transformed strains were each inoculated into 4 ml GY medium (2% glucose, 1% yeast extract) and cultured with shaking at 28° C. for 3 or 4 days. The cells were collected by filtration, and RNA was extracted with an RNeasy plant kit (QIAGEN). A SuperScript First-Strand system for RT-PCR (Invitrogen) was used to synthesize cDNA. To confirm expression from the introduced construct and total expression for each gene, RT-PCR was performed with the following primer sets.
Strains Transformed with Plasmid pDuraSC-LPAAT3
Primers Used for Expression from the Introduced Construct:

```
Primer MaGAPDHpfw:
CACACCACACATTCAACATC;       (SEQ ID NO: 47)
and

Primer LAT3-2R:
GAATCGTAGATATGGTTGTATCCAGCGCT    (SEQ ID NO: 48)
```

Primers Used for Total Expression of LPAAT3:

```
Primer LAT3-1F:
CTGGCGGTCATCCTTGTTTTCTACCTG;   (SEQ ID NO: 49)
and

Primer LAT3-2R                 (SEQ ID NO: 48)
```

Strains Transformed with Plasmid pDuraSC-LPAAT4
Primers Used for Expression from the Introduced Construct:

```
Primer MaGAPDHpfw;             (SEQ ID NO: 47)
and

Primer LAT4-2R:
GAATCATAGATGTGTGAGTATCCTTGCGA  (SEQ ID NO: 50)
```

Primers Used for Total Expression of LPAAT4:

```
Primer LAT4-1F:
TTCTAATCCTGTCCTACTGGCAGCG;     (SEQ ID NO: 51)
and

Primer LAT4-2R                 (SEQ ID NO: 50)
```

Strains Transformed with Plasmid pDura5MCS-LPAAT3
Primers Used for Expression from the Introduced Construct:

```
Primer PD4P:
CGCATCCCGCAAACACACAC;          (SEQ ID NO: 52)
and

Primer LAT3-2R                 (SEQ ID NO: 48)
```

Primers Used for Total Expression of LPAAT3:
Primer LAT3-1F (SEQ ID NO: 49) and primer LAT3-2R (SEQ ID NO: 48)
Strains Transformed with Plasmid pDura5MCS-LPAAT4
Primers Used for Expression from the Introduced Construct:
Primer PD4P (SEQ ID NO: 52) and primer LAT4-2R (SEQ ID NO: 50)
Primers Used for Total Expression of LPAAT4:
Primer LAT4-1F (SEQ ID NO: 51) and primer LAT4-2R (SEQ ID NO: 50)

Based on the results of the above RT-PCR, transformants showing high level expression of each gene both in expression from the introduced construct and in total expression were selected: strains Gp-LPAAT3-3 and Gp-LPAAT3-29 from those transformed with plasmid pDuraSC-LPAAT3; strains Gp-LPAAT4-26 and Gp-LPAAT4-68 from those transformed with plasmid pDuraSC-LPAAT4; strain Hp-LPAAT3-34 from those transformed with plasmid pDura5MCS-LPAAT3; and strains Hp-LPAAT4-26 and Hp-LPAAT4-31 from those transformed with plasmid pDura5MCS-LPAAT4.

These strains were each cultured with shaking in GY medium (4 ml) at 28° C. at 125 rpm for 3 or 4 days (n=3 each). After completion of the culture, the cells were collected by filtration and lyophilized. A portion (about 10-20 mg) of the dried cells was treated by the hydrochloric acid/methanol method to derive fatty acids in the cells into corresponding methyl esters, followed by extraction with hexane. After distilling off hexane, the fatty acids were analyzed by gas chromatography. The intracellular fatty acid content and the arachidonic acid production per medium are summarized in the tables below.

TABLE 11

Intracellular fatty acid content (%) in *M. alpina* strains highly expressing LPAAT3

| | Gp-LPAAT3-3 | Gp-LPAAT3-29 | Hp-LPAAT3-34 | 1S-4 |
|---|---|---|---|---|
| Day 3 | 22.72 ± 4.35 | 21.52 ± 7.30 | 23.86 ± 5.36 | 19.69 ± 2.22 |
| Day 4 | 29.44 ± 1.61 | 29.33 ± 1.36 | 35.81 ± 0.35 | 24.92 ± 5.62 |

Mean ± SD

TABLE 12

ARA production (g/L) in *M. alpina* strains highly expressing LPAAT3

|       | Gp-LPAAT3-3   | Gp-LPAAT3-29  | Hp-LPAAT3-34  | 1S-4          |
|-------|---------------|---------------|---------------|---------------|
| Day 3 | 0.78 ± 0.20   | 0.69 ± 0.37   | 0.70 ± 0.31   | 0.58 ± 0.06   |
| Day 4 | 1.28 ± 0.09   | 1.19 ± 0.24   | 1.59 ± 0.14   | 0.99 ± 0.26   |

Mean ± SD

TABLE 13

Intracellular fatty acid content (%) in *M. alpina* strains highly expressing LPAAT4

|       | Gp-LPAAT4-26 | Gp-LPAAT4-68 | Hp-LPAAT4-26 | Hp-LPAAT4-31 | 1S-4         |
|-------|--------------|--------------|--------------|--------------|--------------|
| Day 3 | 22.29 ± 2.07 | 26.15 ± 5.35 | 21.41 ± 2.16 | 21.25 ± 1.87 | 19.69 ± 2.22 |
| Day 4 | 35.05 ± 1.30 | 30.88 ± 4.01 | 32.65 ± 2.63 | 32.83 ± 1.73 | 24.92 ± 5.62 |

TABLE 14

ARA production (g/L) in *M. alpina* strains highly expressing LPAAT4

|       | Gp-LPAAT4-26 | Gp-LPAAT4-68 | Hp-LPAAT4-26 | Hp-LPAAT4-31 | 1S-4         |
|-------|--------------|--------------|--------------|--------------|--------------|
| Day 3 | 0.80 ± 0.08  | 0.97 ± 0.29  | 0.79 ± 0.15  | 0.79 ± 0.10  | 0.58 ± 0.06  |
| Day 4 | 1.70 ± 0.16  | 1.50 ± 0.23  | 1.62 ± 0.25  | 1.63 ± 0.05  | 0.99 ± 0.26  |

These results indicated that all the tested transformed *M. alpina* strains showed a higher intracellular fatty acid content and higher arachidonic acid production per medium than the control.

Sequence Listing Free Text
SEQ ID NO: 9: primer
SEQ ID NO: 10: primer
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 21: primer
SEQ ID NO: 22: primer
SEQ ID NO: 24: primer
SEQ ID NO: 25: primer
SEQ ID NO: 26: primer
SEQ ID NO: 27: primer
SEQ ID NO: 28: primer
SEQ ID NO: 29: primer
SEQ ID NO: 30: primer
SEQ ID NO: 31: primer
SEQ ID NO: 38: primer
SEQ ID NO: 39: primer
SEQ ID NO: 45: primer
SEQ ID NO: 46: primer
SEQ ID NO: 47: primer
SEQ ID NO: 48: primer
SEQ ID NO: 49: primer
SEQ ID NO: 50: primer
SEQ ID NO: 51: primer
SEQ ID NO: 52: primer

---

The invention claimed is:

1. An isolated nucleic acid comprising a nucleotide sequence shown in any one of (a) to (e) below:
   (a) a nucleotide sequence which encodes a protein consisting of an amino acid sequence with deletion, substitution, or addition of 1 to 10 amino acids in the amino acid sequence of SEQ ID NO:2 and having lysophosphatidic acid acyltransferase activity;
   (b) a nucleotide sequence which hybridizes under conditions of 0.2×SSC at 63° C. with a nucleic acid consisting of a nucleotide sequence completely complementary to a nucleotide sequence consisting of SEQ ID NO:36 and which encodes a protein having lysophosphatidic acid acyltransferase activity;
   (c) a nucleotide sequence which consists of a nucleotide sequence sharing an identity of 90% or more with a nucleotide sequence consisting of SEQ ID NO:36 and which encodes a protein having lysophosphatidic acid acyltransferase activity;
   (d) a nucleotide sequence which encodes an amino acid sequence sharing an identity of 90% or more with an amino acid sequence consisting of SEQ ID NO:2 and which encodes a protein having lysophosphatidic acid acyltransferase activity; or
   (e) a nucleotide sequence which hybridizes under conditions of 0.2×SSC at 63° C. with a nucleic acid consisting of a nucleotide sequence completely complementary to a nucleotide sequence encoding a protein consisting of the amino acid sequence of SEQ ID NO:2 and which encodes a protein having lysophosphatidic acid acyltransferase activity.

2. An isolated nucleic acid comprising a nucleotide sequence shown in any one of (a) to (c) below:
   (a) the nucleotide sequence of SEQ ID NO:36;
   (b) a nucleotide sequence encoding a protein consisting of the amino acid sequence of SEQ ID NO:2; or
   (c) the nucleotide sequence of SEQ ID NO:1.

3. A recombinant vector comprising the nucleic acid according to claim 1.

4. A transformant transformed with the recombinant vector according to claim 3.

5. A method for preparing a fatty acid composition, which comprises collecting a fatty acid composition obtained by culturing a transformant transformed with a recombinant vector comprising the nucleic acid according to claim 1, wherein the arachidonic acid content in the fatty acid composition is higher than that of a cultured product obtained by culturing a host which is not transformed with the recombinant vector comprising the nucleic acid according to claim 1, from a cultured product obtained by culturing the transformant transformed with a recombinant vector comprising the nucleic acid according to claim 1.

* * * * *

SEQUENCE LISTING

```
<160> NUMBER OF SEQ ID NOS: 53

<210> SEQ ID NO 1
<211> LENGTH: 1207
<212> TYPE: DNA
<213> ORGANISM: Mortierella alpina
<220> FEATURE:
<221> NAME/KEY: CDS
<222> LOCATION: (158)..(1147)

<400> SEQUENCE: 1 cccegtetttt actectgcac acagacacac acccacacte tetetttcct ggtttgaaca      60 gatcccaatt gccgactcca tetttctcca tactcttcac ccctcccate gccctccttt     120
```

```
cacttcctct gtttctcatc tgacgccaat cgtaagg atg tca tca atg tca tca       175
                                         Met Ser Ser Met Ser Ser
                                         1               5 ata gag ccc gca ctg tcc tcg ttt cca ggc aac ctg gcg gtc atc ctt       223
Ile Glu Pro Ala Leu Ser Ser Phe Pro Gly Asn Leu Ala Val Ile Leu
        10              15              20 gtt ttc tac ctg gca ctt cca cga ctt ctt gcc gtc ctg cca caa aag       271
Val Phe Tyr Leu Ala Leu Pro Arg Leu Leu Ala Val Leu Pro Gln Lys
            25              30              35 att cag ttc atc gcc aaa tgt ctc att gtc ctt aca gcc acc ttc ctc       319
Ile Gln Phe Ile Ala Lys Cys Leu Ile Val Leu Thr Ala Thr Phe Leu
    40              45              50 atg tct gtg gca gga tgc ttt gtc gcc att gtc tgt gct ctc ctc caa       367
Met Ser Val Ala Gly Cys Phe Val Ala Ile Val Cys Ala Leu Leu Gln
55              60              65              70 aag cgc tat gcc ata aat tac gtg gtt gcg agg atc ttt tct tat atc       415
Lys Arg Tyr Ala Ile Asn Tyr Val Val Ala Arg Ile Phe Ser Tyr Ile
                75              80              85 gca tgc agg cct tgt gga gtc acg ttc aat atc gtg ggc gaa gaa cac       463
Ala Cys Arg Pro Cys Gly Val Thr Phe Asn Ile Val Gly Glu Glu His
            90              95              100 ctc gag aac act cca gca atc gtt gtc tgc aac cac cag agc tcc atg       511
Leu Glu Asn Thr Pro Ala Ile Val Val Cys Asn His Gln Ser Ser Met
        105             110             115 gat atg atg gtc ttg gga cga gtg ttc cca atg cgc tgc gtg gtt atg       559
Asp Met Met Val Leu Gly Arg Val Phe Pro Met Arg Cys Val Val Met
    120             125             130 gcc aag aag gaa ctt cag tac ttt cca ttt ctc ggc atc ttt atg acg       607
Ala Lys Lys Glu Leu Gln Tyr Phe Pro Phe Leu Gly Ile Phe Met Thr
135             140             145             150 ctg agc aat gcc att ttt att gac cgc aag aat cat aag aag gcc att       655
Leu Ser Asn Ala Ile Phe Ile Asp Arg Lys Asn His Lys Lys Ala Ile
                155             160             165 gag tct aca acc cag gcc gtt gct gac atg aag aag cac aac tct ggg       703
Glu Ser Thr Thr Gln Ala Val Ala Asp Met Lys Lys His Asn Ser Gly
            170             175             180 atc tgg atc ttc ccc gag gga act cgc tcc cgg ctt gac acg gcc gac       751
Ile Trp Ile Phe Pro Glu Gly Thr Arg Ser Arg Leu Asp Thr Ala Asp
        185             190             195 ctg ctg cca ttc aag aag gga gcc ttt cat ctt gca atc cag tca gga       799
Leu Leu Pro Phe Lys Lys Gly Ala Phe His Leu Ala Ile Gln Ser Gly
    200             205             210 ctt ccc atc cta ccc att gtc agc gct gga tac aac cat atc tac gat       847
Leu Pro Ile Leu Pro Ile Val Ser Ala Gly Tyr Asn His Ile Tyr Asp
215             220             225             230 tct gcc aag cga tct ttc cct ggc ggt gag ctc gag atc agg gtt ttg       895
Ser Ala Lys Arg Ser Phe Pro Gly Gly Glu Leu Glu Ile Arg Val Leu
                235             240             245 gag ccc ata cct acc aca ggc atg acg gcc gat gat gtg aac gat ctg       943
Glu Pro Ile Pro Thr Thr Gly Met Thr Ala Asp Asp Val Asn Asp Leu
            250             255             260 atg gag cgg aca cgg gca gtg atg ttg aag aac cta aag gag atg gat       991
Met Glu Arg Thr Arg Ala Val Met Leu Lys Asn Leu Lys Glu Met Asp
        265             270             275 gtc aac tcc ttg gca gta tct tca aaa ccc tcg ctc tca gtg gac gag      1039
Val Asn Ser Leu Ala Val Ser Ser Lys Pro Ser Leu Ser Val Asp Glu
    280             285             290 ctc aag tca gcg ccc gca ctg aag cag gag gcg aag tcg act gcg gtg      1087
Leu Lys Ser Ala Pro Ala Leu Lys Gln Glu Ala Lys Ser Thr Ala Val
295             300             305             310
```

```
gtg gag gaa gag ggg gtt agc tac gac agc gtg aag aag agg aag acg       1135
Val Glu Glu Glu Gly Val Ser Tyr Asp Ser Val Lys Lys Arg Lys Thr
                315                 320                 325 gtc aag gct tag atcgtgggta atggtgatat atgtatttag ttcacgcact           1187
Val Lys Ala attaaaatcc tgatgtcctt                                                 1207

<210> SEQ ID NO 2
<211> LENGTH: 329
<212> TYPE: PRT
<213> ORGANISM: Mortierella alpina

<400> SEQUENCE: 2

Met Ser Ser Met Ser Ser Ile Glu Pro Ala Leu Ser Ser Phe Pro Gly
 1               5                  10                 15

Asn Leu Ala Val Ile Leu Val Phe Tyr Leu Ala Leu Pro Arg Leu Leu
                20                  25                 30

Ala Val Leu Pro Gln Lys Ile Gln Phe Ile Ala Lys Cys Leu Ile Val
                35                  40                 45

Leu Thr Ala Thr Phe Leu Met Ser Val Ala Gly Cys Phe Val Ala Ile
50                  55                  60

Val Cys Ala Leu Leu Gln Lys Arg Tyr Ala Ile Asn Tyr Val Val Ala
65                  70                  75                  80

Arg Ile Phe Ser Tyr Ile Ala Cys Arg Pro Cys Gly Val Thr Phe Asn
                85                  90                  95

Ile Val Gly Glu Glu His Leu Glu Asn Thr Pro Ala Ile Val Val Cys
                100                 105                110

Asn His Gln Ser Ser Met Asp Met Met Val Leu Gly Arg Val Phe Pro
                115                 120                125

Met Arg Cys Val Val Met Ala Lys Lys Glu Leu Gln Tyr Phe Pro Phe
130                 135                 140

Leu Gly Ile Phe Met Thr Leu Ser Asn Ala Ile Phe Ile Asp Arg Lys
145                 150                 155                 160

Asn His Lys Lys Ala Ile Glu Ser Thr Thr Gln Ala Val Ala Asp Met
                165                 170                 175

Lys Lys His Asn Ser Gly Ile Trp Ile Phe Pro Glu Gly Thr Arg Ser
                180                 185                 190

Arg Leu Asp Thr Ala Asp Leu Leu Pro Phe Lys Lys Gly Ala Phe His
                195                 200                 205

Leu Ala Ile Gln Ser Gly Leu Pro Ile Leu Pro Ile Val Ser Ala Gly
                210                 215                 220

Tyr Asn His Ile Tyr Asp Ser Ala Lys Arg Ser Phe Pro Gly Gly Glu
225                 230                 235                 240

Leu Glu Ile Arg Val Leu Glu Pro Ile Pro Thr Thr Gly Met Thr Ala
                245                 250                 255

Asp Asp Val Asn Asp Leu Met Glu Arg Thr Arg Ala Val Met Leu Lys
                260                 265                 270

Asn Leu Lys Glu Met Asp Val Asn Ser Leu Ala Val Ser Ser Lys Pro
                275                 280                 285

Ser Leu Ser Val Asp Glu Leu Lys Ser Ala Pro Ala Leu Lys Gln Glu
                290                 295                 300

Ala Lys Ser Thr Ala Val Val Glu Glu Glu Gly Val Ser Tyr Asp Ser
305                 310                 315                 320

Val Lys Lys Arg Lys Thr Val Lys Ala
                325
```

```
<210> SEQ ID NO 3
<211> LENGTH: 1148
<212> TYPE: DNA
<213> ORGANISM: Mortierella alpina
<220> FEATURE:
<221> NAME/KEY: CDS
<222> LOCATION: (55)..(996)
<220> FEATURE:
<221> NAME/KEY: modified_base
<222> LOCATION: (1140)..(1140)
<223> OTHER INFORMATION: a, c, g, t, unknown or other

<400> SEQUENCE: 3
ctcttccatt caacgatcgt tttcttccct agcacacgtt tctgttcgtc cgac atg        57
                                                            Met
                                                            1 tcc ata ggc tct tct aat cct gtc cta ctg gca gcg atc ccc ttc gtc        105
Ser Ile Gly Ser Ser Asn Pro Val Leu Leu Ala Ala Ile Pro Phe Val
            5                   10                  15 tac ctt ttt gtc ctc cct cgc atc ctc gcc ttc ctc cct caa aag gcc        153
Tyr Leu Phe Val Leu Pro Arg Ile Leu Ala Phe Leu Pro Gln Lys Ala
        20                  25                  30 cag ttc ctc gca aaa tgt atc gtg gtc ttg atc gcc acc ctc atc atg        201
Gln Phe Leu Ala Lys Cys Ile Val Val Leu Ile Ala Thr Leu Ile Met
    35                  40                  45 tcc gtc gca ggc tgc ctc atc tct att gtc tgt gcg ctc ctc gac aaa        249
Ser Val Ala Gly Cys Leu Ile Ser Ile Val Cys Ala Leu Leu Asp Lys
50                  55                  60                  65 cgc tat gtg atc aac tac gtt gtc tca aga ctc ttc tca ttc ctt gca        297
Arg Tyr Val Ile Asn Tyr Val Val Ser Arg Leu Phe Ser Phe Leu Ala
                70                  75                  80 gca aga ccc tgc ggc gtc act tac aag att gtg ggc gag gag cat ttg        345
Ala Arg Pro Cys Gly Val Thr Tyr Lys Ile Val Gly Glu Glu His Leu
            85                  90                  95 gat aag tac ccc gcc att gtc gtt tgc aac cac cag agc tca atg gac        393
Asp Lys Tyr Pro Ala Ile Val Val Cys Asn His Gln Ser Ser Met Asp
        100                 105                 110 atg atg gtt ctg gga cgc gtc ttc cct aag cac tgt gtc gtc atg gca        441
Met Met Val Leu Gly Arg Val Phe Pro Lys His Cys Val Val Met Ala
    115                 120                 125 aag aag gag ctt ctt tac ttt ccg ttc ctg ggc atg ttc atg aaa ctg        489
Lys Lys Glu Leu Leu Tyr Phe Pro Phe Leu Gly Met Phe Met Lys Leu
130                 135                 140                 145 agc aat gcc att ttc atc gac cgc aag aac cat aag aag gcg atc gag        537
Ser Asn Ala Ile Phe Ile Asp Arg Lys Asn His Lys Lys Ala Ile Glu
                150                 155                 160 tct acc acc caa gct gtc gcc gac atg aag aag cac aac tct gga atc        585
Ser Thr Thr Gln Ala Val Ala Asp Met Lys Lys His Asn Ser Gly Ile
            165                 170                 175 tgg att ttc ccc gaa gga aca cgt tcc cgc ttg gac aag gcc gat ctc        633
Trp Ile Phe Pro Glu Gly Thr Arg Ser Arg Leu Asp Lys Ala Asp Leu
        180                 185                 190 ttg ccc ttc aag aag gga gcc ttc cac ctc gcc att caa gct caa ctt        681
Leu Pro Phe Lys Lys Gly Ala Phe His Leu Ala Ile Gln Ala Gln Leu
    195                 200                 205 ccc atc ctc ccc atc gtc tcg caa gga tac tca cac atc tat gat tca        729
Pro Ile Leu Pro Ile Val Ser Gln Gly Tyr Ser His Ile Tyr Asp Ser
210                 215                 220                 225 tca aaa cgc tac ttc ccc ggt gga gag ctc gag atc aga gtc ctg gaa        777
Ser Lys Arg Tyr Phe Pro Gly Gly Glu Leu Glu Ile Arg Val Leu Glu
                230                 235                 240
```

```
ccc atc cct acc aag gga ttg acc aca gac gat gtc aac gac ctg atg      825
Pro Ile Pro Thr Lys Gly Leu Thr Thr Asp Asp Val Asn Asp Leu Met
            245                 250                 255 gac aag aca cgc aac ttg atg ctc aag cac ctc aag gac atg gat tct      873
Asp Lys Thr Arg Asn Leu Met Leu Lys His Leu Lys Asp Met Asp Ser
        260                 265                 270 cat tgc tcc tcc gcc gtc gga aac gga tct ctg cct ctc gac gcc gac      921
His Cys Ser Ser Ala Val Gly Asn Gly Ser Leu Pro Leu Asp Ala Asp
    275                 280                 285 att gca aag tca acg gct aca tcg atc gga aac aca gac gat gct gtc      969
Ile Ala Lys Ser Thr Ala Thr Ser Ile Gly Asn Thr Asp Asp Ala Val
290                 295                 300                 305 aca aag agg agg aca ctg aaa gag taa  aacagcaaca accacaaaca           1016
Thr Lys Arg Arg Thr Leu Lys Glu
                    310 caaccataac cacaaccaca accaccctgc aggatactcc gatccagcat atcgcatcca    1076 aatgcctgta atgtactttt ttttctttaa aaacatgatt aaatcgatag agctgtaccc    1136 attngacaag aa                                                        1148

<210> SEQ ID NO 4
<211> LENGTH: 313
<212> TYPE: PRT
<213> ORGANISM: Mortierella alpina

<400> SEQUENCE: 4

Met Ser Ile Gly Ser Ser Asn Pro Val Leu Ala Ala Ile Pro Phe
1               5                   10                  15

Val Tyr Leu Phe Val Leu Pro Arg Ile Leu Ala Phe Leu Pro Gln Lys
            20                  25                  30

Ala Gln Phe Leu Ala Lys Cys Ile Val Val Leu Ile Ala Thr Leu Ile
        35                  40                  45

Met Ser Val Ala Gly Cys Leu Ile Ser Ile Val Cys Ala Leu Leu Asp
    50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu Glu His
                85                  90                  95

Leu Asp Lys Tyr Pro Ala Ile Val Val Cys Asn His Gln Ser Ser Met
            100                 105                 110

Asp Met Met Val Leu Gly Arg Val Phe Pro Lys His Cys Val Val Met
        115                 120                 125

Ala Lys Lys Glu Leu Leu Tyr Phe Pro Phe Leu Gly Met Phe Met Lys
    130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
            180                 185                 190

Leu Leu Pro Phe Lys Lys Gly Ala Phe His Leu Ala Ile Gln Ala Gln
        195                 200                 205

Leu Pro Ile Leu Pro Ile Val Ser Gln Gly Tyr Ser His Ile Tyr Asp
    210                 215                 220

Ser Ser Lys Arg Tyr Phe Pro Gly Gly Glu Leu Glu Ile Arg Val Leu
225                 230                 235                 240
```

```
Glu Pro Ile Pro Thr Lys Gly Leu Thr Thr Asp Asp Val Asn Asp Leu
                245                 250                 255

Met Asp Lys Thr Arg Asn Leu Met Leu Lys His Leu Lys Asp Met Asp
                260                 265                 270

Ser His Cys Ser Ser Ala Val Gly Asn Gly Ser Leu Pro Leu Asp Ala
            275                 280                 285

Asp Ile Ala Lys Ser Thr Ala Thr Ser Ile Gly Asn Thr Asp Asp Ala
    290                 295                 300

Val Thr Lys Arg Arg Thr Leu Lys Glu
305                 310

<210> SEQ ID NO 5
<211> LENGTH: 843
<212> TYPE: DNA
<213> ORGANISM: Mortierella alpina
<220> FEATURE:
<221> NAME/KEY: modified_base
<222> LOCATION: (793)..(793)
<223> OTHER INFORMATION: a, c, g, t, unknown or other

<400> SEQUENCE: 5
gcgccattga ggagaacctg ggacgtgtca aggaaaagga tccactctgg ctggtagtct      60
tccctgaagg aacagtcgtc tccaaggaaa cgcgtttgcg atctgttgcc ttttcaaaga    120
aggctggtct ttcggatcac cgccatgtgt tgcttccaag aaccagcggc tctttgttt    180 gcatcaacaa gttgcgtgga tccgtcgaat acttatacga cgcgacagtt ggctactcga    240
acgttgaata tggagagatt ccacaggagc tttacccttt gccagggcta tatatcaaca    300
aggcgcagcc caaggagatc aacatgcacc tgcggcggtt tgctatcaag gatatcccca    360
cgtcagaacc cgagtttgtg gagtgggtcc gagcgcggtg ggtagagaag gatgagctga    420
tggaggagtt ttataccaag ggccgattcc catcgcagct gacggctgag acattggcg     480 agaaggagac caacaaggca ggaggctcat ctgaaggaca gagtgtcaga atcccgctca    540
aatcgcgagg catgatggac tacctcatgc cttcggccat taacctggtt gcgctgccag    600
tactggcttt tgcgatgaga tatgctctgc agcaagtatc gtctggttga tttatttttt    660
gttagacgct gccgtagttg taaatttgat gagtgctatt tagagcaaac gaaagaagag    720
acttaaacgc atggatgtgt gtaatttcat aacagaaaaa aaaaaaaaa aaaaaaaaaa    780 aacctgcagc ccnggggat ccactagttc tagagcgccg ccaccgcggt ggagctcagc     840
gtt                                                                  843

<210> SEQ ID NO 6
<211> LENGTH: 624
<212> TYPE: DNA
<213> ORGANISM: Mortierella alpina

<400> SEQUENCE: 6
tctaaaaaaa atatgctgca tgttttcctt gtcagtggtg gtcgctcacc acttctctga     60
ccagacacct ccttcaatac ccgtctgtcc agttctcctt catttgctct aagaaggcgt    120
ccttctccac gtacttctga accacccact cgctcagctt ctcttcatct acgggcagat    180
cgtcgagctg atagcgtctc acatgcacat gaaacttgta ctcggggctg agctgaccag    240
tgtgaacacg caccagatct ggggcactc caaaaccctt ggtcttgtgg taataggcaa    300
acgtgaagtc gtaaacacac ttcacatgag ttcctcggaa tttgttgacg caggcaatga    360
atcccttggt cctgggcatc atgacattcg agagcagagg caggccgcgt cccagcatga    420
```

| | |
|---|---|
| acttttgaga ggcagccagc ttgctaggcg tcagacgaga accctccagg aaactggcga | 480 |
| cccagaccgg tgcttggata tccaatatcc gcgcaaacat cttgttgatc ttgagctgat | 540 |
| cctgctgcca gttgcggttg atgaacagca ttcccatgat ccacatgccc catccgtaga | 600 |
| atggaatgta tttcacagaa tcct | 624 |

<210> SEQ ID NO 7
<211> LENGTH: 690
<212> TYPE: DNA
<213> ORGANISM: Mortierella alpina

<400> SEQUENCE: 7

| | |
|---|---|
| ctcttccatt caacgatcgt tttcttccct agcacacgtt tctgttcgtc cgacatgtcc | 60 |
| ataggctctt ctaatcctgt cctactggca gcgatcccct tcgtctacct ttttgtcctc | 120 |
| cctcgcatcc tcgccttcct ccctcaaaag gcccagttcc tcgcaaaatg tatcgtggtc | 180 |
| ttgatcgcca ccctcatcat gtccgtcgca ggctgcctca tctctattgt ctgtgcgctc | 240 |
| ctcgacaaac gctatgtgat caactacgtt gtctcaagac tcttctcatt ccttgcagca | 300 |
| agaccctgcg gcgtcactta caagattgtg ggcgaggagc atttggataa gtaccccgcc | 360 |
| attgtcgttt gcaaccacca gagctcaatg gacatgatgg ttctgggacg cgtcttccct | 420 |
| aagcactgtg tcgtcatggc aaagaaggag cttctttact ttccgttcct gggcatgttc | 480 |
| atgaaactga gcaatgccat tttcatcgac cgcaagaacc ataagaaggc gatcgagtct | 540 |
| accacccaag ctgtcgccga catgaagaag cacaactctg gaatctggat ttttccccgaa | 600 |
| ggaacacgtt cccgcttgga caaggccgat ctcttgccct tcaagaaggg agccttccaa | 660 |
| ctcgccattc aagctcaact tcccatcctc | 690 |

<210> SEQ ID NO 8
<211> LENGTH: 990
<212> TYPE: DNA
<213> ORGANISM: Mortierella alpina

<400> SEQUENCE: 8

| | |
|---|---|
| atgtcatcaa tgtcatcaat agagcccgca ctgtcctcgt ttccaggcaa cctggcggtc | 60 |
| atccttgttt tctacctggc acttccacga cttcttgccg tcctgccaca aaagattcag | 120 |
| ttcatcgcca aatgtctcat tgtccttaca gccaccttcc tcatgtctgt ggcaggatgc | 180 |
| tttgtcgcca ttgtctgtgc tctcctccaa aagcgctatg ccataaatta cgtggttgcg | 240 |
| aggatctttt cttatatcgc atgcaggcct tgtggagtca cgttcaatat cgtgggcgaa | 300 |
| gaacacctcg agaacactcc agcaatcgtt gtctgcaacc accagagctc catggatatg | 360 |
| atggtcttgg gacgagtgtt cccaatgcgc tgcgtggtta tggccaagaa ggaacttcag | 420 |
| tactttccat ttctcggcat ctttatgacg ctgagcaatg ccatttttat tgaccgcaag | 480 |
| aatcataaga aggccattga gtctacaacc caggccgttg ctgacatgaa gaagcacaac | 540 |
| tctgggatct ggatcttccc cgagggaact cgctcccggc ttgacacggc cgacctgctg | 600 |
| ccattcaaga agggagcctt tcatcttgca atccagtcag acttcccat cctacccatt | 660 |
| gtcagcgctg gatacaacca tatctacgat tctgccaagc gatctttccc tggcggtgag | 720 |
| ctcgagatca gggttttgga gcccataccl accacaggca tgacggccga tgatgtgaac | 780 |
| gatctgatgg agcggacacg ggcagtgatg ttgaagaacc taaggagat ggatgtcaac | 840 |
| tccttggcag tatcttcaaa accctcgctc tcagtggacg agctcaagtc agcgcccgca | 900 |
| ctgaagcagg aggcgaagtc gactgcggtg gtggaggaag aggggggttag ctacgacagc | 960 | gtgaagaaga ggaagacggt caaggcttag                                            990

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggatgtcatc aatgtcatca atagag                                                26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 ctaacccct cttcctccac cac                                                    23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggacgtgtca aggaaaagga                                                       20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccttcagat gagcctcctg                                                       20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgtccttc tccacgtact tc                                                    22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgaaataca ttccattcta cg                                                    22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cctcgcaaaa tgtatcgtgg				20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gatgggaagt tgagcttgaa tg			22

<210> SEQ ID NO 17
<211> LENGTH: 1369
<212> TYPE: DNA
<213> ORGANISM: Mortierella alpina
<220> FEATURE:
<221> NAME/KEY: CDS
<222> LOCATION: (36)..(1289)

<400> SEQUENCE: 17

```
tctcgagctc tagcaactct tctagcgcaa cgctc atg gat gaa tcc acc acc        53
                                     Met Asp Glu Ser Thr Thr
                                      1               5 acc acc cac cac aca gag acc agc agc aag acg tcc tcg cac ccc cgt       101
Thr Thr His His Thr Glu Thr Ser Ser Lys Thr Ser Ser His Pro Arg
         10                  15                  20 cgg ctc ggt ccc aag atg aac ccc atc tac aag ggt ctg cga gcc ttt       149
Arg Leu Gly Pro Lys Met Asn Pro Ile Tyr Lys Gly Leu Arg Ala Phe
 25                  30                  35 gtc tgg gcc ttg tac ttc aac cta gga gca tct ctc ata tcg ata acc       197
Val Trp Ala Leu Tyr Phe Asn Leu Gly Ala Ser Leu Ile Ser Ile Thr
 40                  45                  50 caa gtc ctg tcg ttg cct ctg gcg ttg atc gct cca aaa gtt tac cag       245
Gln Val Leu Ser Leu Pro Leu Ala Leu Ile Ala Pro Lys Val Tyr Gln
55                  60                  65                  70 tgg cac atc act aaa acc cag ggt cac ttt ggg gct ttc ctg ctc aag       293
Trp His Ile Thr Lys Thr Gln Gly His Phe Gly Ala Phe Leu Leu Lys
                 75                  80                  85 atg aac cag cta ttt gcg ccc tca gat atc gtt ttg acg gga gat gaa       341
Met Asn Gln Leu Phe Ala Pro Ser Asp Ile Val Leu Thr Gly Asp Glu
             90                  95                 100 agt gtc agg gga atc gtc aag gtg tac caa gga cga agg ctg aag gac       389
Ser Val Arg Gly Ile Val Lys Val Tyr Gln Gly Arg Arg Leu Lys Asp
        105                 110                 115 act ggt gag gcg tac agc ggt cat gga gag gac att att ctg gat atg       437
Thr Gly Glu Ala Tyr Ser Gly His Gly Glu Asp Ile Ile Leu Asp Met
    120                 125                 130 ccc gag agg atg gtt ttc atc gcg aac cac cag atc tat tct gac tgg       485
Pro Glu Arg Met Val Phe Ile Ala Asn His Gln Ile Tyr Ser Asp Trp
135                 140                 145                 150 atg tac ctc tgg tgc ttc tcc tat ttc gca gag agg cac agg gca ctg       533
Met Tyr Leu Trp Cys Phe Ser Tyr Phe Ala Glu Arg His Arg Ala Leu
                155                 160                 165
```

```
aag att att ctt cgg ggc gac ctg acc tgg atc cct gtc ttt ggc tgg        581
Lys Ile Ile Leu Arg Gly Asp Leu Thr Trp Ile Pro Val Phe Gly Trp
        170                 175                 180 ggt atg cgg ttc ttt gac ttt atc ttt ttg aaa cgt aat gac tgg gca        629
Gly Met Arg Phe Phe Asp Phe Ile Phe Leu Lys Arg Asn Asp Trp Ala
185                 190                 195 cat gac aga cgc gcc att gag gag aac ctg gga cgt gtc aag gaa aag        677
His Asp Arg Arg Ala Ile Glu Glu Asn Leu Gly Arg Val Lys Glu Lys
        200                 205                 210 gat cca ctc tgg ctg gta gtc ttc cct gaa gga aca gtc gtc tcc aag        725
Asp Pro Leu Trp Leu Val Val Phe Pro Glu Gly Thr Val Val Ser Lys
215                 220                 225                 230 gaa acg cgt ttg cga tct gtt gcc ttt tca aag aag gct ggt ctt tcg        773
Glu Thr Arg Leu Arg Ser Val Ala Phe Ser Lys Lys Ala Gly Leu Ser
                235                 240                 245 gat cac cgc cat gtg ttg ctt cca aga acc agc ggc ctc ttt gtt tgc        821
Asp His Arg His Val Leu Leu Pro Arg Thr Ser Gly Leu Phe Val Cys
            250                 255                 260 atc aac aag ttg cgt gga tcc gtc gaa tac tta tac gac gcg aca gtt        869
Ile Asn Lys Leu Arg Gly Ser Val Glu Tyr Leu Tyr Asp Ala Thr Val
        265                 270                 275 ggc tac tcg aac gtt gaa tat gga gag att cca cag gag ctt tac cct        917
Gly Tyr Ser Asn Val Glu Tyr Gly Glu Ile Pro Gln Glu Leu Tyr Pro
280                 285                 290 ttg cca ggg cta tat atc aac aag gcg cag ccc aag gag atc aac atg        965
Leu Pro Gly Leu Tyr Ile Asn Lys Ala Gln Pro Lys Glu Ile Asn Met
295                 300                 305                 310 cac ctg cgg cgg ttt gct atc aag gat atc ccc acg tca gaa ccc gag       1013
His Leu Arg Arg Phe Ala Ile Lys Asp Ile Pro Thr Ser Glu Pro Glu
                315                 320                 325 ttt gtg gag tgg gtc cga gcg cgg tgg gta gag aag gat gag ctg atg       1061
Phe Val Glu Trp Val Arg Ala Arg Trp Val Glu Lys Asp Glu Leu Met
            330                 335                 340 gag gag ttt tat acc aag ggc cga ttc cca tcg cag ctg acg gct gag       1109
Glu Glu Phe Tyr Thr Lys Gly Arg Phe Pro Ser Gln Leu Thr Ala Glu
        345                 350                 355 gac att ggc gag aag gag acc aac aag gca gga ggc tca tct gaa gga       1157
Asp Ile Gly Glu Lys Glu Thr Asn Lys Ala Gly Gly Ser Ser Glu Gly
360                 365                 370 cag agt gtc aga atc ccg ctc aaa tcg cga ggc atg atg gac tac ctc       1205
Gln Ser Val Arg Ile Pro Leu Lys Ser Arg Gly Met Met Asp Tyr Leu
375                 380                 385                 390 atg cct tcg gcc att aac ctg gtt gcg ctg cca gta ctg gct ttt gcg       1253
Met Pro Ser Ala Ile Asn Leu Val Ala Leu Pro Val Leu Ala Phe Ala
                395                 400                 405 atg aga tat gct ctg cag caa gta tcg tct ggt tga tttatttttt          1299
Met Arg Tyr Ala Leu Gln Gln Val Ser Ser Gly
            410                 415 gttagacgct gccgtagttg taaatttgat gagtgctatt tagagcaaac gaaagaagag    1359
acttaaacgc                                                           1369

<210> SEQ ID NO 18
<211> LENGTH: 417
<212> TYPE: PRT
<213> ORGANISM: Mortierella alpina

<400> SEQUENCE: 18

Met Asp Glu Ser Thr Thr Thr Thr His His Thr Glu Thr Ser Ser Lys
1               5                   10                  15
```

-continued

```
Thr Ser Ser His Pro Arg Arg Leu Gly Pro Lys Met Asn Pro Ile Tyr
             20                  25                  30

Lys Gly Leu Arg Ala Phe Val Trp Ala Leu Tyr Phe Asn Leu Gly Ala
         35                  40                  45

Ser Leu Ile Ser Ile Thr Gln Val Leu Ser Leu Pro Leu Ala Leu Ile
 50                  55                  60

Ala Pro Lys Val Tyr Gln Trp His Ile Thr Lys Thr Gln Gly His Phe
 65                  70                  75                  80

Gly Ala Phe Leu Leu Lys Met Asn Gln Leu Phe Ala Pro Ser Asp Ile
                 85                  90                  95

Val Leu Thr Gly Asp Glu Ser Val Arg Gly Ile Val Lys Val Tyr Gln
            100                 105                 110

Gly Arg Arg Leu Lys Asp Thr Gly Glu Ala Tyr Ser Gly His Gly Glu
        115                 120                 125

Asp Ile Ile Leu Asp Met Pro Glu Arg Met Val Phe Ile Ala Asn His
130                 135                 140

Gln Ile Tyr Ser Asp Trp Met Tyr Leu Trp Cys Phe Ser Tyr Phe Ala
145                 150                 155                 160

Glu Arg His Arg Ala Leu Lys Ile Ile Leu Arg Gly Asp Leu Thr Trp
                165                 170                 175

Ile Pro Val Phe Gly Trp Gly Met Arg Phe Phe Asp Phe Ile Phe Leu
            180                 185                 190

Lys Arg Asn Asp Trp Ala His Asp Arg Arg Ala Ile Glu Glu Asn Leu
        195                 200                 205

Gly Arg Val Lys Glu Lys Asp Pro Leu Trp Leu Val Val Phe Pro Glu
210                 215                 220

Gly Thr Val Val Ser Lys Glu Thr Arg Leu Arg Ser Val Ala Phe Ser
225                 230                 235                 240

Lys Lys Ala Gly Leu Ser Asp His Arg His Val Leu Leu Pro Arg Thr
                245                 250                 255

Ser Gly Leu Phe Val Cys Ile Asn Lys Leu Arg Gly Ser Val Glu Tyr
            260                 265                 270

Leu Tyr Asp Ala Thr Val Gly Tyr Ser Asn Val Glu Tyr Gly Glu Ile
        275                 280                 285

Pro Gln Glu Leu Tyr Pro Leu Pro Gly Leu Tyr Ile Asn Lys Ala Gln
290                 295                 300

Pro Lys Glu Ile Asn Met His Leu Arg Arg Phe Ala Ile Lys Asp Ile
305                 310                 315                 320

Pro Thr Ser Glu Pro Glu Phe Val Glu Trp Val Arg Ala Arg Trp Val
                325                 330                 335

Glu Lys Asp Glu Leu Met Glu Glu Phe Tyr Thr Lys Gly Arg Phe Pro
            340                 345                 350

Ser Gln Leu Thr Ala Glu Asp Ile Gly Glu Lys Glu Thr Asn Lys Ala
        355                 360                 365

Gly Gly Ser Ser Glu Gly Gln Ser Val Arg Ile Pro Leu Lys Ser Arg
370                 375                 380

Gly Met Met Asp Tyr Leu Met Pro Ser Ala Ile Asn Leu Val Ala Leu
385                 390                 395                 400

Pro Val Leu Ala Phe Ala Met Arg Tyr Ala Leu Gln Gln Val Ser Ser
                405                 410                 415

Gly
```

<210> SEQ ID NO 19
<211> LENGTH: 1050

```
<212> TYPE: DNA
<213> ORGANISM: Mortierella alpina
<220> FEATURE:
<221> NAME/KEY: CDS
<222> LOCATION: (26)..(949)

<400> SEQUENCE: 19
ggttcaacac actccgcttc ccggc atg ctc gag tcc gtc acc cga ccc aca         52
                              Met Leu Glu Ser Val Thr Arg Pro Thr
                              1               5 aag gcc ctg ctc tat gga tca gcc ctc ttc agt ttc tgc tcg ttg ctc        100
Lys Ala Leu Leu Tyr Gly Ser Ala Leu Phe Ser Phe Cys Ser Leu Leu
 10              15                  20                  25 aat gtg gtc cag gtg ttc tcg ctg ctc ctg cag ccg ttc tcg aag cgt        148
Asn Val Val Gln Val Phe Ser Leu Leu Leu Gln Pro Phe Ser Lys Arg
                 30                  35                  40 ctc ttc ttt gaa gtg aac gcc cgc gtg gct ggc tcc atg tgg aaa gtc        196
Leu Phe Phe Glu Val Asn Ala Arg Val Ala Gly Ser Met Trp Lys Val
             45                  50                  55 atg cag ttg atc atg gag aaa aaa cac aag gct gcc atc acc ttc tca        244
Met Gln Leu Ile Met Glu Lys Lys His Lys Ala Ala Ile Thr Phe Ser
         60                  65                  70 gga gac aag atc cca cac cac gag agt gct atc gtc ttt ggc aac cac        292
Gly Asp Lys Ile Pro His His Glu Ser Ala Ile Val Phe Gly Asn His
 75                  80                  85 cga tcc ttt gtt gac ttt tac atg ttt cac acc gtt gct gct cgg agg        340
Arg Ser Phe Val Asp Phe Tyr Met Phe His Thr Val Ala Ala Arg Arg
 90                  95                 100                 105 ggc atg ctc aat tac atg aag tac ttt gcc aag gat tct ttg aaa tac        388
Gly Met Leu Asn Tyr Met Lys Tyr Phe Ala Lys Asp Ser Leu Lys Tyr
             110                 115                 120 att cca ttc tac gga tgg ggc atg tgg atc atg gga atg ctg ttc atc        436
Ile Pro Phe Tyr Gly Trp Gly Met Trp Ile Met Gly Met Leu Phe Ile
         125                 130                 135 aac cgc aac tgg cag cag gat cag ctc aag atc aac aag atg ttt gcg        484
Asn Arg Asn Trp Gln Gln Asp Gln Leu Lys Ile Asn Lys Met Phe Ala
     140                 145                 150 cgg ata ttg gat atc caa gca ccg gtc tgg gtc gcc agt ttc ctg gag        532
Arg Ile Leu Asp Ile Gln Ala Pro Val Trp Val Ala Ser Phe Leu Glu
155                 160                 165 ggt tct cgt ctg acg cct agc aag ctg gct gcc tct caa aag ttc atg        580
Gly Ser Arg Leu Thr Pro Ser Lys Leu Ala Ala Ser Gln Lys Phe Met
170                 175                 180                 185 ctg gga cgc ggc ctg cct ctg ctc tcg aat gtc atg atg ccc agg acc        628
Leu Gly Arg Gly Leu Pro Leu Leu Ser Asn Val Met Met Pro Arg Thr
             190                 195                 200 aag gga ttc att gcc tgc gtc aac aaa ttc cga gga act cat gtg aag        676
Lys Gly Phe Ile Ala Cys Val Asn Lys Phe Arg Gly Thr His Val Lys
         205                 210                 215 tgt gtt tac gac ttc acg ttt gcc tat tac cac aag acc aag ggt ttt        724
Cys Val Tyr Asp Phe Thr Phe Ala Tyr Tyr His Lys Thr Lys Gly Phe
     220                 225                 230 gga gtg ccc cca gat ctg gtg cgt gtt cac act ggt cag ctc agc ccc        772
Gly Val Pro Pro Asp Leu Val Arg Val His Thr Gly Gln Leu Ser Pro
235                 240                 245 gag tac aag ttt cat gtg cat gtg aga cgc tat cag ctc gac gat ctg        820
Glu Tyr Lys Phe His Val His Val Arg Arg Tyr Gln Leu Asp Asp Leu
250                 255                 260                 265 ccc gta gat gaa gag aag ctg agc gag tgg gtg gtt cag aag tac gtg        868
Pro Val Asp Glu Glu Lys Leu Ser Glu Trp Val Val Gln Lys Tyr Val
             270                 275                 280
```

-continued

```
gag aag gac gcc ttc tta gag caa atg aag gag aac tgg aca gac ggt    916
Glu Lys Asp Ala Phe Leu Glu Gln Met Lys Glu Asn Trp Thr Asp Gly
            285                 290                 295 att gaa gga ggt gtc tgg tca gag aag tgg tga gcgaccacca ctgacaagaa  969
Ile Glu Gly Gly Val Trp Ser Glu Lys Trp
300                 305 aaacatgcag catatttttt ttagaggaat gaataagaat tgttatattt ataaaggcaa 1029 actatcgccg attacaaagt c                                           1050

<210> SEQ ID NO 20
<211> LENGTH: 307
<212> TYPE: PRT
<213> ORGANISM: Mortierella alpina

<400> SEQUENCE: 20

Met Leu Glu Ser Val Thr Arg Pro Thr Lys Ala Leu Leu Tyr Gly Ser
1               5                   10                  15

Ala Leu Phe Ser Phe Cys Ser Leu Leu Asn Val Gln Val Phe Ser
            20                  25                  30

Leu Leu Leu Gln Pro Phe Ser Lys Arg Leu Phe Phe Glu Val Asn Ala
        35                  40                  45

Arg Val Ala Gly Ser Met Trp Lys Val Met Gln Leu Ile Met Glu Lys
50                  55                  60

Lys His Lys Ala Ala Ile Thr Phe Ser Gly Asp Lys Ile Pro His His
65                  70                  75                  80

Glu Ser Ala Ile Val Phe Gly Asn His Arg Ser Phe Val Asp Phe Tyr
                85                  90                  95

Met Phe His Thr Val Ala Ala Arg Arg Gly Met Leu Asn Tyr Met Lys
            100                 105                 110

Tyr Phe Ala Lys Asp Ser Leu Lys Tyr Ile Pro Phe Tyr Gly Trp Gly
        115                 120                 125

Met Trp Ile Met Gly Met Leu Phe Ile Asn Arg Asn Trp Gln Gln Asp
    130                 135                 140

Gln Leu Lys Ile Asn Lys Met Phe Ala Arg Ile Leu Asp Ile Gln Ala
145                 150                 155                 160

Pro Val Trp Val Ala Ser Phe Leu Glu Gly Ser Arg Leu Thr Pro Ser
                165                 170                 175

Lys Leu Ala Ala Ser Gln Lys Phe Met Leu Gly Arg Gly Leu Pro Leu
            180                 185                 190

Leu Ser Asn Val Met Met Pro Arg Thr Lys Gly Phe Ile Ala Cys Val
        195                 200                 205

Asn Lys Phe Arg Gly Thr His Val Lys Cys Val Tyr Asp Phe Thr Phe
    210                 215                 220

Ala Tyr Tyr His Lys Thr Lys Gly Phe Gly Val Pro Pro Asp Leu Val
225                 230                 235                 240

Arg Val His Thr Gly Gln Leu Ser Pro Glu Tyr Lys Phe His Val His
                245                 250                 255

Val Arg Arg Tyr Gln Leu Asp Asp Leu Pro Val Asp Glu Glu Lys Leu
            260                 265                 270

Ser Glu Trp Val Val Gln Lys Tyr Val Glu Lys Asp Ala Phe Leu Glu
        275                 280                 285

Gln Met Lys Glu Asn Trp Thr Asp Gly Ile Glu Gly Gly Val Trp Ser
    290                 295                 300

Glu Lys Trp
305
```

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catgtccata ggctcttcta atcc                                              24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttttactct ttcagtgtcc tcc                                               23

<210> SEQ ID NO 23
<211> LENGTH: 942
<212> TYPE: DNA
<213> ORGANISM: Mortierella alpina

<400> SEQUENCE: 23
atgtccatag gctcttctaa tcctgtccta ctggcagcga tcccccttcgt ctaccttttt      60
gtcctccctc gcatcctcgc cttcctccct caaaaggccc agttcctcgc aaaatgtatc     120
gtggtcttga tcgccaccct catcatgtcc gtcgcaggct gcctcatctc tattgtctgt     180
gcgctcctcg acaaacgcta tgtgatcaac tacgttgtct caagactctt ctcattcctt     240
gcagcaagac cctgcggcgt cacttacaag attgtgggcg aggagcattt ggataagtac     300
cccgccattg tcgtttgcaa ccaccagagc tcaatggaca tgatggttct gggacgcgtc     360
ttccctaagc actgtgtcgt catggcaaag aaggagcttc tttactttcc gttcctgggc     420
atgttcatga aactgagcaa tgccattttc atcgaccgca gaaccataa gaaggcgatc      480
gagtctacca cccaagctgt cgccgacatg aagaagcaca actctggaat ctggattttc     540
cccgaaggaa cacgttcccg cttggacaag gccgatctct tgcccttcaa gaagggagcc     600
ttccacctcg ccattcaagc tcaacttccc atcctcccca tcgtctcgca aggatactca     660
cacatctatg attcatcaaa acgctacttc cccggtggag agctcgagat cagagtcctg     720
gaacccatcc ctaccaaggg attgaccaca gacgatgtca acgacctgat ggacaagaca     780
cgcaacttga tgctcaagca cctcaaggac atggattctc attgctcctc cgccgtcgga     840
aacggatctc tgcctctcga cgccgacatt gcaaagtcaa cggctacatc gatcggaaac     900
acagacgatg ctgtcacaaa gaggaggaca ctgaaagagt aa                        942

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tctagaatgg cacctcccaa cactattg                                          28

-continued

```
<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aagcttttac ttcttgaaaa agaccacgtc                                   30

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tctagaatgg ctgctgctcc cagtgtgag                                    29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aagcttttac tgtgccttgc ccatcttgg                                    29

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctagaatgg agtcgattgc gcaattcc                                     28

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gagctcttac tgcaacttcc ttgccttctc                                   30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctagaatgg gtgcggacac aggaaaaacc                                   30

<210> SEQ ID NO 31
<211> LENGTH: 30
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagcttttac tcttccttgg gacgaagacc                                        30

<210> SEQ ID NO 32
<211> LENGTH: 1203
<212> TYPE: DNA
<213> ORGANISM: Mortierella alpina

<400> SEQUENCE: 32
atggcacctc ccaacactat tgatgccggt ttgacccagc gccatatcag cacctcggcc      60
gccccaacct ctgccaagcc cgccttcgag cgcaactacc agctccctga gttcaccatc     120
aaggagatcc gtgagtgcat ccctgcacac tgctttgagc gctccggtct ccgtggtctt     180
tgccacgttg ctattgatct gacctgggcc tcgctcttgt tcctggctgc gacccagatc     240
gacaagttcg agaacccttt gatccgctac ttggcctggc ctgcgtattg gatcatgcag     300
ggtattgttt gcaccggtat ctgggtattg gcacacgaat gtggtcatca gtccttctcg     360
acctccaaga cccttaacaa cactgtcggc tggatcttgc actcgatgct cttggtccct     420
taccactcct ggagaatctc gcactcgaag caccacaagg ccactggcca catgaccaag     480
gaccaggtct tgttcccaa gacccgctct caggttggct gcccccaa ggagaatgtt       540 gcagttgccg ttcaggagga ggatatgtcc gtgcacctgg atgaggaggc ccccattgtg     600
actttgttct ggatggtgat tcagttcctg ttcggatggc ctgcgtacct tattatgaac     660
gcctctggtc aagactatgg ccgctggacc tcgcacttcc acacctactc tcctatcttt     720
gagccccgca actttttcga cattatcatt tcggatctcg gtgtgttggc tgctcttggt     780
accttgatct acgcctccat gcagctctcg ctcttgaccg tgaccaagta ctacattgtc     840
ccctacttgt ttgtcaactt ctggttggtc ctgatcacct tcttgcagca caccgacccT    900
aagctgcccc attaccgtga gggtgcctgg aacttccagc gtggagccct ctgcaccgtt    960
gaccgctcgt tcggcaagtt cttggaccat atgttccacg gcattgtcca tacccatgta   1020
gcccatcact tgttctcgca gatgccgttc taccatgctg aggaagccac ccatcatctc   1080
aagaaactgc tgggagagta ctacgtctat gacccatcgc cgattgttgt tgcggtctgg   1140
aggtcgttcc gtgaatgccg attcgtggaa gaccatggag acgtggtctt tttcaagaag   1200
taa                                                                  1203

<210> SEQ ID NO 33
<211> LENGTH: 1374
<212> TYPE: DNA
<213> ORGANISM: Mortierella alpina

<400> SEQUENCE: 33
atggctgctg ctcccagtgt gaggacgttt actcgggccg agattttgaa tgccgaggcc      60
ctgaatgagg gcaagaagga tgccgaggca ccctttctga tgatcattga caacaaggtg     120
tacgatgtcc gcgagtttgt ccctgatcat cccggtggaa gtgtgattct cacgcacgtt     180
ggcaaggacg gcactgacgt ctttgacact ttccaccccg aggctgcttg ggagactctt     240
gccaactttt acgttggtga tattgatgag agcgatcgtg ccatcaagaa tgatgacttt     300
gcggccgagg ttcgcaagct gcgcaccttg ttccagtccc ttggctacta cgactcgtcc     360
```

```
aaggcatact atgccttcaa ggtctcgttc aacctctgca tctggggctt gtcgactttc     420
attgttgcca agtggggcca gacctcgacc ctcgccaacg tgctctcggc tgcgctcttg     480
ggtctcttct ggcagcagtg cggatggttg gcgcacgact ttttgcacca ccaggtcttc     540
caggaccgtt tctggggtga tcttttcggc gccttcttgg gaggtgtctg ccagggtttc     600
tcgtcctcct ggtggaagga caagcacaac actcaccacg ctgctcccaa cgtccacggc     660
gaggatcccg acattgacac tcaccctctg ttgacctgga gtgagcatgc tctggagatg     720
ttctcggatg ttcctgacga ggagctgacc cgtatgtggt cgcgcttcat ggtcctcaac     780
cagacctggt tctacttccc cattctctcg tttgcccgtc tgtcctggtg cctccagtcc     840
attatgcttg ttctgcccaa cggtcaggcc cacaagccct ctggagcgcg tgtgcccatt     900
tcgttggtcg agcagctgtc tctggctatg cactggacct ggtacctcgc caccatgttc     960
ctgttcatta aggatcccgt caacatgatt gtgtactttt tggtgtcgca ggctgtttgc    1020
ggcaacttgt tggcgattgt gttctcgctc aaccacaacg gcatgcctgt gatctccaag    1080
gaggaagcgg tcgatatgga cttcttcacc aagcagatca tcacgggtcg tgatgttcac    1140
cctggtctgt tgccaactg gttcacgggt ggattgaact accagattga gcaccacttg    1200
ttcccttcga tgccccgcca caacttttca agatccagc ctgctgtcga gactttgtgc     1260
aaaaagtacg gtgtccgata ccataccact ggtatgatcg agggaactgc agaggtcttt    1320
agccgtttga acgaggtctc caaggcggcc tccaagatgg gcaaggcaca gtaa          1374

<210> SEQ ID NO 34
<211> LENGTH: 957
<212> TYPE: DNA
<213> ORGANISM: Mortierella alpina

<400> SEQUENCE: 34
atggagtcga ttgcgcaatt cctcccctca aagatgccgc aagatctgtt tattgacctt      60
gcaagggcca tcggtgtcca ggccgcaccc tatgtcgacc ctctcgaggc agcgcttgtg     120
gcccaggccg agaagttctt ccccacggtc gttcatcaca cgcgcggctt tttggtcgcg     180
gtcgagtcac ccttggcccg tgagctgccc ttgatgaacc ccttccacgt gctgttgatc     240
gcgctcgctt acttggtcac ggtctttgtg ggcatgcaga tcatgaagaa cttttgaacgg     300
ttcgaggtca gacgttctc gctcttccac aacttttgtc tggtctcgat cagtgcctac     360
atgtgcggcg ggatcttgta cgaggcttac caggccaact atggactgtt tgagaacgcg     420
gccgatcata ccgtccaggg tcttcctatg gccaagatga tctggctctt ctacttctcc     480
aagatcatgg agtttgtcga caccatgatc atggtcctta agaagaacaa ccgccagatc     540
tcgttccttgc acgtctacca ccacagctcc atcttcacca tctggtggtt ggtcaccttt     600
gttgcaccca atggtgaagc ctacttctcg gctgcgttga actcgttcat ccacgtgatc     660
atgtacggct actacttcct gtccgccttg ggcttcaagc aggtgtcgtt catcaagttc     720
tacatcacgc gttcgcagat gacgcagttc tgcatgatgt cgatccagtc ctcctgggac     780
atgtatgcca tgaaggtgct tggccgcccc ggataccccct tcttcatcac cgccctgctt     840
tggttctaca tgtggaccat gctcggactc ttctacaact tctacagaaa gaacgccaag     900
ttggccaagc aggccaagat cgatgctgcc aaggagaagg caaggaagtt gcagtaa       957

<210> SEQ ID NO 35
<211> LENGTH: 1341
<212> TYPE: DNA
<213> ORGANISM: Mortierella alpina
```

<400> SEQUENCE: 35

```
atgggtgcgg acacaggaaa aaccttcacc tggcaagaac tcgcggcgca taacaccgag      60
gacagcctcc ttttggctat ccgtggcaat gtatacgatg tcacaaagtt cttgagccgt     120
catcctggtg aacggatac  tctcttgctc ggagctggcc gagatgtcac tccggttttt     180
gagatgtacc acgagtttgg agctgcagag ctatcatga  agaagtacta tgttggcaca     240
ctggtctcaa atgagttgcc catcttccca gagccaacgg tgttccataa gaccatcaag     300
ggcagagttg aggcatactt taaggaccgg aacatggatt ccaagaacag accagagatc     360
tggggacgat atgctctcat ctttggatcc ttgatcgcct cttactacgc gcagctcttt     420
gtaccgttcg tggtcgaacg tacatggctc caggtggtgt ttgctatcat catgggattt     480
gcgtgcgcgc aagtcggatt gaaccctctt cacgatgcct cccactttc  agtgaccccac    540
aaccccaccg tttggaagat tctcggagcc acgcacgact ttttcaacgg agcatcgtat     600
ctcgtgtgga tgtaccaaca tatgctcggc catcatccct ataccaacat tgctggagct     660
gatcccgatg tgtcgacctc tgagcccgat gttcgtcgta tcaagcccaa ccaaaagtgg     720
ttcgtcaacc acatcaacca gcacatgttt gttccttttcc tgtacggact gctggcgttc     780
aaggtgcgca tccaggacat caacatcttg tactttgtca agaccaatga cgccattcgt     840
gtcaaccccca tctcgacttg gcacaccgtc atgttctggg gcggaaaggc cttcttttgtc    900
tggtaccgct tgatcgttcc tatgcagtat ctgcccctga gcaaggtgtt gctcttgttt     960
accgtcgcag acatggtctc ttcttactgg ctggcgctga ccttccaggc gaaccacgtt    1020
gttgaggagg ttcagtggcc attgcctgat gagaatggaa tcatccaaaa ggattgggca    1080
gccatgcagg tcgagactac tcaggattac gcccacgatt cgcacctctg accagcatc    1140
acgggcagct tgaactacca gccgttcat  catctgttcc gaacgtttc  ccagcatcac    1200
taccctgata tcctggctat catcaaggac acctgcagcg agtacaaggt gccataccctc   1260
gtcaaggata ccttttggca agcgtttgct tcacatttgg agcacttgcg tgtgcttggt    1320
cttcgtccca aggaagagta a                                              1341
```

<210> SEQ ID NO 36
<211> LENGTH: 987
<212> TYPE: DNA
<213> ORGANISM: Mortierella alpina

<400> SEQUENCE: 36

```
atgtcatcaa tgtcatcaat agagcccgca ctgtcctcgt ttccaggcaa cctggcggtc      60
atccttgttt tctacctggc acttccacga cttcttgccg tcctgccaca aaagattcag     120
ttcatcgcca aatgtctcat tgtccttaca gccaccttcc tcatgtctgt ggcaggatgc     180
tttgtcgcca ttgtctgtgc tctcctccaa aagcgctatg ccataaatta cgtggttgcg     240
aggatctttt cttatatcgc atgcaggcct tgtggagtca cgttcaatat cgtgggcgaa     300
gaacacctcg agaacactcc agcaatcgtt gtctgcaacc accagagctc catggatatg     360
atggtcttgg gacgagtgtt cccaatgcgc tgcgtggtta tggccaagaa ggaacttcag     420
tactttccat ttctcggcat ctttatgacg ctgagcaatg ccatttttat tgaccgcaag     480
aatcataaga aggccattga gtctacaacc caggccgttg ctgacatgaa gaagcacaac     540
tctgggatct ggatcttccc cgagggaact cgctcccggc ttgacacggc cgacctgctg     600
ccattcaaga agggagcctt tcatcttgca atccagtcag gacttcccat cctacccatt     660
gtcagcgctg gatacaacca tatctacgat tctgccaagc gatctttccc tggcggtgag     720
```

```
ctcgagatca gggttttgga gcccatacct accacaggca tgacggccga tgatgtgaac    780
gatctgatgg agcggacacg ggcagtgatg ttgaagaacc taaaggagat ggatgtcaac    840
tccttggcag tatcttcaaa accctcgctc tcagtggacg agctcaagtc agcgcccgca    900
ctgaagcagg aggcgaagtc gactgcggtg gtggaggaag aggggggttag ctacgacagc    960 gtgaagaaga ggaagacggt caaggct                                        987
```

<210> SEQ ID NO 37
<211> LENGTH: 939
<212> TYPE: DNA
<213> ORGANISM: Mortierella alpina

<400> SEQUENCE: 37

```
atgtccatag gctcttctaa tcctgtccta ctggcagcga tccccttcgt ctacctttt     60 gtcctccctc gcatcctcgc cttcctccct caaaaggccc agttcctcgc aaaatgtatc    120
gtggtcttga tcgccaccct catcatgtcc gtcgcaggct gcctcatctc tattgtctgt    180
gcgctcctcg acaaacgcta tgtgatcaac tacgttgtct caagactctt ctcattcctt    240
gcagcaagac cctgcggcgt cacttacaag attgtgggcg aggagcattt ggataagtac    300
cccgccattg tcgtttgcaa ccaccagagc tcaatggaca tgatggttct gggacgcgtc    360
ttccctaagc actgtgtcgt catggcaaag aaggagcttc tttactttcc gttcctgggc    420
atgttcatga aactgagcaa tgccattttc atcgaccgca agaaccataa gaaggcgatc    480
gagtctacca cccaagctgt cgccgacatg aagaagcaca actctggaat ctggattttc    540
cccgaaggaa cacgttcccg cttggacaag gccgatctct gcccttcaa gaagggagcc     600 ttccacctcg ccattcaagc tcaacttccc atcctcccca tcgtctcgca aggatactca    660
cacatctatg attcatcaaa acgctacttc cccggtggag agctcgagat cagagtcctg    720
gaacccatcc ctaccaaggg attgaccaca gacgatgtca acgacctgat ggacaagaca    780
cgcaacttga tgctcaagca cctcaaggac atggattctc attgctcctc cgccgtcgga    840
aacggatctc tgcctctcga cgccgacatt gcaaagtcaa cggctacatc gatcggaaac    900
acagacgatg ctgtcacaaa gaggaggaca ctgaaagag                          939
```

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
tctgagatgg atgaatccac caccaccac                                       29
```

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
gtcgactcaa ccagacgata cttgctgcag ag                                   32
```

<210> SEQ ID NO 40
<211> LENGTH: 343
<212> TYPE: PRT

<213> ORGANISM: Ustilago maydis 521

<400> SEQUENCE: 40

Met Ala Val Leu Ser Lys Ser Phe Ser Thr Leu Thr Ala Gly Ala Leu
1               5                   10                  15

Leu Leu Leu Ala Leu Ile Ser Pro Arg Ser Gln Lys Leu Arg Phe Tyr
            20                  25                  30

Leu Asn Ser Ile Ile Tyr Ile Ala Gly Leu Gly Ile Cys Ser Val Trp
        35                  40                  45

Gly Ile Phe Val Ser Ile Leu Leu Ser Leu Val Pro Gly Gln Arg Leu
    50                  55                  60

Asn Ile Asn Lys Val Val Ala Arg Ser Phe Trp Arg Leu Thr Ser Pro
65                  70                  75                  80

Leu Val Gly Ile Arg Phe Ile Val Glu Gly Glu His Phe Gln Ala
                    85                  90                  95

Ala Arg Pro Ala Val Val Gly Asn His Gln Thr Ala Met Asp Ile
                100                 105                 110

Leu Tyr Leu Gly Arg Ile Phe Pro Gly Asn Ala Ser Ile Met Ala Lys
            115                 120                 125

Lys Glu Leu Gln Phe Ala Pro Leu Leu Gly Gln Phe Met Ser Leu Ser
130                 135                 140

Gly Ala Val Phe Ile Asn Arg Lys Asn Leu Lys Asp Ser Ile Lys Ala
145                 150                 155                 160

Phe Gln Gln Val Gly Glu Thr Met Asn Asn Lys Lys Leu Ser Leu Trp
                165                 170                 175

Ile Phe Pro Glu Gly Thr Arg Ser Gly Leu Ala Thr Pro Asp Leu Leu
            180                 185                 190

Pro Phe Lys Lys Gly Ala Phe His Leu Ala Ile Gln Ala Gly Val Pro
        195                 200                 205

Val Val Pro Val Val Cys Glu Asn Tyr Asn Arg Leu Phe Asp Ser Arg
210                 215                 220

Ser Arg Phe Glu Ser Gly Thr Ile Arg Ile Lys Val Leu Ala Pro Ile
225                 230                 235                 240

Pro Thr Lys His Leu Thr Ala Ala Asp Ala Asn Glu Leu Thr Glu Lys
                245                 250                 255

Val Arg Gln Leu Met Leu Asp Glu Leu Arg Asn Met Asp Ala Glu Arg
            260                 265                 270

Gln Arg Thr Asp Thr Ala Ala Ser Val Asn Asn Asp Glu Ala Ser Met
        275                 280                 285

Ala Gly Val Ala Gly Phe Phe Ser Lys Phe Val Gly Thr Ala Asn Ser
    290                 295                 300

Trp Gln Ser Val Asn Ser Asn Val Asp Lys Glu Lys Arg Leu Arg
305                 310                 315                 320

Gln Asn Gly Thr Thr Gly Glu Asn Pro Glu Asp Tyr His Leu Val Ser
                325                 330                 335

Glu Ala Gln Lys Lys Ser Asn
            340

<210> SEQ ID NO 41
<211> LENGTH: 291
<212> TYPE: PRT
<213> ORGANISM: Emericella nidulans

<400> SEQUENCE: 41

Met Ser Leu Leu Tyr Tyr Ile Ala Ser Gly Ala Ser Thr Tyr Ile Ala
1               5                   10                  15

Phe Thr Ala Ser Leu Phe Leu Val Gly Gln Lys Val Pro Arg Ala Ser
                20                  25                  30

Phe Val Ala Arg Cys Leu Ala Ser Tyr Gly Ser Leu Val Cys Ala
            35                  40                  45

Met Tyr Gly Val Val Ala Ser Ile Val Leu Arg Val Gly Tyr Gly
 50                  55                  60

Arg Ile Ser Gln Trp Ala Thr Ala Arg Ser Phe Lys Trp Val Met Arg
 65                  70                  75                  80

Phe Thr Thr Gly Val Arg Phe Asp Ile Val Glu Gly Lys Glu Tyr Leu
                85                  90                  95

Ser Thr Arg Pro Ala Val Ile Ile Gly Asn His Gln Ser Glu Leu Asp
            100                 105                 110

Val Leu Met Leu Gly Glu Ile Phe Pro Pro Tyr Cys Ser Val Thr Ala
        115                 120                 125

Lys Lys Ser Leu Arg Tyr Val Pro Phe Leu Gly Trp Phe Met Ala Leu
130                 135                 140

Ser Arg Thr Val Phe Ile Asp Arg Ala Asn Arg Gln Thr Ala Val Lys
145                 150                 155                 160

Ala Phe Asp Ser Ala Ala Glu Glu Met Arg Ser His Arg Gln Ser Val
                165                 170                 175

Phe Ile Phe Ala Glu Gly Thr Arg Ser Tyr Ser Glu Lys Pro Glu Leu
            180                 185                 190

Leu Pro Phe Lys Lys Gly Ala Phe His Leu Ala Val Lys Ala Gly Val
        195                 200                 205

Pro Ile Val Pro Val Val Glu Asn Tyr Ser His Ile Leu Ala Pro
    210                 215                 220

Lys Lys Phe Arg Phe Glu Ala Gly Ser Ile Lys Val Lys Val Leu Pro
225                 230                 235                 240

Pro Ile Ser Thr Asp Gly Leu Thr Ala Ala Asp Val Asp Gly Leu Thr
                245                 250                 255

Thr Ser Thr Arg Glu Ser Met Leu Asn Thr Leu Leu Glu Leu Ser Asn
            260                 265                 270

Ala Gly Pro Ala Asp Leu Pro Ser Ser Ser Lys Gly Gln Ser Thr Ala
        275                 280                 285

Val Asp Leu
    290

<210> SEQ ID NO 42
<211> LENGTH: 303
<212> TYPE: PRT
<213> ORGANISM: Saccharomyces cerevisiae

<400> SEQUENCE: 42

Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
                20                  25                  30

Leu Cys Thr Leu Ile Gly Lys Gln His Leu Ala Gln Trp Ile Thr Ala
            35                  40                  45

Arg Cys Phe Tyr His Val Met Lys Leu Met Leu Gly Leu Asp Val Lys
 50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
              100                 105                 110

Leu Gly Trp Phe Met Ala Leu Ser Gly Thr Tyr Phe Leu Asp Arg Ser
          115                 120                 125

Lys Arg Gln Glu Ala Ile Asp Thr Leu Asn Lys Gly Leu Glu Asn Val
      130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
              165                 170                 175

Leu Ala Gln Gln Gly Lys Ile Pro Ile Val Pro Val Val Ser Asn
          180                 185                 190

Thr Ser Thr Leu Val Ser Pro Lys Tyr Gly Val Phe Asn Arg Gly Cys
          195                 200                 205

Met Ile Val Arg Ile Leu Lys Pro Ile Ser Thr Glu Asn Leu Thr Lys
          210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
              245                 250                 255

Pro Pro Gln Ala Ile Glu Tyr Ala Ala Leu Gln His Asp Lys Lys Val
          260                 265                 270

Asn Lys Lys Ile Lys Asn Glu Pro Val Pro Ser Val Ser Ile Ser Asn
          275                 280                 285

Asp Val Asn Thr His Asn Glu Gly Ser Ser Val Lys Lys Met His
          290                 295                 300

<210> SEQ ID NO 43
<211> LENGTH: 279
<212> TYPE: PRT
<213> ORGANISM: Schizosaccharomyces pombe 972h

<400> SEQUENCE: 43

Met Gly Phe Ile Lys Ser Thr Leu Leu Ala Thr Val Thr Val Phe Val
1               5                   10                  15

Gly Leu Cys Gly Ile Asn Arg Phe Phe Thr Leu Pro Lys Cys Ile Arg
            20                  25                  30

Tyr His Phe Arg Tyr Phe Ala Cys His Thr Phe Leu Ala Ile Ser Ser
        35                  40                  45

Ala Tyr Gly Val Ile Ala Ser Val Val Ala Arg Leu Cys Gly Tyr Pro
    50                  55                  60

Val Met Gly Gln Tyr Leu Thr Ala Lys Ala Tyr Tyr Gly Leu Ala Ser
65                  70                  75                  80

Thr Ile Leu Asp Phe Arg Phe Lys Ile Glu Asn Glu Ile Leu Arg
            85                  90                  95

Lys His Lys Ser Ala Val Leu Val Asn His Gln Ser Glu Leu Asp
        100                 105                 110

Ile Leu Ala Ile Gly Arg Thr Phe Gly Pro Asn Tyr Ser Val Ile Ala
    115                 120                 125

Lys Lys Ser Leu Arg Tyr Val Pro Ile Leu Gly Trp Phe Met Ile Leu
130                 135                 140

Ser Asp Val Val Phe Ile Asp Arg Ser Arg Arg Ser Asp Ala Ile Gln
145                 150                 155                 160

Leu Phe Ala Lys Ala Ala Arg Arg Met Arg Lys Glu Asn Ile Ser Ile
            165                 170                 175

```
Trp Val Phe Ala Glu Gly Thr Arg Ser Tyr Ser Leu Lys Pro Cys Leu
            180                 185                 190

Leu Pro Leu Lys Lys Gly Ala Phe His Leu Ala Val Gln Ala Gln Val
        195                 200                 205

Pro Ile Ile Pro Ile Ala Ile Gln Thr Tyr Gly His Leu Phe His Pro
    210                 215                 220

Pro Thr Lys Val Phe Asn Lys Gly Ala Leu Ile Lys Val Leu Asp
225                 230                 235                 240

Pro Ile Pro Thr Glu Gly Lys Thr Ala Glu Asp Val Asn Asp Leu Leu
            245                 250                 255

His Glu Thr Glu Thr Ala Met Asn Asn Ala Leu Val Glu Ile Asp Asp
            260                 265                 270

Tyr Gly Lys Val Lys Lys Gln
            275
```

<210> SEQ ID NO 44
<211> LENGTH: 282
<212> TYPE: PRT
<213> ORGANISM: Caenorhabditis elegans

<400> SEQUENCE: 44

```
Met Glu Asn Phe Trp Ser Ile Val Val Phe Leu Leu Ser Ile Leu
1               5                   10                  15

Phe Ile Leu Tyr Asn Ile Ser Thr Val Cys His Tyr Tyr Met Arg Ile
            20                  25                  30

Ser Phe Tyr Tyr Phe Thr Ile Leu Leu His Gly Met Glu Val Cys Val
        35                  40                  45

Thr Met Ile Pro Ser Trp Leu Asn Gly Lys Gly Ala Asp Tyr Val Phe
    50                  55                  60

His Ser Phe Phe Tyr Trp Cys Lys Trp Thr Gly Val His Thr Thr Val
65                  70                  75                  80

Tyr Gly Tyr Glu Lys Thr Gln Val Glu Gly Pro Ala Val Val Ile Cys
            85                  90                  95

Asn His Gln Ser Ser Leu Asp Ile Leu Ser Met Ala Ser Ile Trp Pro
            100                 105                 110

Lys Asn Cys Val Val Met Met Lys Arg Ile Leu Ala Tyr Val Pro Phe
        115                 120                 125

Phe Asn Leu Gly Ala Tyr Phe Ser Asn Thr Ile Phe Ile Asp Arg Tyr
    130                 135                 140

Asn Arg Glu Arg Ala Met Ala Ser Val Asp Tyr Cys Ala Ser Glu Met
145                 150                 155                 160

Lys Asn Arg Asn Leu Lys Leu Trp Val Phe Pro Glu Gly Thr Arg Asn
            165                 170                 175

Arg Glu Gly Gly Phe Ile Pro Phe Lys Lys Gly Ala Phe Asn Ile Ala
            180                 185                 190

Val Arg Ala Gln Ile Pro Ile Ile Pro Val Val Phe Ser Asp Tyr Arg
        195                 200                 205

Asp Phe Tyr Ser Lys Pro Gly Arg Tyr Phe Lys Asn Asp Gly Glu Val
    210                 215                 220

Val Ile Arg Val Leu Asp Ala Ile Pro Thr Lys Gly Leu Thr Leu Asp
225                 230                 235                 240

Asp Val Ser Glu Leu Ser Asp Met Cys Arg Asp Val Met Leu Ala Ala
            245                 250                 255

Tyr Lys Glu Val Thr Leu Glu Ala Gln Gln Arg Asn Ala Thr Arg Arg
            260                 265                 270
```

```
Gly Glu Thr Lys Asp Gly Lys Lys Ser Glu
        275                 280
```

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggtgaagggg gaattcttc                                                  19

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgtcgacgt ggcttaatgc atc                                             23

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cacaccacac attcaacatc                                                 20

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gaatcgtaga tatggttgta tccagcgct                                       29

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctggcggtca tccttgtttt ctacctg                                         27

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

-continued

```
gaatcataga tgtgtgagta tccttgcga                                29

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttctaatcct gtcctactgg cagcg                                    25

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgcatcccgc aaacacacac                                          20

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tttttttttt tttttttttt tttttttttt                               30
```